US006984635B1

(12) United States Patent
Schreiber et al.

(10) Patent No.: US 6,984,635 B1
(45) Date of Patent: Jan. 10, 2006

(54) DIMERIZING AGENTS, THEIR PRODUCTION AND USE

(75) Inventors: Stuart L. Schreiber, Boston, MA (US); Gerald R. Crabtree, Woodside, CA (US); Stephen D. Liberles, Somerville, MA (US)

(73) Assignees: Board of Trustees of The Leland Stanford Jr. University, Palo Alto, CA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/248,755

(22) Filed: Feb. 12, 1999

Related U.S. Application Data

(60) Provisional application No. 60/074,584, filed on Feb. 13, 1998.

(51) Int. Cl.
*A61K 31/395* (2006.01)
*C07D 491/18* (2006.01)
*C07D 491/16* (2006.01)
*A61P 37/00* (2006.01)

(52) U.S. Cl. ...................... 514/183; 514/291; 540/456; 540/455

(58) Field of Classification Search ................ 540/456; 514/291, 183
See application file for complete search history.

(56) References Cited

U.S. PATENT DOCUMENTS

| 4,797,368 | A | | 1/1989 | Carter et al. ................. 435/320 |
| 5,139,941 | A | | 8/1992 | Muzyczka et al. ........ 435/172.3 |
| 5,173,414 | A | | 12/1992 | Lebkowski et al. ...... 435/172.3 |
| 5,252,479 | A | | 10/1993 | Srivastava ............... 435/235.1 |
| 5,310,903 | A | * | 5/1994 | Goulet ........................ 540/456 |
| 5,314,471 | A | | 5/1994 | Brauker et al. ............... 623/11 |
| 5,340,903 | A | | 8/1994 | Tetart et al. ................. 528/164 |
| 5,354,678 | A | | 10/1994 | Lebkowski et al. ...... 435/172.3 |
| 5,362,718 | A | * | 11/1994 | Skotnicki ..................... 514/63 |
| 5,373,014 | A | | 12/1994 | Failli et al. ................. 514/291 |
| 5,378,836 | A | | 1/1995 | Kao et al. ................... 540/456 |
| 5,387,680 | A | | 2/1995 | Nelson ....................... 540/456 |
| 5,429,821 | A | | 7/1995 | Dorian et al. ............... 424/424 |
| 5,436,146 | A | | 7/1995 | Shenk et al. ............. 435/172.3 |
| 5,454,935 | A | | 10/1995 | Magaraggia ................ 209/169 |
| 5,525,610 | A | * | 6/1996 | Caufield ..................... 514/291 |
| 5,527,907 | A | * | 6/1996 | Or ............................. 540/456 |
| 5,583,139 | A | | 12/1996 | Or et al. ..................... 514/291 |
| 5,658,776 | A | | 8/1997 | Flotte et al. ............. 435/172.3 |

FOREIGN PATENT DOCUMENTS

| WO | WO 92/19595 | 11/1992 |
| WO | WO 93/13663 | 7/1993 |
| WO | WO 93/24641 | 12/1993 |
| WO | WO 94/02136 | 2/1994 |
| WO | WO 94/18207 | 8/1994 |
| WO | WO 94/18317 | 8/1994 |
| WO | WO 94/28938 | 12/1994 |
| WO | WO 95/02684 | 1/1995 |
| WO | WO 95/04521 | 2/1995 |
| WO | WO 95/16691 | 6/1995 |
| WO | WO 95/33052 | 12/1995 |
| WO | WO 96/06111 | 2/1996 |
| WO | WO 96/13597 | 5/1996 |
| WO | WO 96/20951 | 7/1996 |
| WO | WO 96/26285 | 8/1996 |
| WO | WO 96/39350 | 12/1996 |
| WO | WO 96/41865 | 12/1996 |
| WO | WO 97/02358 | 1/1997 |
| WO | WO 97/08298 | 3/1997 |
| WO | WO 97/31899 | 9/1997 |
| WO | WO 98/02441 | 1/1998 |

OTHER PUBLICATIONS

Aebischer, P. et al. "Functional Recovery in Hemiparkinsonian Primates Transplanted with Polymer-Encapsulated PC12 Cells" *Experimental Neurology* 126(2):151-158 (1994).

Aitken, A. et al. "Idenitification of the $NH_2$-Terminal Blocking Group of Calcineurin B as Myristic Acid" *FEBS Letters* 150(2):314-318 (Dec. 1982).

Ao, Z. et al. "Microencapsulation Improves Canine Islet Survival In Vivo" et al. *Transplantation Proceedings* 27(6): 3349-3350 (Dec. 1995).

Behringer, R.R. et al. "Dwarf Mice Produced by Genetic Ablation of Growth Hormone-Expressing Cells" *Genes & Development* 2:453-461 (1988).

Belshaw et al. "Controlling Protein Association and Subcellular Localization with a Synthetic Ligand That Induces Heterodimerizationof Proteins" *Proc. Natl. Acad. Sci. U.S.A.* 93:4604-4607 (May 1996).

Borelli, E. et al. "Targeting of an Inducible Toxic Phenotype in Animal Cells" *Proc. Natl. Acad. Sci. U.S.A.* 85:7572-7576 (Oct. 1988).

Breitman, M.L. et al. "Genetic Ablation in Transgenic Mice with an Attenuated Diphtheria Toxin A Gene" *Molecular and Cellular Biology* 10:474-476 (Feb. 1990).

Breitman, M.L. et al. "Genetic Ablation: Targeted Expression of a Toxin Gene Causes Microphtalmia in Transgenic Mice" *Science* 238:1563-1565 (Dec. 1987).

Brown, E.J. et al. "A Mammalian Protein Targeted by G1-Arresting Rapamycin-Receptor Complex" *Nature* 369: 756-758 (Jun. 1994).

(Continued)

*Primary Examiner*—Evelyn Mei Huang
(74) *Attorney, Agent, or Firm*—Fish & Neave IP Group Ropes & Gray LLP

(57) ABSTRACT

Materials and methods are disclosed for regulation of biological events such as target gene transcription and growth, proliferation or differentiation of engineered cells.

5 Claims, No Drawings

OTHER PUBLICATIONS

Caldwell, R.C. and Joyce, G.F. "Randomization of Genes by PCR Mutagenesis" *PCR Methods and Applications* 2:28-33 (1992).

Carr, S.A. et al "n-Tetradecanoyl is the $NH_2$-Terminal Blocking Group of the Catalytic Subunit of Cyclic AMP-Dependent Protein Kinase from Bovine Cardiac Muscle" *Proc. Natl. Acad. Sci. U.S.A.* 79:6128-6131 (Oct. 1982.

Carter et al. "Adeno-Associated Virus Vectors" *Current Opin. In Biotech.* 3:533-539 (1992).

Chaffin, K.E. et al. "Dissection of Thymocyte Signaling Pathways by In Vivo Expression of Pertussis Toxin ADP-Ribosyltransferase" *The EMBO Journal* 9(12):3821-3829 (1990).

Chang, P.L. et al. "Delivery of Recominbant Gene Products with Microencapsulated Cells In Vivo" *Human Gene Therapy* 4:433-440 (1993).

Chen, J. "Identification of an 11-kDa FKBP12-rapamycin-binding Domain Within the 289-kDa FKBP12-rapamycin-associated Protein and Characterization of a Critical Serine Residue" *Proc. Natl. Acad. Sci. U.S.A.* 92:4947-4951 (May 1995).

Chiu, M.I. et al. "RAPT1, a Mammalian Homolog of Yeast Tor, Interacts with the FKBP12/Rapamycin Complex" *Proc. Natl. Acad. Sci. U.S.A.* 91:12574-12578 (Dec. 1994).

Clackson, T. and Wells, J.A. "In Vitro Selection from Protein and Peptide Libraries" *TIBTECH* 12:173-184 (May 1994).

Crameri, A. et al. "Construction and Evolution of Antibody-Phage Libraries by DNA Shuffling" *Nature Medicine* 2(1): 100-103 (Jan. 1996).

Cunningham, B.C. and Wells, J.A. "High-Resolution Epitope Mapping of hGH-Receptor Interactions by Alanine-Scanning Mutagenesis" *Science* 244:1081-1085 (Jun. 1989).

Dennis, M.S. and Lazarus, R.A. "Kunitz Domain Inhibitors of Tissue Factor-Factor VIIa" *Journal of Biological Chemistry* 269(35)22129-22136 (1994).

Dubensky, T.W. et al. "Direct Transfection of Viral and Plasmid DNA into the Liver of Spleen of Mice" *Proc. Natl. Acad. Sci. U.S.A.* 81:7529-7533 (Dec. 1984).

Emerich, D.F. et al. "Intrastriatal Implants of Polymer-Encapsulated PC12 Cells" Effects on Motor Function in Aged Rats *Prog. Neuro-Psychopharmacol. & Biol. Psychiat.* 18:935-946 (1994).

Emrich, D.F. et al. "Polymer-Encapsulated PC12 Cells Promote Recovery of Motor Functionin Aged Rats" *Experimental Neurology* 122:37-47 (1993).

Ferry, N. et al. "Retroviral-Mediated Gene Transfer into Hepatocytes In Vivo" *Proc. Natl. Acad. Sci. U.S.A.* 88:8377-8381 (Oct. 1991).

Fields, S. and Song, O-k "A Novel Genetic System to Detect Protein-Protein Interactions" *Nature* 340:245-246 (Jul. 1989).

Fisher, K.J. et al. "Recombinant Adenovirus Deleted of All Viral Genes for Gene Therapy of Cystic Fibrosis" *Virology* 217:11-22 (1996).

Flotte et al. "Expression of the Cystic Fibrosis Transmembrane Conductance Regulator from a Novel Adeno-Associated Virus Promoter" *The Journal of Biological Chemistry* 268(5):3781-3790 (1993).

Goldman, M.J. et al. "Transfer of the CFTR Gene to the Lung of Nonhuman Primates with E1-Deleted, E2a-Defective Recombinant Adenoviruses: A Preclinical Toxicology Study" *Human Gene Therapy* 6:839-851 (Jul. 1995).

Hatzogluo, M. et al. "Hepatic Gene Transfer in Animals Using Retroviruses Containing the Promoter From the Gene for Phosphoenolpyruvate Carboxykinase" *J. Biol. Chem.* 265(28):17285-17293 (1990).

Henderson, L.E. et al. "Myristyl Amino-Terminal Acylation of Murine Retrovirus proteins: An Unusual Post-Translational Protein Modification" *Proc. Natl. Acad. Sci. U.S.A.* 80:339-343 (Jan. 1983).

Heyman, R.A. et al. "Thymidine Kinase Obliteration: Creation of Transgenic Mice with Controlled Immune Deficiency" *Proc. Natl. Acad. Sci. U.S.A.* 86:2698-2702 (Apr. 1989).

Hiebert, S.W. et al. "E1A-Dependent Trans-Activation of the Human MYC Promoter is Mediated by the E2F Factor" *Proc. Natl. Acad. Sci. U.S.A.* 86:3594-3598 (May 1989).

Ho, S.N. et al. "Dimeric Ligands Define a Role for Transcriptional Activation Domains in Reinitiation" *Nature* 382:822-826 (Aug. 1996).

Holsinger, L.J. et al. "Signal transduction in T Lymphocytes Using a Conditional Allele of Sos" *Proc. Natl. Acad. Sci. U.S.A.* 92:9810-9814 (Oct. 1995).

Hu, J.C. "Repressor Fusions as a Tool to Study Protein-Protein Interactions" *Structure* 3:431-433 (May 1995).

Hu, J.C. et al. "Sequence Requirements for Coiled-Coils: Analysis with λ Repressor-GCN4 Leucine Zipper Fusions" *Science* 250: 1400-1403 (Dec. 1990).

Joyner, A.L. et al. "Production of a Mutation in Mouse EN-2 Gene by Homologous Recombination in Embryonic Stem Cells" *Nature* 338:153-156 (Mar. 1989).

Kaneda, Y et al. "Increased Expression of DNA Cointroduced with Nuclear Protein in Adult Rat Liver" *Science* 243:375-378 (Jan. 1989).

Kaur, S. et al. Targeted Ablation of α-Crystallin-Synthesizing Cells Produces Lens-Deficient Eyes in Transgenic Mice *Development* 105:613-619 (1989).

Kay, J.E. "Structure-function Relationships in the FK506-binding Protein (FKBP) Family of Peptidylprolyl cic-trans Isomerases" *Biochem. J.* 314:361-385 (1996).

Korbutt et al. "Successful Reversal of Diabetes in Nude Mice by Transplantation of Microencapsulated Porcine Neonatal Islet Cell Aggregates" *Transplantation Proceedings* 27(6):3212 (Dec. 1995).

Kordower, J.H. et al. "The Aged Monkey Basal Forebrain: Rescue and Sprouting of Axotomized Basal Forebrain Neurons After Grafts of Encapsulated Cells Secreting Human Nerve Growth Factor" *Proc. Natl. Acad. Sci. U.S.A.* 91(23):10898-10902 (Nov. 1994).

Kotin, R.M. "Prospect for the Use of Adeno-Associated Virus as a Vector for Human Gene Therapy" *Human Gene Therapy* 5:793-801 (1994).

Kunz, J. et al. "Target of Rapamycin in Yeast, TOR2, Is and Essential Phosphatidylinositol Kinase Homolog Required for $G_1$ Progression" *Cell* 73:585-596 (May 1993).

Lakey, J.R.T. et al. "Recovery and In Vivo Function of Canine Islets Cryopreserved in a Freezer Bag" *Transplantation Proceedings* 27(6):3266 (Dec. 1995).

Landel, C.P. et al. "Lens-Specific Expression of Recombinant Ricin Induces Developmental Defects in the Eyes of Transgenic Mice" *Genes Development* 2:1168-1178 (1988).

Lee, K.J. et al. "Myosin Light Chain-2 Luciferase Transgenic Mice Reveal Distinct Regulatory Programs for Cardiac and Skeletal Muscle-Specific Expression of a Singel Contractile Protein Gene" *J. Biol. Chem.* 267(22):15875-15885 (1992).

Liberles, S.D. et al. "Inducible Gene Expression and Protein Translocation Using Nontoxic Ligands Indentified by a Mammalian Three-Hybrid Screen" *Proc. Natl. Acad. Sci. U.S.A.* 94:7825-7830 (Jul. 1987).
Lowman, H.B. and Wells, J.A. "Monovalent Phage display: A Method for Selecting Variant Proteins from Random Libraries" *Methods* 3(3):205-216 (1991).
Luengo, J.I. et al. "Studies on Selective Reductions of Rapamycin" *Tetrahedron Letters* 35:6469 (1994).
Luo, Z. et al. "Oligomerization Activates c-Raf-1 Through a Ras-Dependent Mechanism" *Nature* 383:181-185 (Sep. 1996).
Mansour, S.L. et al. "Disruption of the Proto-Oncogene int-2 in Mouse Embryo-Derived Stem Cells: A General Strategy for Targeting Mutations to Non-Selectable Genes" *Nature* 336:348-352 (Nov. 1988).
Messing, A. et al. "$P_0$ Promoter Directs Expression of Reporter and Toxin Genes to Schwann Cells of Transgenic Mice" *Neuron* 8:507-520 (Mar. 1992).
Miskimins, R. et al. "Cell and Tissue-Specific Expression of a Heterologous Gene Under Control of the Myelin Basic Protein Gene Promoter in Transgenic Mice" *Dev. Brain Res.* 65:217-221 (1992).
Muscat, G.E. et al. "The Human Skeletal α-Actin Gene is Regulated by a Muscle-Specific Enhancer that Binds Three Nuclear Factors" *Gene Expression* 2(2):111-126 (1992).
Ornitz, D.M. et al. "Specific Expression of an Elastase-Human Growth Hormone Fusion Gene in Pancreatic Acinar Cells of Transgenic Mice" *Nature* 131:600-603 (1985).
Palmiter, R.D. et al. "Cell Lineage Ablation in Transgenic Mice by Cell-Specific Expression of a Toxin Gene" *Cell* 50:435-443 (Jul. 1987).
Pellman, D. et al. "An N-Terminal Peptide from $p60^{src}$ Can Direct Myristylation and Plasma Membrane Localization when Fused to Heterologous Proteins" *Nature* 314:374-377 (Mar. 1985).
Pomerantz, J.L. et al. "Structure-Based Design of Transcription Factors" *Science* 267:93-96 (Jan. 1995).
Pruschy, M.N. et al. "Mechanistic Studies of a Signaling Pathway Activated by the Organic Dimerizer FK1012" *Chemistry & Biology* 1:163-172 (Nov. 1994).
Qin, L. et al. "Adenovirus—Mediated Gene Transfer of Viral Interleukin-10 Inhibits the Immune Response to Both Alloantigen and Adenoviral Antigen" *Human Gene Therapy* 8:1365-1374 (Jul. 1997).
Rajotte, R.V. et al. "Cryopreservation of Microencapsulated Canine Islets" *Transplantation Proceedings* 27(6):3389 (Dec. 1995).
Reddy, L.V. et al. "Depletion of CD4 Cells in Mice with Intraperitoneal Injection of Alginate-Encapsulated GK 1.5 Hybridoma Cells: A Potential Use in Development of Animal Models for Infectious Diseases" *J. Infec. Dis.* 168 (4):1082-1083 (1993).
Reeben, M. et al. "Tissue-Specific Expression of Rat Light Neurofilament Promoter-Driven Reporter Gene in Transgenic Mice" *Biochemical and Biophysical Research Communications* 192(2):465-470 (Apr. 1993).
Rivera, V.M. et al. "A Humanized System for Pharmacologic Control of Gene Expression" *Nature Medicine* 2:1098-1032 (Sep. 1996).
Ross, S.R. et al. "Targeted Expression of a Toxin Gene to Adipose Tissue: Transgenic Mice Resistant to Obesity" *Genes & Development* 7:1318-1324 (1993).

Sagen, J. et al. "Transplants of Immunologically Isolated Xenogeneic Chromaffin Cells Provide a Long-Term Source of Pain-Reducing Neuroactive Substances" *The Journal of Neuroscience* 13(6):2415-2423 (Jun. 1993).
Savelkoul, H.F.J. et al. "Modulation of Systemic Cytokine Levels by Implantation of Alginate Encapsulated Cells" *Journal of Immunological Methods* 170:185-196 (1994).
Schubert, J. et al. "Total Synthesis of a Fortimicin Aglycone" *Agnew Chem. Int. Eng. Ed.* 23:167- (1984).
Sierkierka, J.J. et al. "A Cytosolic Binding Protein for the Immunosuppressant FK506 Has Peptidyl-prolyl Isomerase Activity But Is Distinct From Cyclophilin" *Nature* 341:755-757 (Oct. 1989).
Spencer, D.M. "Creating Conditional Mutations in Mammals" *TIG* 12(5):181-187 (May 1996).
Spencer, D.M. et al. "Controlling Signal Transduction with Synthetic Ligands" *Science* 262:1019-1024 (Nov. 1993).
Spencer, D.M. et al. "Functional Analysis of Fas Signaling In Vivo Using Synthetic Inducers of Dimerization" *Current Biology* 6(7):839-847 (1996).
Spencer, D.M. et al. "A General Strategy for Producing Conditional Alleses of Src-Like Tyrosine Kinases" *Proc. Natl. Acad. Sci. U.S.A.* 92:9805-9809 (Oct. 1995).
Staendart, R.F. et al. "Molecular Cloning and Overexpression of the Human FK506-binding Protein FKBP" *Nature* 346:671-674 (Aug. 1990).
Stemmer, W.P.C. "Rapid Evolution of a Protein In Vitro by DNA Shuffling" 370:389-391 (Aug. 1994).
Stern, L.J. and Wiley, D.C. "Antigenic Peptide Binding by Class I and Class II Histocompatibility Proteins" *Structure* 2:245-251 (Apr. 1994).
Tai, I.T. and Sun, A.M. "Microencapsulation of Recombinant Cells: A New Delivery System for Gene Therapy" *The FASEB Journal* 7:1061-1069 (1993).
Thomas, K.R. et al. "Site-Directed Mutagenesis by Gene Targeting in Mouse Embryo-Derived Stem Cells" *Cell* 51:503-512 (Nov. 1987).
Towler, D.A. and Gordon, J.I. "The Biology and Enzymology of Eukaryotic Protein Acylation" *Ann. Rev. Biochem.* 57:69-99 (1988).
Uludag, H. and Sefton, M.V. "Microencapsulated Human Hepatoma (HepG2) Cells: In Vitro Growth and Protein Release" *Journal of Biomedical Materials Research* 27: 1213-1224 (1993).
Van Duyne, G.D. et al. "Atomic Structure of the Rapamycin Human Immunophilin FKBP-12 Complex" *J. Am. Chem. Soc.* 113:7433-7434 (1991).
Verma, I.M. and Somia, N. "Gene Therapy—Promises, Problems, and Prospects" *Nature* 389:239-242 (Sep. 1997).
Winn, S.R. et al. "Polymer-Encapsulated Cells Genetically Modified to Secrete Human Nerve Growth Factor Promote the Survival of Axotomized Septal Cholinergic Neurons" *Proc. Natl. Acad. Sci. U.S.A.* 91:2324-2328 (Mar. 1994).
Nickmilder, M.J.M. et al. "Isolation and Identification of New Rapamycin Dihydrodiol Metabolites from Dexamethasone-induced Rat Liver Microsomes" *Xenobiotica* 27(9):869-883 (1997).
Sedrani, R. et al. "Dihydroxylation of the Triene Subunit of Rapamycin" *J. Org. Chem.* 63:10069-10073 (1998).

* cited by examiner

DIMERIZING AGENTS, THEIR PRODUCTION AND USE

RELATED APPLICATIONS

This application claims the benefit of priority under 35 U.S.C. 119(e) to copending U.S. Provisional Application No. 60/074,584, including Appendix A, filed Feb. 13, 1998, the entire contents of which are hereby incorporated by reference.

BACKGROUND OF THE INVENTION

Rapamycin is a macrolide antibiotic produced by *Streptomyces hygroscopicus* which binds to a FK506-binding protein, FKBP, with high affinity to form a rapamycin:FKBP complex. Reported Kd values for that interaction are as low as 200 pM. The rapamycin:FKBP complex binds with high affinity to the large cellular protein, FRAP, to form a tripartite, [FKBP:rapamycin]:[FRAP], complex. In that complex rapamycin acts as a dimerizer or adapter to join FKBP to FRAP.

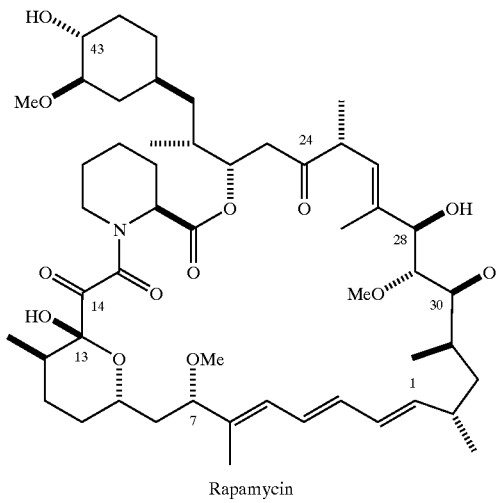

Rapamycin

A number of naturally occurring FK506 binding proteins (FKBPs) are known. See e.g. Kay, 1996, Biochem. J. 314:361–385 (review). FKBP-derived domains have been incorporated in the design of chimeric proteins for use in biological switches in genetically engineered cells. Such switches rely upon ligand-mediated multimerization of the protein components to trigger a desired biological event. See e.g. Spencer et al, 1993, Science 262:1019–1024 and PCT/US94/01617. While the potent immunosuppressive activity of FK506 would limit its utility as a multimerizing agent, especially in animals, dimers of FK506 (and related compounds) can be made which lack such immunosuppressive activity. Such dimers have been shown to be effective for multimerizing chimeric proteins containing FKBP-derived ligand binding domains.

Rapamycin, like FK506, is also capable of multimerizing appropriately designed chimeric proteins. Biological switches using rapamycin or various derivatives or analogs thereof ("rapalogs") as multimerizing agents have been disclosed (see WO96/41865). In the case of rapamycin itself, its significant biological activities, including potent immunosuppressive activity, rather severely limit its use in biological switches in certain applications, especially those in animals or animal cells which are sensitive to rapamycin. Improved rapalogs for such applications, especially rapalogs with reduced immunosuppressive activity, would be very desirable.

A large number of structural variants of rapamycin have been reported, typically arising as alternative fermentation products or from synthetic efforts to improve the compound's therapeutic index as an immunosuppressive agent. For example, the extensive literature on analogs, homologs, derivatives and other compounds related structurally to rapamycin include, among others, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. Additional historical information is presented in the background sections of U.S. Pat. Nos. 5,525,610; 5,310,903 and 5,362,718.

U.S. Pat. No. 5,527,907 is illustrative of the patent literature. That document discloses a series of compounds which were synthesized in an effort to make immunosuppressive rapalogs with reduced side effects. The compounds are disclosed via seven generic structural formulas, each followed by extensive lists (two to five or more columns of text each) setting forth possible substituents at various positions on the rapamycin ring. The document includes over 180 synthetic examples. The many structural variants of that invention were reported to be potent immunosuppressive agents.

SUMMARY OF THE INVENTION

A New Class of Rapalogs

As noted above, several decades of rather focused and competitive research in the laboratories of some of the leading pharmaceutical firms and academic institutions have created a rich literature describing a wide variety of rapalogs. As reported in that literature, each portion of the rapamycin molecule which was considered susceptible to chemical modification was in turn modified, and the resultant rapalogs evaluated for utility, usually as immunosuppressive agents.

It was against that extensive background that we made the completely unexpected discovery that led to the present invention. Briefly, while attempting to repeat the previously described replacement of the C7 methoxy group of rapamycin with an allyl or methallyl moiety and recover the desired C7-substituted rapalogs, we instead recovered the unintentionally synthesized members of a previously unknown family of rapalogs and found those compounds to possess useful and in fact quite significant biochemical properties. Reagents and conditions used for introducing the substitution at C3 may be used not just with rapamycin as the starting material, but also with a wide variety of rapalogs which can be obtained as alternative fermentation products or by synthetic modification of rapamycin. Moreover, the C3-substituted rapalogs may themselves be subjected to a wide variety of subsequent chemical modifications such as have been reported in the case of rapamycin. Thus, the discovery of our methodology for C3 substitution provides access to an entirely new and diverse family of rapalogs.

Our first novel rapalogs of this series are 3-allyl-rapamycin (R═H) and 3-methallyl-rapamycin (R=methyl):

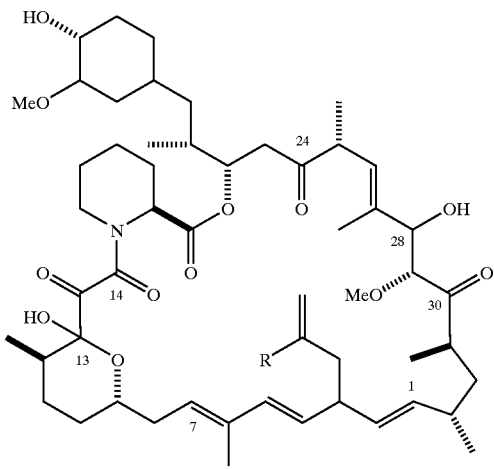

These compounds are particularly noteworthy for their ability to form a tripartite complex with FKBP12 and a genetically engineered FRB domain, or with fusion proteins containing those FKBP and FRB domains. This binding property and its significance is discussed in detail below. As mentioned above, the substitution at C3 may be combined with one or more other modifications to the rapamycin structure, numerous examples of which are known in the art. Among others, these include C3 rapalogs with (a) replacement moieties at any one or more of positions 13, 14, 20, 24, 28, and 30; (b) a prolyl moiety in place of the otherwise characteristic pipicolate moiety; and/or (c) variations on or in place of the substituted cyclohexyl ring above the pipicolate moiety as the structure is drawn above. These are disclosed in greater detail below.

These new rapalogs ("C3 rapalogs") may thus be defined as compounds which comprise the structure of Formula I:

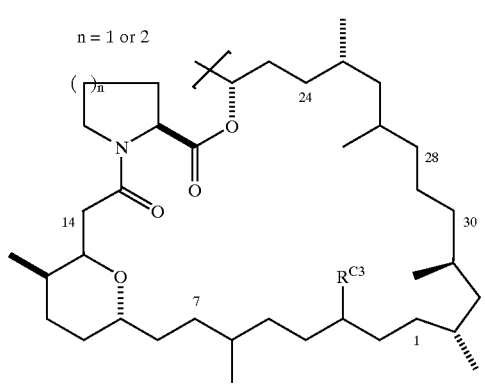

I bearing one or more optional substituents, and typically unsaturated at one or more carbon—carbon bonds spanning carbons 1 through 8, as a substantially pure stereoisomer or mixture of stereoisomers, or a pharmaceutically acceptable derivative thereof (as that term is defined below), where $R^{C3}$ is other than H. For example, in various embodiments of the invention, $R^{C3}$ is a substituted or unsubstituted aliphatic, heteroaliphatic, aromatic or heteroaromatic moiety.

C3 rapalogs useful in practicing this invention may contain substituents in any of the possible stereoisomeric orientations, and may comprise one stereoisomer substantially free of other stereoisomers (>90%, and preferably >95%, free from other stereoisomers on a molar basis) or may comprise a mixture of stereoisomers.

One preferred class of such compounds have a substantially reduced immunosuppressive effect as compared with rapamycin. By a "substantially reduced immunosuppressive effect" we mean that the rapalog has less than 0.1, preferably less than 0.01, and even more preferably, less than 0.005 times the immunosuppressive effect observed or expected with an equimolar amount of rapamycin, as measured either clinically or in an appropriate in vitro or in vivo surrogate of human immunosuppressive activity, preferably carried out on tissues of lymphoid origin, or alternatively, that the rapalog yields an EC50 value in such an in vitro assay which is at least ten times, preferably at least 100 times and more preferably at least 250 times larger than the EC50 value observed for rapamycin in the same assay.

One appropriate in vitro surrogate of immunosuppression in a human patient is inhibition of human T cell proliferation in vitro. This is a conventional assay approach that may be conducted in a number of well known variations using various human T cells or cells lines, including among others human PBLs and Jurkat cells. A rapalog may thus be assayed for human immunosuppressive activity and compared with rapamycin. A decrease in immunosuppressive activity relative to rapamycin measured in an appropriate in vitro assay is predictive of a decrease in immunosuppressive activity in humans, relative to rapamycin. Such in vitro assays may be used to evaluate the rapalog's relative immunosuppressive activity.

A variety of illustrative examples of such rapalogs are disclosed herein. This class of C3 rapalogs includes, among others, those which bind to human FKBP12, or inhibit its rotamase activity, within an order of magnitude of results obtained with rapamycin in any conventional FKBP binding or rotamase assay. One class of C3 rapalogs which is of particular interest (and is exemplified by our first two C3 rapalogs) are those compounds which comprise the structure of formula I in which $R^{C3}$ comprises:

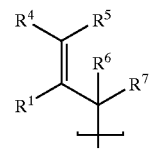

bearing one or more optional substituents, whether as a substantially pure stereoisomer or mixture of stereoisomers, or a pharmaceutically acceptable derivative thereof, where $R^1$, $R^4$, $R^5$, $R^6$ and $R^7$ are each H or a substituted or unsubstituted aliphatic, aromatic, heteroaliphatic or heteroaromatic moiety. In some embodiments the C3 substituent may comprise a cyclic moiety, e.g., where $R^1$ and $R^4$, $R^4$ and $R^5$, or $R^5$ and $R^6$ are covalently linked together to form a ring.

Another class of C3 rapalogs of particular interest are those compounds of Formula II:

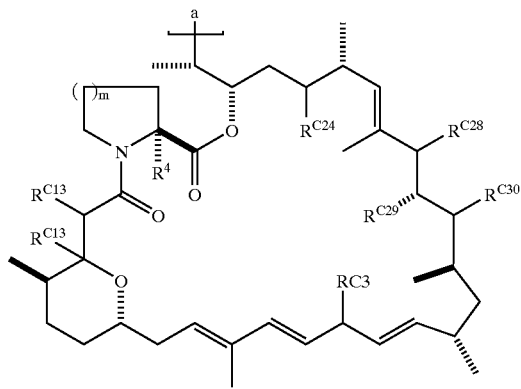

wherein $R^{C3}$ is other than H, and

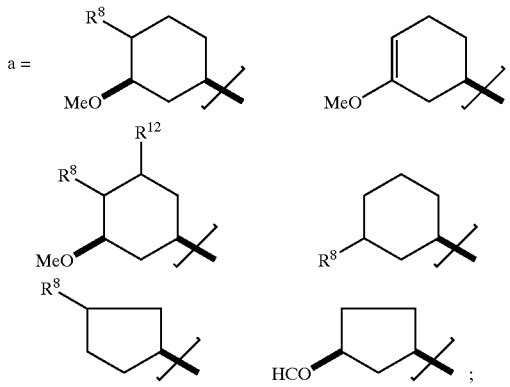

$R^{C30}$ is halo, —$OR^3$ or (=O);
$R^{C24}$ is =O, =$NR^4$=$NOR^4$, =$NNHR^4$, —$NHOR^4$, —$NHNHR^4$, —$OR^4$, —$OC(O)R^4$, —$OC(O)NR^4$, halo or —H;
$R^{C13}$ and $R^{C28}$ are independently H, halo, —$OR^3$, —$OR^5$, —$OC(O)R^5$, —$OC(O)NHR^5$, —$SR^5$, —$SC(O)R^5$, —$SC(O)NHR^5$, —$NR^5R^{5'}$ or —$N(R^5)(CO)R^{5'}$;
$R^{C14}$ is =O, —$OR^6$, —$NR^6$, —H, —$NC(O)R^6$, —$OC(O)R^6$ or —$OC(O)NR^6$;
$R^3$ is H, —$R^7$, —$C(O)R^7$ or —$C(O)NHR^7$ or a cyclic moiety (e.g., carbonate) bridging C28 and C30; and,
$R^{C29}$ is H or $OR^{11}$ (e.g., OH or OMe);

where each substituent may be present in either stereochemical orientation unless otherwise indicated, and where each occurrence of $R^1$, $R^4$, $R^5R^6$, $R^7$, $R^9$, $R^{10}$ and $R^{11}$ is independently selected from H, aliphatic, heteroaliphatic, aryl and heteroaryl; and $R^8$ is H, halo, —CN, =O, —OH, —$NR^9R^{10}$, $OSO_2CF_3$, $OSO_2F$, $OSO_2R^{4'}$, $OCOR^{4'}$, $OCONR^{4'}R^{5'}$, or $OCON(OR^{4'})R^{5'}$, as a substantially pure stereoisomer or mixture of stereoisomers, or a pharmaceutically acceptable derivative thereof.

Another class of C3 rapalogs of special interest includes those in which one or both of $R^{C13}$ and $R^{C28}$ is are independently H, halo, —$OR^3$, —$OR^5$, —$OC(O)R^5$, $OC(O)NHR^5$, —$SR^5$, —$SC(O)R^5$—$SC(O)NHR^5$, —$NR^5R^{5'}$ or —$N(R^5)(CO)R^{5'}$ where each halo moiety is independently selected from F, Cl, Br and I.

Another class of C3 rapalogs of special interest are those in which one or both of $R^{C24}$ and $R^{C30}$ are other than =O. This class includes 24, 30-tetrahydro-C3 substituted rapamycins and mono and diethers thereof and the 24-halo, 30-halo and 24,30-dihalo derivatives thereof.

Another class of C3 rapalogs which are of particular interest are rapalogs of Formula I wherein n is 1. This class of rapalogs includes rapalogs comprising a prolyl ring system in place of a pipicolate ring system.

Another class of C3 rapalogs which are of particular interest are rapalogs of Formula II wherein moiety "a" is other than

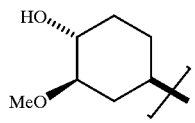

This class of rapalogs include the class of 43-epi-rapalogs in which the hydroxyl moiety at position 43 has the opposite stereochemical orientation with that shown immediately above, is a mixture of stereoisomers of the 43-hydroxyl group or contains derivatives of any of the foregoing, including ethers, esters, carbamates, halides and other derivatives of any of the foregoing position 43 rapalogs. This class further includes rapalogs in which the cyclohexyl ring is otherwise substituted and/or contains 5 ring atoms in place of the characteristic substituted cyclohexyl ring of rapamycin.

Subsets of the foregoing classes of C3 rapalogs further differ in structure from rapamycin with respect to one or more additional structural features (e.g. one or both substituents at C7, for instance), as set forth above in connection with Formula II or in connection with any of the other classes of C3 rapalogs noted herein.

Methods for Producing C3 Rapalogs

This invention further provides methods for producing C3 rapalogs which involve subjecting rapamycin or a rapalog starting material to reagents and conditions permitting replacement of the C3 hydrogen with the desire moiety. The product may be recovered from the reaction mixture, and purified from unreacted starting materials and side products. The product may be subjected to one or more additional transformations prior to final purification. Methods and materials for C3 substitution and product recovery are disclosed in detail below.

Methods for Multimerizing Chimeric Proteins

This invention further provides methods and materials for multimerizing chimeric proteins in genetically engineered cells using the new rapalogs disclosed herein, preferably while avoiding the immunosuppressive effects of rapamycin.

The genetically engineered cells contain one or more recombinant nucleic acid constructs encoding specialized chimeric proteins as described herein. Typically a first chimeric protein contains one or more FKBP domains which are capable of binding to a C3 rapalog of this invention. This first chimeric protein is also referred to herein as an "FKBP fusion protein" and further comprises at least one protein domain heterologous to at least one of its FKBP domains. The complex formed by the binding of the FKBP fusion protein to the C3 rapalog is capable of binding to a second chimeric protein which contains one or more FRB domains (the "FRB fusion protein"). The FRB fusion protein further comprises at least one protein domain heterologous to at least one of its FRB domains. In some embodiments, the FKBP fusion protein and the FRB fusion protein are different from one another. In other embodiments, however, the FKBP fusion protein is also an FRB fusion protein. In those embodiments, the chimeric protein comprises one or more FKBP domains as well as one or more FRB domains. In such cases, the first and second chimeric proteins may be the same protein, may be referred to as FKBP-FRB fusion proteins and contain at least one domain heterologous to the FKBP and/or FRB domains.

The chimeric proteins may be readily designed, based on incorporation of appropriately chosen heterologous domains, such that their multimerization triggers one or more of a wide variety of desired biological responses. The nature of the biological response triggered by rapalog-mediated complexation is determined by the choice of heterologous domains in the fusion proteins. The heterologous domains are therefore referred to as "action" or "effector" domains. The genetically engineered cells for use in practicing this invention will contain one or more recombinant nucleic acid constructs encoding the chimeric proteins, and in certain applications, will further contain one or more accessory nucleic acid constructs, such as one or more target gene constructs. Illustrative biological responses, applications of the system and types of accessory nucleic acid constructs are discussed in detail below.

A system involving related materials and methods is disclosed in WO 96/41865 (Clackson et al) and is expected to be useful in a variety of applications including, among others, research uses and therapeutic applications. That system involves the use of a multimerizing agent comprising rapamycin or a rapalog of the generic formula:

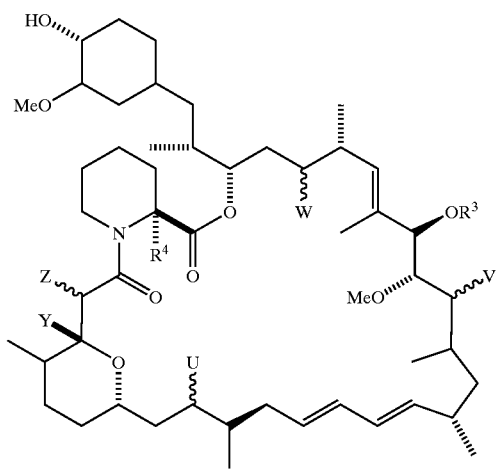

wherein U is —H, —OR$^1$, —SR$^1$, —OC(O)R$^1$, —OC(O)NHR$^1$, —NHR$^1$, —NHC(O)R$^1$, NHSO$_2$—R$^1$ or —R$^2$; R$^2$ is a substituted aryl or allyl or alkylaryl (e.g. benzyl or substituted benzyl); V is —OR$^3$ or (=O); W is =O, =NR$^4$ =NOR$^4$, =NNHR$^4$, —NHOR$^4$, —NHNHR$^4$, —OR$^4$, —OC(O)R$^4$, —OC(O)NR$^4$ or —H; Y is —OR$^5$, —OC(O)R$^5$ or —OC(O)NHR$^5$; Z is =O, —OR$^6$, —NR$^6$, —H, —NC(O)R$^6$, —OC(O)R$^6$ or —OC(O)NR$^6$; R$^3$ is H, —R$^7$, —C(O)R$^7$, —C(O)NHR$^7$ or C-28/C-30 cyclic carbonate; and R$^4$ is H or alkyl; where R$^1$, R$^4$, R$^5$, R$^6$ and R$^7$ are independently selected from H, alkyl, alkylaryl or aryl, as those terms are defined in WO 96/41865. A number of rapalogs are specifically disclosed in that document.

The subject invention is based upon a system similar to that disclosed in WO 96/41865, but involves the use of C3 rapalogs as the multimerizing agents. The subject invention thus provides a method for multimerizing chimeric proteins in cells which comprises (a) providing appropriately engineered cells containing nucleic acid constructs for directing the expression of the desired chimeric protein(s) and any desired accessory recombinant constructs, and (b) contacting the cells with a C3 rapalog or a pharmaceutically acceptable derivative thereof as described herein. The rapalog forms a complex containing itself and at least two molecules of the chimeric protein(s).

In one embodiment, at least one of the chimeric proteins contains at least one FKBP domain whose peptide sequence differs from a naturally occurring FKBP peptide sequence, e.g. the peptide sequence of human FKBP12, at up to ten amino acid residues in the peptide sequence. Preferably the number of changes in peptide sequence is limited to five, and more preferably to 1, 2, or 3. Preferably the changes are replacements rather than simple deletions or insertions. In embodiments in which the rapalog differs from rapamycin at one or more positions in addition to the modification at C3, loss of C7 methoxy and loss of triene conjugation, at least one of the chimeric proteins may contain at least one FKBP domain comprising at least one amino acid replacement relative to the sequence of a naturally occurring FKBP, especially a mammalian FKBP such as human FKBP12.

In another embodiment, at least one of the chimeric proteins contains at least one FRB domain whose peptide sequence differs from a naturally occurring FRB peptide sequence, e.g. the FRB domain of human FRAP, at up to ten amino acid residues in the peptide sequence. Preferably the number of changes in peptide sequence is limited to five, and more preferably to 1, 2, or 3. Mutations of particular interest include replacement of one or more of T2098, D2102, Y2038, F2039, K2095 of an FRB domain derived from human FRAP with independently selected replacement amino acids, e.g., A, N, H, L, or S. Also of interest are the replacement of one or more of F1975, F1976, D2039 and N2035 of an FRB domain derived from yeast TOR1, or the replacement of one or more of F1978, F1979, D2042 and N2038 of an FRB domain derived from yeast TOR2, with independently selected replacement amino acids, e.g. H, L, S, A or V.

In certain embodiments the chimeric protein(s) contain at least one modification in peptide sequence, preferably up to three modifications, relative to naturally occurring sequences, in both one or more FKBP domains and one or more FRB domains.

As mentioned previously, in the various embodiments of this invention, the chimeric protein(s) contain one or more "action" or "effector" domains which are heterologous with respect to the FKBP and/or FRB domains. Effector domains may be selected from a wide variety of protein domains including DNA binding domains, transcription activation domains, cellular localization domains and signaling domains (i.e., domains which are capable upon clustering or multimerization, of triggering cell growth, proliferation, differentiation, apoptosis, gene transcription, etc.). A variety of illustrative effector domains which may be used in practicing this invention are disclosed in the various scientific and patent documents cited herein.

For example, in certain embodiments, one fusion protein contains at least one DNA binding domain (e.g., a GAL4 or ZFHD1 DNA-binding domain) and another fusion protein contains at least one transcription activation domain (e.g., a VP16 or p65 transcription activation domain). Ligand-mediated association of the fusion proteins represents the formation of a transcription factor complex and leads to initiation of transcription of a target gene linked to a DNA sequence recognized by (i.e., capable of binding with) the DNA-binding domain on one of the fusion proteins.

In other embodiments, one fusion protein contains at least one domain capable of directing the fusion protein to a particular cellular location such as the cell membrane, nucleus, ER or other organelle or cellular component. Localization domains which target the cell membrane, for example, include domains such as a myristoylation site or a transmembrane region of a receptor protein or other membrane-spanning protein. Another fusion protein can contain a signaling domain capable, upon membrane localization and/or clustering, of activating a cellular signal transduction pathway. Examples of signaling domains include an intracellular domain of a growth factor or cytokine receptor, an apoptosis triggering domain such as the intracellular domain of FAS or TNF-R1, and domains derived from other intracellular signaling proteins such as SOS, Raf, 1ck, ZAP-70, etc. A number of signaling proteins are disclosed in PCT/US94/01617 (see e.g. pages 23–26). In still other embodiments, each of the fusion proteins contains at least one FRB domain and at least one FKBP domain, as well as one or more heterologous domains. Such fusion proteins are capable of homodimerization and triggering signaling in the presence of the rapalog. In general, domains containing peptide sequence endogenous to the host cell are preferred in applications involving whole organisms. Thus, for human gene therapy applications, domains of human origin are of particular interest.

Recombinant nucleic acid constructs encoding the fusion proteins are also provided, as are nucleic acid constructs capable of directing their expression, and vectors containing such constructs for introducing them into cells, particularly eukaryotic cells, of which yeast and animal cells are of particular interest. In view of the constituent components of the fusion proteins, the recombinant DNA molecules which encode them are capable of selectively hybridizing (a) to a DNA molecule encoding a polypeptide comprising an FRB domain or FKBP domain and (b) to a DNA molecule encoding the heterologous domain or a protein from which the heterologous protein domain was derived. DNAs are also encompassed which would be capable of so hybridizing but for the degeneracy of the genetic code.

Using nucleic acid sequences encoding the fusion proteins, nucleic acid constructs for directing their expression in eukaryotic cells, and vectors or other means for introducing such constructs into cells, especially animal cells, one may genetically engineer cells, particularly animal cells, preferably mammalian cells, and most preferably human cells, for a number of important uses. To do so, one first provides an expression vector or nucleic acid construct for directing the expression in a eukaryotic (preferably animal) cell of the desired chimeric protein(s) and then introduces the recombinant DNA into the cells in a manner permitting DNA uptake and expression of the introduced DNA in at least a portion of the cells. One may use any of the various methods and materials for introducing DNA into cells for heterologous gene expression, a variety of which are well known and/or commercially available.

One object of this invention is thus a method for multimerizing fusion proteins, such as described herein, in cells, preferably animal cells. To recap, one of the fusion proteins is capable of binding to a C3 rapalog of this invention and contains at least one FKBP domain and at least one domain heterologous thereto. The second fusion protein contains at least one FRB domain and at least one domain heterologous thereto and is capable of forming a tripartite complex with the first fusion protein and one or more molecules of the C3 rapalog. In some embodiments one or more of the heterologous domains present on one of the fusion proteins are also present on the other fusion protein, i.e., the two fusion proteins have one or more common heterologous domains. In other embodiments, each fusion protein contains one or more different heterologous domains.

The method comprises contacting appropriately engineered cells with the C3 rapalog by adding the rapalog to the culture medium in which the cells are located or administering the rapalog to the organism in which the cells are located. The cells are preferably eukaryotic cells, more preferably animal cells, and most preferably mammalian cells. Primate cells, especially human cells, are of particular interest. Administration of the C3 rapalog to a human or non-human animal may be effected using any pharmaceutically acceptable formulation and route of administration. Oral administration of a pharmaceutically acceptable composition containing the C3 rapalog together with one or more pharmaceutically acceptable carriers, buffers or other excipients is currently of greatest interest.

A specific object of this invention is a method, as otherwise described above, for inducing transcription of a target gene in a rapalog-dependent manner. The cells typically contain, in addition to recombinant DNAs encoding the two fusion proteins, a target gene construct which comprises a target gene operably linked to a DNA sequence which is responsive to the presence of a complex of the fusion proteins with rapamycin or a rapalog. The target gene construct may be recombinant, and the target gene and/or a regulatory nucleic acid sequence linked thereto may be heterologous with respect to the host cell. In certain embodiments the cells are responsive to contact with a C3 rapalog which binds to the FKBP fusion protein and participates in a complex with a FRB fusion protein with a detectable preference over binding to endogenous FKBP and/or FRB-containing proteins of the host cell.

Another specific object of this invention is a method, as otherwise described above, for inducing cell death in a rapalog-dependent manner. In such cells, at least one of the heterologous domains on at least one fusion protein, and usually two fusion proteins, is a domain such as the intracellular domain of FAS or TNF-R1, which, upon clustering, triggers apoptosis of the cell.

Another specific object of this invention is a method, as otherwise described above, for inducing cell growth, differentiation or proliferation in a rapalog-dependent manner. In such cells, at least one of the heterologous domains of at least one of the fusion proteins is a signaling domain such as, for example, the intracellular domain of a receptor for a hormone which mediates cell growth, differentiation or proliferation, or a downstream mediator of such signaling. Cell growth, differentiation and/or proliferation follows clustering of such signaling domains. Such clustering occurs in nature following hormone binding, and in engineered cells of this invention following contact with a C3 rapalog.

Cells of human origin are preferred for human gene therapy applications, although cell types of various origins (human or other species) may be used, and may, if desired, be encapsulated within a biocompatible material for use in human subjects.

Also provided are materials and methods for producing the foregoing engineered cells. This object is met by providing recombinant nucleic acids, typically DNA molecules, encoding the fusion proteins, together with any desired ancillary recombinant nucleic acids such as a target gene construct, and introducing the recombinant nucleic acids into the host cells under conditions permitting nucleic acid uptake by cells. Such transfection may be effected ex vivo, using host cells maintained in culture. Cells that are engineered in culture may subsequently be introduced into a host organism, e.g. in ex vivo gene therapy applications. Doing so thus constitutes a method for providing a host organism, preferably a human or non-human mammal, which is responsive (as described herein) to the presence of a C3 rapalog as provided herein. Alternatively transfection may be effected in vivo, using host cells present in a human or non-human host organism. In such cases, the nucleic acid molecules are introduced directly into the host organism under conditions permitting uptake of nucleic acids by one or more of the host organism's cells. This approach thus constitutes an alternative method for providing a host organism, preferably a human or non-human mammal, which is responsive (as described herein) to the presence of a C3 rapalog. Various materials and methods for the introduction of DNA and RNA into cells in culture or in whole organisms are known in the art and may be adapted for use in practicing this invention.

Other objects are achieved using the engineered cells described herein. For instance, a method is provided for multimerizing fusion proteins of this invention by contacting cells engineered as described herein with an effective amount of the C3 rapalog permitting the rapalog to form a complex with the fusion proteins. In embodiments in which multimerization of the fusion proteins triggers transcription of a target gene, this constitutes a method for activating the expression of the target gene. In embodiments in which the fusion proteins contain one or more signaling domains, this constitutes a method for activating a cellular signal transduction pathway. In specific embodiments in which the signaling domains are selected based on their ability following clustering to trigger cell growth, proliferation, differentiation or cell death, C3 rapalog-mediated clustering constitutes a method for actuating cell growth, proliferation, differentiation or cell death, as the case may be. These methods may be carried out in cell culture or in whole organisms, including human patients. In the former case, the rapamycin or rapalog is added to the culture medium. In the latter case, the rapamycin or rapalog (which may be in the form of a pharmaceutical or veterinary composition) is administered to the whole organism, e.g., orally, parenterally, etc. Preferably, the dose of the C3 rapalog administered to an animal is below the dosage level that would cause undue immunosuppression in the recipient.

Also disclosed are kits for use in the genetic engineering of cells or human or non-human animals as described herein. One such kit contains one or more recombinant nucleic acid constructs encoding fusion proteins of this invention. The recombinant nucleic acid constructs will generally be in the form of eukaryotic expression vectors suitable for introduction into animal cells and capable of directing the expression of the fusion proteins therein. Such vectors may be viral vectors as described elsewhere herein. The kit may also contain a sample of a C3 rapalog of this invention capable of forming a complex with the encoded fusion proteins. The kit may further contain a multimerization antagonist such as FK506 or some other compound capable of binding to one of the fusion proteins but incapable of forming a complex with both. In certain embodiments, the recombinant nucleic acid constructs encoding the fusion proteins will contain a cloning site in place of DNA encoding one or more of the heterologous domains, thus permitting the practitioner to introduce DNA encoding a heterologous domain of choice. In some embodiments the kit may also contain a target gene construct containing a target gene or cloning site linked to a DNA sequence responsive to the presence of the complexed fusion proteins, as described in more detail elsewhere. The kit may contain a package insert identifying the enclosed nucleic acid construct(s), and/or instructions for introducing the construct(s) into host cells or organisms.

DETAILED DESCRIPTION OF THE INVENTION

Definitions

The definitions and orienting information below will be helpful for a full understanding of this document.

FRB domains are polypeptide regions (protein "domains"), typically of at least about 89 amino acid residues, which are capable of forming a tripartite complex with an FKBP protein and rapamycin (or a C3 rapalog of this invention). FRB domains are present in a number of naturally occurring proteins, including FRAP proteins (also referred to in the literature as "RAPT1" or "RAFT") from human and other species; yeast proteins including Tor1 and Tor2; and a *Candida* FRAP homolog. Information concerning the nucleotide sequences, cloning, and other aspects of these proteins is already known in the art, permitting the synthesis or cloning of DNA encoding the desired FRB peptide sequence, e.g., using well known methods and PCR primers based on published sequences.

| protein source | reference/sequence accession numbers |
| --- | --- |
| human FRAP | Brown et al, 1994, Nature 369, 756–758; GenBank accession #L34075, NCBI Seq ID 508481; Chiu et al, 1994, PNAS USA 91, 12574–12578; Chen et al, 1995, PNAS USA 92, 4947–4951 |
| murine RAPT1 | Chiu et al, supra. |
| yeast Tor1 | Helliwell et al, 1994, Mol Cell Biol 5, 105–118; EMBL Accession #X74857, NCBI Seq Id #468738 |
| yeast Tor2 | Kunz et al, 1993, Cell 73, 585–596; EMBL Accession #X71416, NCBI Seq ID 298027 |
| Candida TOR | WO95/33052 (Berlin et al) |

FRB domains for use in this invention generally contain at least about 89–100 amino acid residues. FIG. 2 of Chiu et al, supra, displays a 160-amino acid span of human FRAP, murine FRAP, *S. cerevisiae* TOR1 and *S. cerevisiae* TOR2 encompassing the conserved FRB region. Typically the FRB sequence selected for use in fusion proteins of this invention will span at least the 89-amino acid sequence Glu-39 through Lys/Arg-127, as the sequence is numbered in that figure. For reference, using the numbering of Chen et al or Sabitini et al, the 89-amino acid sequence is numbered Glu-2025 through Lys-2113 in the case of human FRAP, Glu-1965 through Lys-2053 in the case of Tor2, and Glu-1962 through Arg-2050 in the case of Tor1. An FRB domain for use in fusion proteins of this invention will be capable of binding to a complex of an FKBP protein bound to rapamycin or a C3 rapalog of this invention (as may be determined by any means, direct or indirect, for detecting such binding, including, for example, means for detecting such binding employed in the FRAP/RAFT/RAPT and Tor-related references cited herein). The peptide sequence of such an FRB domain comprises (a) a naturally occurring peptide sequence spanning at least the indicated 89-amino acid region of the proteins noted above or corresponding regions of homologous proteins; (b) a variant of a naturally occurring FRB sequence in which up to about ten (preferably 1–5, more preferably 1–3) amino acids of the naturally-occurring peptide sequence have been deleted, inserted, or replaced with substitute amino acids; or (c) a peptide sequence encoded by a DNA sequence capable of selectively hybridizing to a DNA molecule encoding a naturally occurring FRB domain or by a DNA sequence which would be capable, but for the degeneracy of the genetic code, of selectively hybridizing to a DNA molecule encoding a naturally occurring FRB domain. A preferred FRB triple mutant is disclosed in the Experimental Examples below.

FKBPs (FK506 binding proteins) are the cytosolic receptors for macrolides such as FK506, FK520 and rapamycin and are highly conserved across species lines. For the purpose of this disclosure, FKBPs are proteins or protein domains which are capable of binding to rapamycin or to a C3 rapalog of this invention and further forming a tripartite complex with an FRB-containing protein. An FKBP domain may also be referred to as a "rapamycin binding domain". Information concerning the nucleotide sequences, cloning, and other aspects of various FKBP species is already known in the art, permitting the synthesis or cloning of DNA encoding the desired FKBP peptide sequence, e.g., using well known methods and PCR primers based on published sequences. See e.g. Staendart et al, 1990, Nature 346, 671–674 (human FKBP12); Kay, 1996, Biochem. J. 314, 361–385 (review). Homologous FKBP proteins in other mammalian species, in yeast, and in other organisms are also known in the art and may be used in the fusion proteins disclosed herein. See e.g. Kay, 1996, Biochem. J. 314, 361–385 (review). The size of FKBP domains for use in this invention varies, depending on which FKBP protein is employed. An FKBP domain of a fusion protein of this invention will be capable of binding to rapamycin or a C3 rapalog of this invention and participating in a tripartite complex with an FRB-containing protein (as may be determined by any means, direct or indirect, for detecting such binding). The peptide sequence of an FKBP domain of an FKBP fusion protein of this invention comprises (a) a naturally occurring FKBP peptide sequence, preferably derived from the human FKBP12 protein (exemplified below) or a peptide sequence derived from another human FKBP, from a murine or other mammalian FKBP, or from some other animal, yeast or fungal FKBP; (b) a variant of a naturally occurring FKBP sequence in which up to about ten (preferably 1–5, more preferably 1–3, and in some embodiments just one) amino acids of the naturally-occurring peptide sequence have been deleted, inserted, or replaced with substitute amino acids; or (c) a peptide sequence encoded by a DNA sequence capable of selectively hybridizing to a DNA molecule encoding a naturally occurring FKBP or by a DNA sequence which would be capable, but for the degeneracy of the genetic code, of selectively hybridizing to a DNA molecule encoding a naturally occurring FKBP.

"Capable of selectively hybridizing" as that phrase is used herein means that two DNA molecules are susceptible to hybridization with one another, despite the presence of other DNA molecules, under hybridization conditions which can be chosen or readily determined empirically by the practitioner of ordinary skill in this art. Such treatments include conditions of high stringency such as washing extensively with buffers containing 0.2 to 6×SSC, and/or containing 0.1% to 1% SDS, at temperatures ranging from room temperature to 65–750 C. See for example F. M. Ausubel et al., Eds, Short Protocols in Molecular Biology, Units 6.3 and 6.4 (John Wiley and Sons, New York, 3d Edition, 1995).

The terms "protein", "polypeptide" and "peptide" are used interchangeably herein.

"Nucleic acid constructs", as that term is used herein, denote nucleic acids (usually DNA, but also encompassing RNA, e.g. in a retroviral delivery system) used in the practice of this invention which are generally recombinant, as that term is defined below, and which may exist in free form (i.e., not covalently linked to other nucleic acid sequence) or may be present within a larger molecule such as a DNA vector, retroviral or other viral vector or a chromosome of a genetically engineered host cell. Nucleic acid constructs of particular interest are those which encode fusion proteins of this invention or which comprise a target gene and expression control elements. The construct may further include nucleic acid portions comprising one or more of the following elements relevant to regulation of transcription, translation, and/or other processing of the coding region or gene product thereof: transcriptional promoter and/or enhancer sequences, a ribosome binding site, introns, etc.

"Recombinant", "chimeric" and "fusion", as those terms are used herein, denote materials comprising various component domains, sequences or other components which are mutually heterologous in the sense that they do not occur together in the same arrangement, in nature. More specifically, the component portions are not found in the same continuous polypeptide or nucleotide sequence or molecule in nature, at least not in the same cells or order or orientation or with the same spacing present in the chimeric protein or recombinant DNA molecule of this invention.

"Transcription control element" denotes a regulatory DNA sequence, such as initiation signals, enhancers, and promoters, which induce or control transcription of protein coding sequences with which they are operably linked. The term "enhancer" is intended to include regulatory elements capable of increasing, stimulating, or enhancing transcription from a promoter. Such transcription regulatory components can be present upstream of a coding region, or in certain cases (e.g. enhancers), in other locations as well, such as in introns, exons, coding regions, and 3' flanking sequences.

"Dimerization", "oligomerization" and "multimerization" are used interchangeably herein and refer to the association or clustering of two or more protein molecules, mediated by the binding of a drug to at least one of the proteins. In preferred embodiments, the multimerization is mediated by the binding of two or more such protein molecules to a common divalent or multivalent drug. The formation of a complex comprising two or more protein molecules, each of which containing one or more FKBP domains, together with one or more molecules of an FKBP ligand which is at least divalent (e.g. FK1012 or AP1510) is an example of such association or clustering. In cases where at least one of the proteins contains more than one drug binding domain, e.g., where at least one of the proteins contains three FKBP domains, the presence of a divalent drug leads to the clustering of more than two protein molecules. Embodiments in which the drug is more than divalent (e.g. trivalent) in its ability to bind to proteins bearing drug binding domains also can result in clustering of more than two protein molecules. The formation of a tripartite complex comprising a protein containing at least one FRB domain, a protein containing at least one FKBP domain and a molecule of rapamycin is another example of such protein clustering. In certain embodiments of this invention, fusion proteins contain multiple FRB and/or FKBP domains. Complexes of such proteins may contain more than one molecule of rapamycin or a derivative thereof or other dimerizing agent and more than one copy of one or more of the constituent proteins. Again, such multimeric complexes are still referred to herein as tripartite complexes to indicate the presence of the three types of constituent molecules, even if one or more are represented by multiple copies. The formation of complexes containing at least one divalent drug and at least two protein molecules, each of which contains at least one drug binding domain, may be referred to as "oligomerization" or "multimerization", or simply as "dimerization", "clustering" or "association".

"Dimerizer" denotes a C3 rapalog of this invention which brings together two or more proteins in a multimeric complex.

"Activate" as applied herein to the expression or transcription of a gene denotes a directly or indirectly observable increase in the production of a gene product.

"Genetically engineered cells" denotes cells which have been modified ("transduced") by the introduction of recombinant or heterologous nucleic acids (e.g. one or more DNA constructs or their RNA counterparts) and further includes the progeny of such cells which retain part or all of such genetic modification.

A "therapeutically effective dose" of a C3 rapalog of this invention denotes a treatment- or prophylaxis-effective dose, e.g., a dose which yields detectable target gene transcription or cell growth, proliferation, differentiation, death, etc. in the genetically engineered cell, or a dose which is predicted to be treatment- or prophylaxis-effective by extrapolation from data obtained in animal or cell culture models. A therapeutically effective dose is usually preferred for the treatment of a human or non-human mammal.

This invention involves methods and materials for multimerizing chimeric proteins in genetically engineered cells using C3 rapalogs. The design and implementation of various dimerization-based biological switches has been reported, inter alia, in Spencer et al and in various international patent applications cited herein. Other accounts of successful application of this general approach have also been reported. Chimeric proteins containing an FRB domain fused to an effector domain has also been disclosed in Rivera et al, 1996, Nature Medicine 2, 1028–1032 and in WO 96/41865 (Clackson et al) and WO 95/33052 (Berlin et al). As noted previously, the fusion proteins are designed such that association of the effector domains, through ligand-mediated "dimerization" or "multimerization" of the fusion proteins which contain them, triggers a desired biological event such as transcription of a desired gene, cell death, cell proliferation, etc. For example, clustering of chimeric proteins containing an action domain derived from the intracellular portion of the T cell receptor CD3 zeta domain triggers transcription of a gene under the transcriptional control of the IL-2 promoter or promoter elements derived therefrom. In other embodiments, the action domain comprises a domain derived from the intracellular portion of a protein such as FAS or the TNFalpha receptor (TNFalpha-R1), which are capable, upon oligomerization, of triggering apoptosis of the cell. In still other embodiments, the action domains comprise a DNA-binding domain such as GAL4 or ZFHD1 and a transcription activation domain such as VP16 or p65, paired such that oligomerization of the chimeric proteins represents assembly of a transcription factor complex which triggers transcription of a gene linked to a DNA sequence recognized by (capable of specific binding interaction with) the DNA binding domain.

Chimeric proteins containing one or more ligand-binding domains and one or more action domains, e.g. for activation of transcription of a target gene, triggering cell death or other signal transduction pathway, cellular localization, etc., are disclosed in PCT/US94/01617, PCT/US94/08008 and Spencer et al, supra. The design and use of such chimeric proteins for ligand-mediated gene-knock out and for ligand-mediated blockade of gene expression or inhibition of gene product function are disclosed in PCT/US95/10591. Novel DNA binding domains and DNA sequences to which they bind which are useful in embodiments involving regulated transcription of a target gene are disclosed, e.g., in Pomeranz et al, 1995, Science 267:93–96. Those references provide substantial information, guidance and examples relating to the design, construction and use of DNA constructs encoding analogous chimeras, target gene constructs, and other aspects which may also be useful to the practitioner of the subject invention.

By appropriate choice of chimeric proteins, this invention permits one to activate the transcription of a desired gene; actuate cell growth, proliferation, differentiation or apoptosis; or trigger other biological events in engineered cells in a rapalog-dependent manner analogous to the systems described in the patent documents and other references cited above. The engineered cells, preferably animal cells, may be growing or maintained in culture or may be present within whole organisms, as in the case of human gene therapy, transgenic animals, and other such applications. The rapalog is administered to the cell culture or to the organism containing the engineered cells, as the case may be, in an amount effective to multimerize the FKBP fusion proteins and FRB fusion proteins (as may be observed indirectly by monitoring target gene transcription, apoptosis or other biological process so triggered). In the case of administration to whole organisms, the rapalog may be administered in a composition containing the rapalog and one or more acceptable veterinary or pharmaceutical diluents and/or excipients.

A compound which binds to one of the chimeric proteins but does not form tripartite complexes with both chimeric proteins may be used as a multimerization antagonist. As such it may be administered to the engineered cells, or to organisms containing them (preferably in a composition as described above in the case of administration to whole animals), in an amount effective for blocking or reversing the effect of the rapalog, i.e. for preventing, inhibiting or disrupting multimerization of the chimeras. For instance, FK506, FK520 or any of the many synthetic FKBP ligands which do not form tripartite complexes with FKBP and FRAP may be used as an antagonist.

One important aspect of this invention provides materials and methods for rapalog-dependent, direct activation of transcription of a desired gene. In one such embodiment, a set of two or more different chimeric proteins, and corresponding DNA constructs capable of directing their expression, is provided. One such chimeric protein contains as its action domain(s) one or more transcriptional activation domains. The other chimeric protein contains as its action domain(s) one or more DNA-binding domains. A rapalog of this invention is capable of binding to both chimeras to form a dimeric or multimeric complex thus containing at least one DNA binding domain and at least one transcriptional activating domain. Formation of such complexes leads to activation of transcription of a target gene linked to, and under the transcriptional control of, a DNA sequence to which the DNA-binding domain is capable of binding, as can be observed by monitoring directly or indirectly the presence or concentration of the target gene product.

Preferably the DNA binding domain, and a chimera containing it, binds to its recognized DNA sequence with sufficient selectivity so that binding to the selected DNA sequence can be observed (directly or indirectly) despite the presence of other, often numerous other, DNA sequences. Preferably, binding of the chimera comprising the DNA-binding domain to the selected DNA sequence is at least two, more preferably three and even more preferably more than four orders of magnitude greater than binding to any one alternative DNA sequence, as measured by in vitro binding studies or by measuring relative rates or levels of transcription of genes associated with the selected DNA sequence as compared with any alternative DNA sequences.

Cells which have been genetically engineered to contain such a set of constructs, together with any desired accessory constructs, may be used in applications involving ligand-mediated, regulated actuation of the desired biological event, be it regulated transcription of a desired gene, regulated triggering of a signal transduction pathway such as the triggering of apoptosis, or another event. Cells engineered for regulatable expression of a target gene, for instance, can be used for regulated production of a desired protein (or other gene product) encoded by the target gene. Such cells may be grown in culture by conventional means. Addition of the rapalog to the culture medium containing the cells leads to expression of the target gene by the cells and production of the protein encoded by that gene. Expression of the gene and production of the protein can be turned off by withholding further multimerization agent from the media, by removing residual multimerization agent from the media, or by adding to the medium a multimerization antagonist reagent.

Engineered cells of this invention can also be produced and/or used in vivo, to modify whole organisms, preferably animals, especially humans, e.g. such that the cells produce a desired protein or other result within the animal containing them. Such uses include gene therapy applications.

Embodiments involving regulatable actuation of apoptosis provide engineered cells susceptible to rapalog-inducible cell death. Such engineered cells can be eliminated from a cell culture or host organism after they have served their intended purposed (e.g. production of a desired protein or other product), if they have or develop unwanted properties, or if they are no longer useful, safe or desired. Elimination is effected by adding the rapalog to the medium or administering it to the host organism. In such cases, the action domains of the chimeras are protein domains such as the intracellular domains of FAS or TNF-R1, downstream components of their signaling pathways or other protein domains which upon oligomerization trigger apoptosis.

This invention thus provides materials and methods for achieving a biological effect in cells in response to the addition of a rapalog of this invention. The method involves providing cells engineered as described herein and exposing the cells to the rapalog.

For example, this invention provides a method for activating transcription of a target gene in cells. The method involves providing cells containing (a) DNA constructs encoding a set of chimeric proteins of this invention capable upon rapalog-mediated multimerization of initiating transcription of a target gene and (b) a target gene linked to an associated cognate DNA sequence responsive to the multimerization event (e.g. a DNA sequence recognized, i.e., capable of binding with, a DNA-binding domain of a foregoing chimeric protein. The method involves exposing the cells to a rapalog capable of binding to the chimeric proteins in an amount effective to result in expression of the target gene. In cases in which the cells are growing in culture, exposing the cells to the rapalog may be effected by adding the rapalog to the culture medium. In cases in which the cells are present within a host organism, exposing them to the rapalog is effected by administering the rapalog to the host organism. For instance, in cases in which the host organism is a human or non-human, the rapalog may be administered to the host organism by oral, bucal, sublingual, transdermal, subcutaneous, intramuscular, intravenous, intra-joint or inhalation administration in an appropriate vehicle therefor. Again, depending on the design of the constructs for the chimeric proteins and of any accessory constructs, the rapalog-mediated biological event may be activation of a cellular function such as signal transduction leading to cell growth, cell proliferation, gene transcription, or apoptosis; deletion of a gene of interest, blockade of expression of a gene of interest, or inhibition of function of a gene product of interest; direct transcription of a gene of interest; etc.

This invention further encompasses a pharmaceutical composition comprising a rapalog of this invention in admixture with a pharmaceutically acceptable carrier and optionally with one or more pharmaceutically acceptable excipients. Such pharmaceutical compositions can be used to promote multimerization of chimeras of this invention in engineered cells in whole animals, e.g. in human gene therapy applications to achieve any of the objectives disclosed herein.

Said differently, this invention provides a method for achieving any of those objectives, e.g. activation of transcription of a target gene (typically a heterologous gene for a therapeutic protein), cell growth or proliferation, cell death or some other selected biological event, in an animal, preferably a human patient, in need thereof and containing engineered cells of this invention. That method involves administering to the animal a pharmaceutical composition containing the rapalog by a route of administration and in an amount effective to cause multimerization of the chimeric proteins in at least a portion of the engineered cells. Multimerization may be detected indirectly by detecting the occurrence of target gene expression; cell growth, proliferation or death; or other objective for which the chimeras were designed and the cells genetically engineered.

This invention further encompasses a pharmaceutical composition comprising a multimerization antagonist of this invention in admixture with a pharmaceutically acceptable carrier and optionally with one or more pharmaceutically acceptable excipients for inhibiting or otherwise reducing, in whole or part, the extent of multimerization of chimeric proteins in engineered cells of this invention in a subject, and thus for de-activating the transcription of a target gene, for example, or turning off another biological result of this invention. Thus, the use of the multimerizing rapalogs and of the multimerization antagonist reagents to prepare pharmaceutical compositions and achieve their pharmacologic results is encompassed by this invention.

Also disclosed is a method for providing a host organism, preferably an animal, typically a non-human mammal or a human subject, responsive to a rapalog of this invention. The method involves introducing into the organism cells which have been engineered in accordance with this invention, i.e. containing one or more nucleic acid constructs encoding the chimeric proteins, and so forth. The engineered cells may be encapsulated using any of a variety of materials and methods before being introduced into the host organism. Alternatively, one can introduce the nucleic acid constructs of this invention into a host organism, e.g. a mammal, under conditions permitting incorporation thereof into one or more cells of the host mammal, e.g. using viral vectors, introduction of DNA by injection or via catheter, etc.

Also provided are kits for producing cells responsive to a rapalog of this invention. One such kit contains one or more nucleic acid constructs encoding and capable of directing the expression of chimeras which, upon rapalog-mediated oligomerization, trigger the desired biological response. The kit may contain a quantity of a rapalog capable of multimerizing the chimeric protein molecules encoded by the construct(s) of the kit, and may contain in addition a quantity of a multimerization antagonist. The kit may further contain a nucleic acid construct encoding a target gene (or cloning site) linked to a cognate DNA sequence which is recognized by the dimerized chimeric proteins permitting transcription of a gene linked to that cognate DNA sequence in the presence of multimerized chimeric protein molecules. The constructs may be associated with one or more selection markers for convenient selection of transfectants, as well as other conventional vector elements useful for replication in prokaryotes, for expression in eukaryotes, and the like. The selection markers may be the same or different for each different construct, permitting the selection of cells which contain each such construct(s).

The accessory construct for introducing into cells a target gene in association with a cognate DNA sequence may contain a cloning site in place of a target gene. A kit containing such a construct permits the engineering of cells for regulatable expression of a gene to be provided by the practitioner.

Other kits of this invention may contain one or two (or more) nucleic acid constructs for chimeric proteins in which one or more contain a cloning site in place of the transcriptional activator or DNA binding protein, permitting the user to insert whichever such domain s/he wishes. Such a kit may optionally include other elements as described above, e.g. a nucleic construct for a target gene with or without a cognate DNA sequence for a pre-selected DNA binding domain.

Any of the kits may also contain positive control cells which were stably transformed with constructs of this invention such that they express a reporter gene (for CAT, SEAP, beta-galactosidase or any conveniently detectable gene product) in response to exposure of the cells to the rapalog. Reagents for detecting and/or quantifying the expression of the reporter gene may also be provided.

For further information and guidance on the design, construction and use of such systems or components thereof which may be adapted for use in practicing the subject invention, reference to the following publications is suggested: Spencer et al, 1993, supra; Rivera et al, 1996, supra; Spencer et al, 1996, Current Biology 6, 839–847; Luo et al, 1996, Nature, 383, 181–185; Ho et al, 1996, Nature 382, 822–826; Belshaw et al, 1996, Proc. Natl. Acad. Sci. USA 93, 4604–4607; Spencer, 1996, TIG 12 (5), 181–187; Spencer et al, 1995, Proc., Natl. Acad. Sci. USA 92, 9805–9809; Holsinger et al, 1995, Proc. Natl. Acad. Sci. USA 92, 9810–9814; Pruschy et al, 1994, Chemistry & Biology 1 (3), 163–172; and published international patent applications WO 94/18317, WO 95/02684, WO 95/33052, WO 96/20951, WO 96/41865 and WO 98/02441, the contents of each of which is incorporated herein by reference.

A key focus of the subject invention is the use of C3 rapalogs as mediators of protein—protein interactions in applications using FKBP and FRB fusion proteins such as described above and elsewhere herein. The C3 rapalogs may be used in the various applications of the underlying dimerization-based technology, including triggering biological events in genetically engineered cells grown or maintained in culture or present in whole organisms, including humans and other mammals. The C3 rapalogs may thus be useful as research reagents in biological experiments in vitro, in experiments conducted on animals containing the genetically engineered cells, and as prophylactic or therapeutic agents in animal and human health care in subjects containing genetically engineered cells.

Rapalogs, C3 Rapalogs and Pharmaceutically Acceptable Derivatives Thereof

"Rapalogs" as that term is used herein denotes a class of compounds comprising the various analogs, homologs and derivatives of rapamycin and other compounds related structurally to rapamycin.

Rapalogs include, among others, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and elimination, derivatization or replacement of one or more substituents of the cyclohexyl ring or replacement of the cyclohexyl ring with a substituted or unsubstituted cyclopentyl ring. Rapalogs, as that term is used herein, do not include rapamycin itself, and preferably do not contain an oxygen bridge between C1 and C30. Illustrative examples of rapalogs are disclosed in the documents listed in Table I.

TABLE I

| | | | | |
|---|---|---|---|---|
| WO9710502 | WO9418207 | WO9304680 | U.S. Pat. No. 5527907 | U.S. Pat. No. 5225403 |
| WO9641807 | WO9410843 | WO9214737 | U.S. Pat. No. 5484799 | U.S. Pat. No. 5221625 |
| WO9635423 | WO9409010 | WO9205179 | U.S. Pat. No. 5457194 | U.S. Pat. No. 5210030 |
| WO9603430 | WO94/04540 | U.S. Pat. No. 5604234 | U.S. Pat. No. 5457182 | U.S. Pat. No. 5208241 |
| WO9600282 | WO9402485 | U.S. Pat. No. 5597715 | U.S. Pat. No. 5362735 | U.S. Pat. No. 5200411 |
| WO9516691 | WO9402137 | U.S. Pat. No. 5583139 | U.S. Pat. No. 5324644 | U.S. Pat. No. 5198421 |
| WO9515328 | WO9402136 | U.S. Pat. No. 5563172 | U.S. Pat. No. 5318895 | U.S. Pat. No. 5147877 |
| WO9507468 | WO9325533 | U.S. Pat. No. 5561228 | U.S. Pat. No. 5310903 | U.S. Pat. No. 5140018 |
| WO9504738 | WO9318043 | U.S. Pat. No. 5561137 | U.S. Pat. No. 5310901 | U.S. Pat. No. 5116756 |
| WO9504060 | WO9313663 | U.S. Pat. No. 5541193 | U.S. Pat. No. 5258389 | U.S. Pat. No. 5109112 |
| WO9425022 | WO9311130 | U.S. Pat. No. 5541189 | U.S. Pat. No. 5252732 | U.S. Pat. No. 5093338 |
| WO9421644 | WO9310122 | U.S. Pat. No. 5534632 | U.S. Pat. No. 5247076 | U.S. Pat. No. 5091389 |

Other illustrative rapalogs include those depicted in Table II:
TABLE II
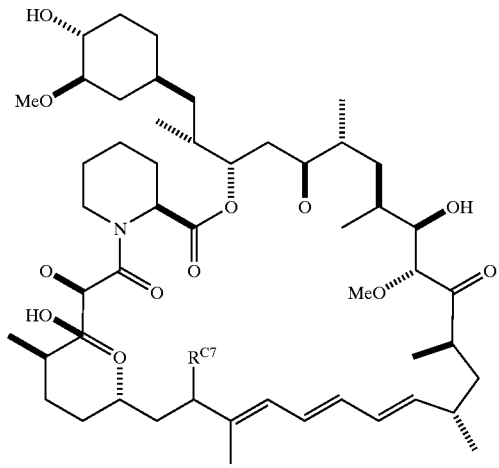
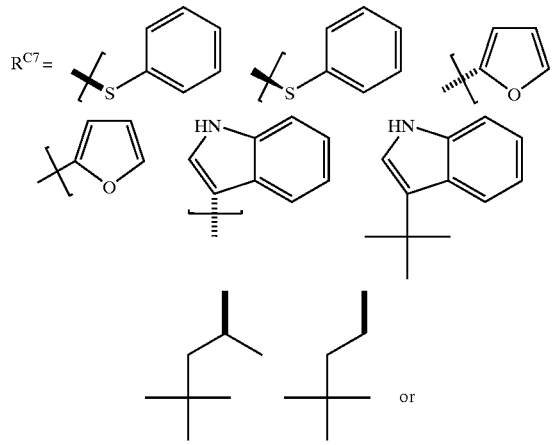
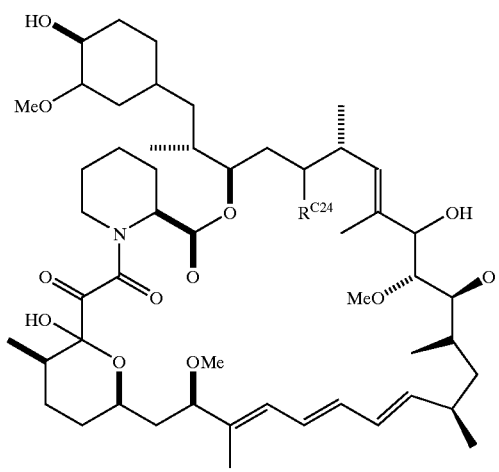
TABLE II-continued
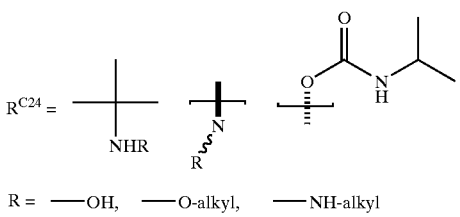
R = —OH, —O-alkyl, —NH-alkyl
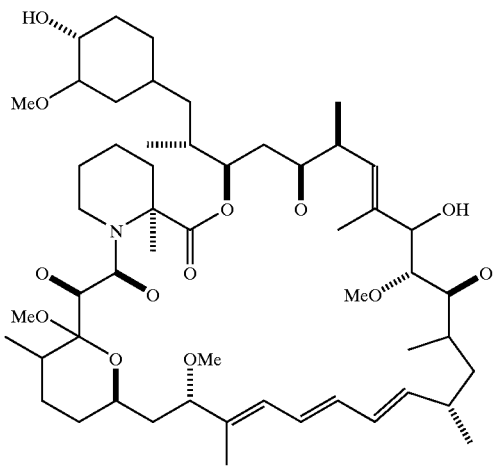
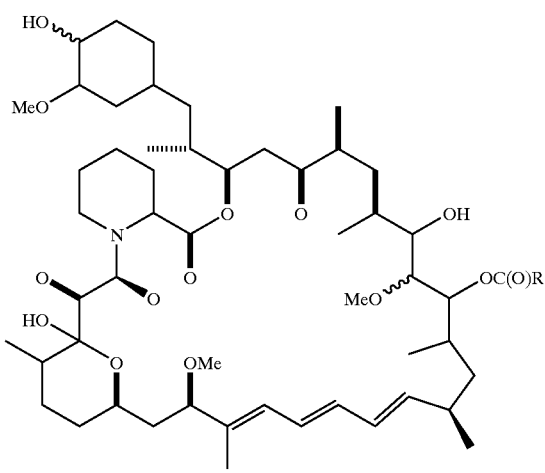
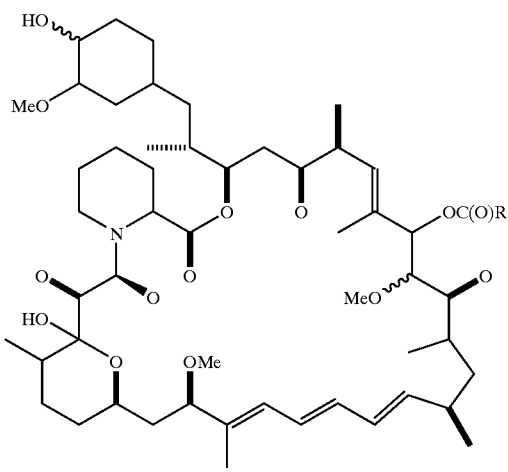

TABLE II-continued
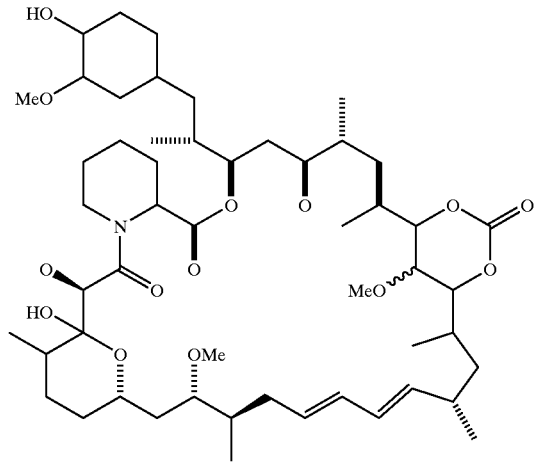
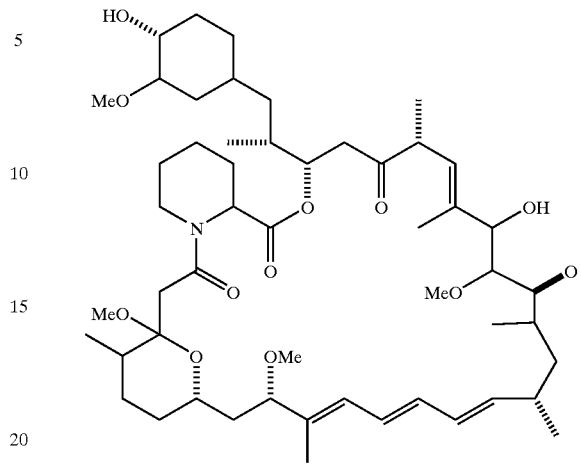
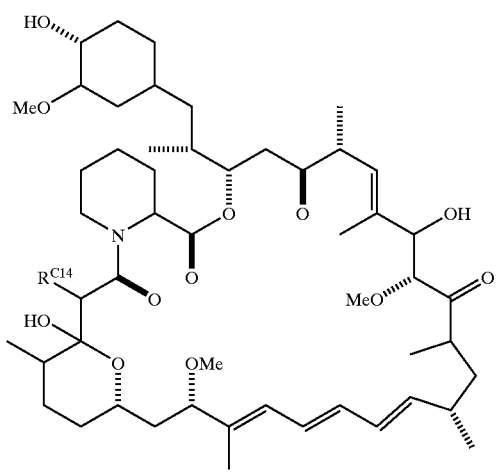
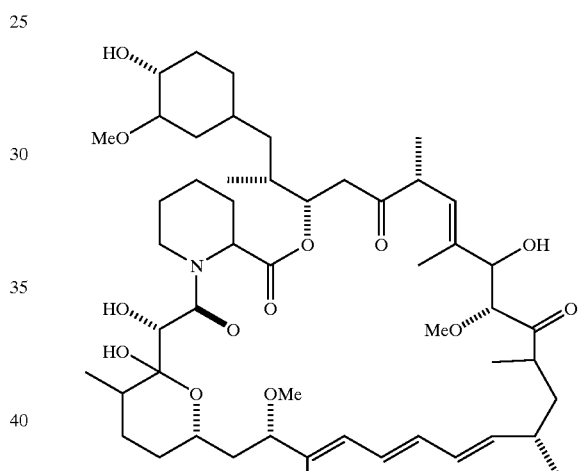
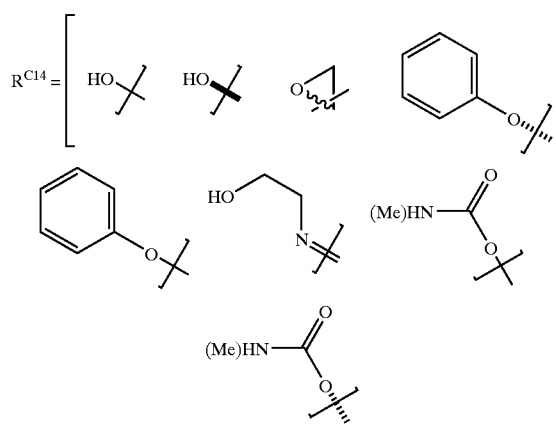
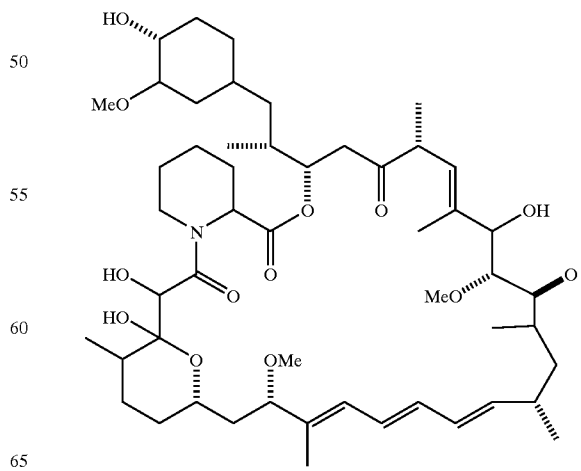

TABLE II-continued

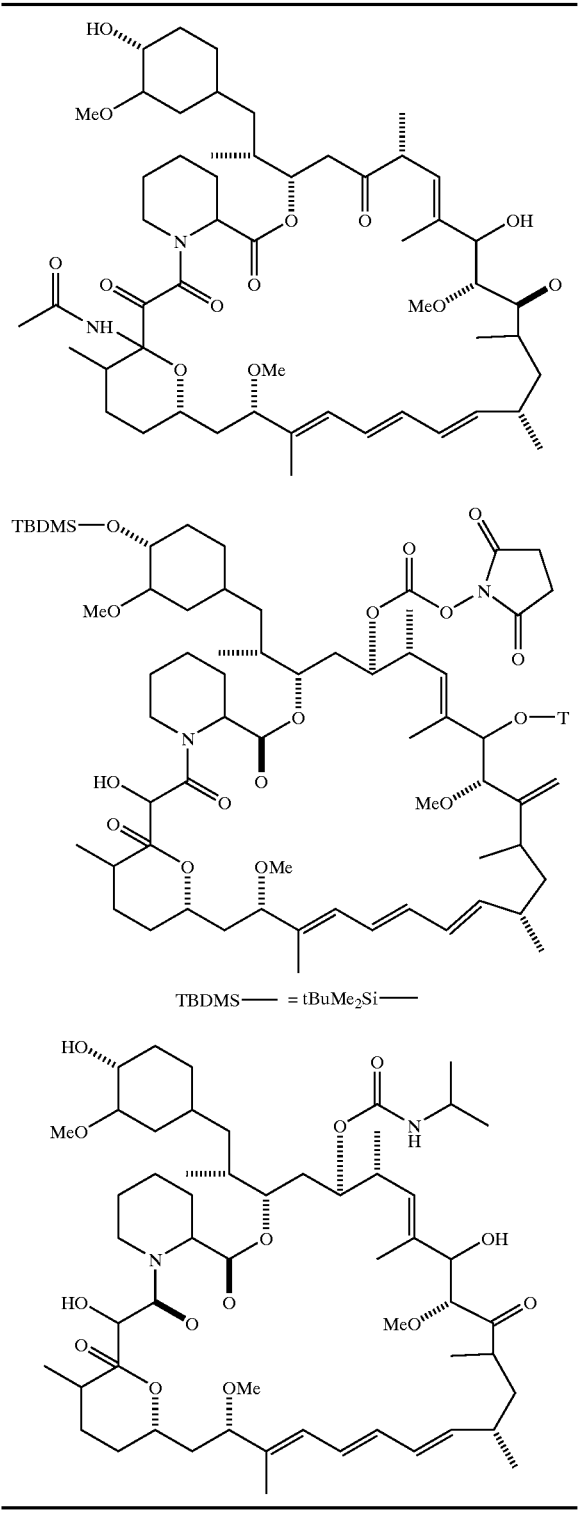

"C3 Rapalogs" are defined above with reference to Formula I and are exemplified by the various classes and subsets of compounds disclosed herein.

The phrase "pharmaceutically acceptable derivative" denotes any pharmaceutically acceptable salt, ester, or salt of such ester, of a C3 rapalog, or any other adduct or derivative which, upon administration to a patient, is capable of providing (directly or indirectly) a C3 rapalog as described herein, or a metabolite or residue thereof. Pharmaceutically acceptable derivatives thus include among others pro-drugs of the rapalogs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Various pro-drugs of rapamycin and of other compounds, and materials and methods for derivatizing the parent compounds to create the pro-drugs, are known and may be adapted to the present invention.

The term "aliphatic" as used herein includes both saturated and unsaturated, straight chain (i.e., unbranched), branched, cyclic, or polycyclic aliphatic hydrocarbons, which are optionally substituted with one or more functional groups. Unless otherwise specified, alkyl, other aliphatic, alkoxy and acyl groups preferably contain 1–8, and in many cases 1–6, contiguous aliphatic carbon atoms. Illustrative aliphatic groups thus include, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents.

Examples of substituents include: —OH, —$OR^{2'}$, —SH, —$SR^{2'}$, —CHO, =O, —COOH (or ester, carbamate, urea, oxime or carbonate thereof), —$NH_2$ (or substituted amine, amide, urea, carbamate or guanidino derivative therof), halo, trihaloalkyl, cyano, —$SO_2$—$CF_3$, —$OSO_2F$, —$OS(O)_2R^{11}$, —$SO_2$—$NHR^{11}$, —$NHSO_2$—$R^{11}$, sulfate, sulfonate, aryl and heteroaryl moieties. Aryl and heteroaryl substituents may themselves be substituted or unsubstituted (e.g. mono-, di- and tri-alkoxyphenyl; methylenedioxyphenyl or ethylenedioxyphenyl; halophenyl; or -phenyl-C(Me)2-$CH_2$—O—CO—[C3–C6] alkyl or alkylamino).

The term "aliphatic" is thus intended to include alkyl, alkenyl, alkynyl, cycloalkyl, cycloalkenyl, and cycloalkynyl moieties.

As used herein, the term "alkyl" includes both straight, branched and cyclic alkyl groups. An analogous convention applies to other generic terms such as "alkenyl", "alkynyl" and the like. Furthermore, as used herein, the language "alkyl", "alkenyl", "alkynyl" and the like encompasses both substituted and unsubstituted groups.

The term "alkyl" refers to groups usually having one to eight, preferably one to six carbon atoms. For example, "alkyl" may refer to methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, and the like. Suitable substituted alkyls include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl and the like.

The term "alkenyl" refers to groups usually having two to eight, preferably two to six carbon atoms. For example, "alkenyl" may refer to prop-2-enyl, but-2-enyl, but-3-enyl, 2-methylprop-2-enyl, hex-2-enyl, hex-5-enyl, 2,3-dimethylbut-2-enyl, and the like. The language "alkynyl," which also refers to groups having two to eight, preferably two to six carbons, includes, but is not limited to, prop-2-ynyl, but-2-ynyl, but-3-ynyl, pent-2-ynyl, 3-methylpent-4-ynyl, hex-2-ynyl, hex-5-ynyl, and the like.

The term "cycloalkyl" as used herein refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic or heteroaliphatic or heterocyclic moieties, may optionally be substituted.

The term "heteroaliphatic" as used herein refers to aliphatic moieties which contain one or more oxygen, sulfur, nitrogen, phosphorous or silicon atoms, e.g., in place of carbon atoms. Heteroaliphatic moieties may be branched, unbranched or cyclic and include heterocycles such as morpholino, pyrrolidinyl, etc.

The term "heterocycle" as used herein refers to cyclic heteroaliphatic groups and preferably three to ten ring atoms total, includes, but is not limited to, oxetane, tetrahydrofuranyl, tetrahydropyranyl, aziridine, azetidine, pyrrolidine, piperidine, morpholine, piperazine and the like.

The terms "aryl" and "heteroaryl" as used herein refer to stable mono- or polycyclic, heterocyclic, polycyclic, and polyheterocyclic unsaturated moieties having 3–14 carbon atoms which may be substituted or unsubstituted. Substituents include any of the previously mentioned substituents. Non-limiting examples of useful aryl ring groups include phenyl, halophenyl, alkoxyphenyl, dialkoxyphenyl, trialkoxyphenyl, alkylenedioxyphenyl, naphthyl, phenanthryl, anthryl, phenanthro and the like. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like (see e.g. Katritzky, Handbook of Heterocyclic Chemistry). The aryl or heteroaryl moieties may be substituted with one to five members selected from the group consisting of hydroxy, C1–C8 alkoxy, C1–C8 branched or straight-chain alkyl, acyloxy, carbamoyl, amino, N-acylamino, nitro, halo, trihalomethyl, cyano, and carboxyl. Aryl moieties thus include, e.g. phenyl; substituted phenyl bearing one or more substituents selected from groups including: halo such as chloro or fluoro, hydroxy, C1–C6 alkyl, acyl, acyloxy, C1–C6 alkoxy (such as methoxy or ethoxy, including among others dialkoxyphenyl moieties such as 2,3-, 2,4-, 2,5-, 3,4- or 3,5-dimethoxy or diethoxy phenyl or such as methylenedioxyphenyl, or 3-methoxy-5-ethoxyphenyl; or trisubstituted phenyl, such as trialkoxy (e.g., 3,4,5-trimethoxy or ethoxyphenyl), 3,5-dimethoxy-4-chloro-phenyl, etc.), amino, —$SO_2NH_2$, —$SO_2NH$(aliphatic), —$SO_2N$(aliphatic)$_2$, —O-aliphatic-COOH, and —O-aliphatic-$NH_2$ (which may contain one or two N-aliphatic or N-acyl substituents).

A "halo" substituent according to the present invention may be a fluoro, chloro, bromo or iodo substituent. Fluoro is often the preferred halogen.

C3 rapalogs may further differ from rapamycin, in addition to the modification at C3, with respect to no, one, two, three, four, five, six or seven substituent moieties. This class includes among others rapalogs with modifications, relative to rapamycin, at C3 and C13; C3 and C14; C3 and $a$; C3 and C43; C3 and C24; C3 and C28; C3 and C30; C3, C13 and C14; C3, C13 and $a$; C3, C13 and C43; C3, C13 and C24; C3, C13 and C28; C3, C13 and C30; C3, C14 and a; C3, C14 and C43; C3, C14 and C24; C3, C14 and C28; C3, C14 and C30; C3, $a$ and C24; C3, $a$ and C28; C3, $a$ and C30; C3, C24 and C30; C3, C24, C30 and $a$; C3, C24, C30 and C13; C3, C24, C30 and C14; and C3, C24, C30, C13 and $a$.

One subset of C3 rapalogs of interest in the practice of the various methods of the invention are C3 rapalogs in which $R^{C30}$ and $R^{C24}$ are both other than (=O). In certain embodiments of this subset, $R^{C30}$ and $R^{C24}$ are both —OH, e.g. in the "S" configuration. In other embodiments $R^{C30}$ and $R^{C24}$ are independently selected from $OR^3$. This subset includes among others rapalogs which further differ from rapamycin with respect to the moiety a. For instance, this subset includes compounds of Formula III:

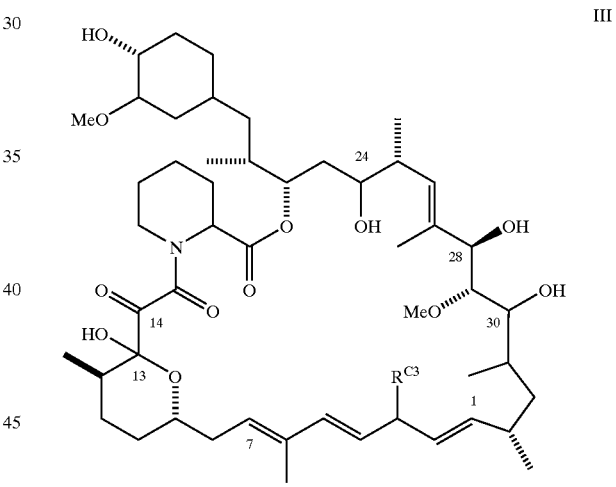

III where $R^{C3}$ is other than —H. Alternative substituents for $R^{C3}$ are as disclosed elsewhere herein. Other compounds within this subset include those in which one, two, three, four or five of the hydroxyl groups is epimerized, fluorinated, alkylated, acylated or otherwise modified via other ester, carbamate, carbonate or urea formation. Illustrative additional compounds for example are those compounds otherwise as shown in formula III except that the hydroxyl group at C43 is in the opposite stereochemical orientation and/or the hydroxyl groups at C28 and C30 are alkylated, acylated or linked via carbonate formation.

Another subset of C3 rapalogs of special interest are those in which one or both of $R^{C13}$ and $R^{C28}$ is F. In various embodiments of this subset, one, two, three, four or five other substituents in formula II differ from the substituents found in rapamycin. For instance, this subset includes C13 fluoro-C3-rapalogs, C28 fluoro-C3-rapalogs and C13, C28-difluoro-C3-rapalogs.

Another subset of C3 rapalogs of special interest are those in which $R^{C14}$ is other than O, OH or H, e.g., C3 rapalogs in which $R^{C14}$ is —$OR^6$, —$NR^6$, $NC(O)R^6$, —$OC(O)R^6$ or —$OC(O)NR^6$, with or without one or more other modifications relative to rapamycin.

Another subset of C3 rapalogs of interest are those in which $R^{C24}$ is other than =O, again, with or without one or more other modifications at other positions relative to rapamycin.

Another subset of C3 rapalogs which is of special interest in practicing the methods of this invention include those which share the stereoisomerism of rapamycin and in which $R^{C7a}$ is —OMe wherein $R^{C30}$ is not =O, $R^{C24}$ is not =O, $R^{C13}$ is not —OH, $R^{C14}$ is not =O and/or $R^3$ and/or $R^4$ are not H.

Other C3 rapalogs of interest include those in which $R^{C14}$ is OH.

Furthermore, this invention encompasses C3 rapalogs in which one or more of the carbon—carbon double bonds at the 1,2, 3, 4 or 5,6 positions in rapamycin are saturated, alone or in combination with a modification elsewhere in the molecule, e.g. at one or more of C13, C43, C24 C28 and/or C30. It should also be appreciated that the C3,C4 double bond may be epoxidized; that the C6 methyl group may be replaced with —$CH_2OH$ or —$CH_2OMe$; that the C43 hydroxy may be converted to F, Cl or H or other substituent; and that the C42 methoxy moiety may be demethylated, in any of the compounds disclosed herein, using methods known in the art. Likewise, moiety "a" may be replaced with any of the following

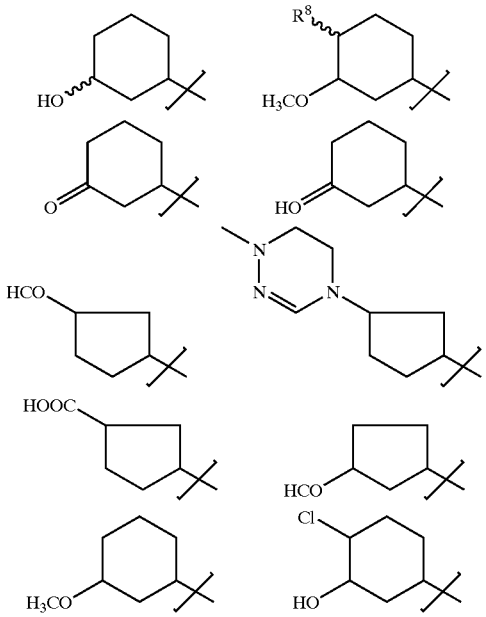

Synthetic Guidance

The production of rapamycin by fermentation and by total synthesis is known. The production of a number of rapalogs (other than C3 rapalogs) by fermentation or synthetic modification of fermentation products is also known. These include among others rapalogs bearing alternative moieties to the characteristic cyclohexyl ring or pipecolate ring of rapamycin, as well as C29-desmethyl-rapamycin and C29-desmethoxyrapamycin and a variety of other rapalogs such as are disclosed herein.

Rapamycin may be converted into a C3 rapalog using silyl ethers as disclosed in the experimental examples which follow.

The C3 rapalogs can be produced using a variety of techniques. These techniques can be synthetic processes involving nucleophilic reagents and catalysts. A first rapalog can be treated with a nucleophilic reagent under conditions which allow for the formation of the desired C3 rapalog. The first rapalog can be a C7 modified rapalog, e.g. C7-methoxy rapalog. These conditions include such factors as type of nucleophilic reagent, type of catalysts and selection of purification technique used to isolate or purify the final C3 rapalog.

For example, substituted rapalogs of the invention can be prepared by treating a rapalog having a substituent attached to the macrocyclic ring, e.g., at the C7 position, with a nucleophilic reagent, e.g., a silyl ether, in the presence of a catalyst. In another embodiment, rapamycin can be converted into C3 rapalogs using silyl enol ethers known to those skilled in the art.

Suitable substituent include those recognized in the art by skilled artisans and include halogens, tosylates, mesylates, esters and alkoxides, and preferably lower alkyl alkoxides. It was discovered that treatment of rapalogs having a substituent at the C7 position with suitable nucleophiles formed a rapalog modified at the C3 position by the nucleophile.

Suitable nucleophilic reagents include those recognized in the art by skilled artisans and include silyl ethers, silyl enol ethers, grignard reagents, enolates, carbanions and the like. A preferred nucleophilic reagent is a silyl ether, preferably trialkylsilylethers, particularly substituted and unsubstituted allyl groups, e.g., methallyltrialkylsilylether.

The term "silyl ether" is art recognized and is intended to include those compounds having the formula RC3-SiRR'R" (2) wherein R, R' and R" are aliphatic, aromatic, heteroaliphatic or heteroaromatic moieties and RC3 is as defined above, preferably a substituted or unsubstituted allyl moiety. Moreover, silyl ethers are commercially available and can be purchased from chemical supply companies such as ALDRICH®, and SIGMA®.

The term "silyl enol ether" is art recognized and is intended to include those compounds having the formula

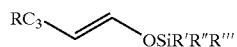

wherein R, R' and R" are aliphatic, aromatic, heteroaliphatic or heteroaromatic moieties and RC3 is as defined above. Silyl enol ethers are also commercially available and can be purchased from chemical supply companies such as ALDRICH®, and SIGMA®.

Suitable catalysts include Lewis acid catalysts such as $AlCl_3$, $ZnCl_2$, p-toluene sulfonic acid, and preferably $BF_3$ etherate.

The following reaction scheme depicted below provides an example of nucleophilic displacement of a leaving group by a nucleophilic reagent, e.g., a silyl ether. Treatment of compound 1, a rapalog,

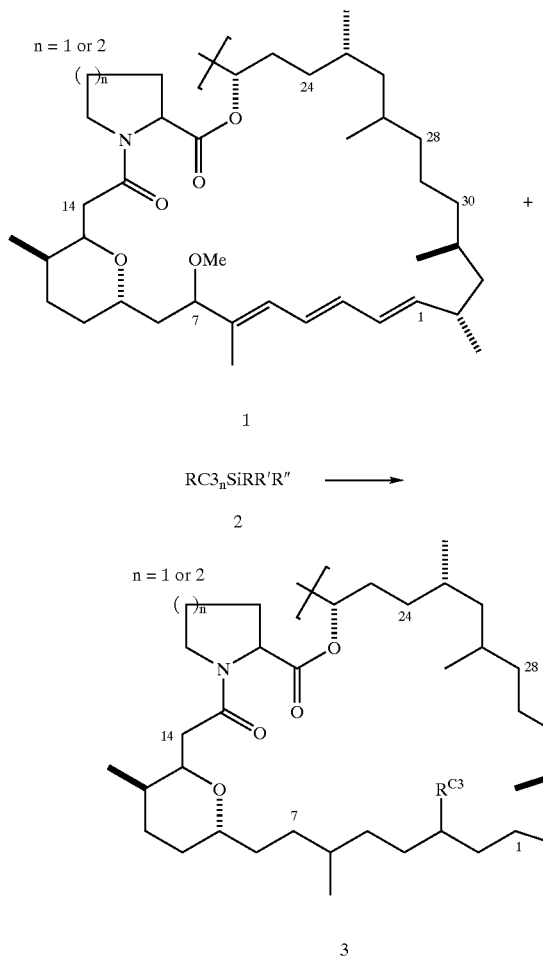

with silyl ether, 2, under conditions which permit the formation of a compound having formula 3 include combining a C7 heteroatom bearing rapalog, e.g., OMe, with a trialkylsilylether in the presence of a catalyst, preferably $BF_3$/etherate. In general, the reaction conditions are performed at ambient temperature or below, preferably at about $-40°$ C.

C3 rapalogs comprising additional modifications with respect to the structure of rapamycin may be prepared analogously, starting with the corresponding rapalog in place of rapamycin. Alternatively, one or more additional transformations may be carried out on a C3 rapalog intermediate.

Methods and materials for effecting various chemical transformations of rapamycin and structurally related macrolides are known in the art, as are methods for obtaining rapamycin and various rapalogs by fermentation. Many such chemical transformations of rapamycin and various rapalogs are disclosed in the patent documents identified in Table I, above, which serve to illustrate the level of skill and knowledge in the art of chemical synthesis and product recovery, purification and formulation which may be applied in practicing the subject invention. The following representative transformations and/or references which can be employed to produce the desired rapalogs are illustrative:

| ring position modified | literature reference |
|---|---|
| C-13 | C13->F: protect C28 and C43, rxn at 0° C. |
| C-14 | Schubert, et al. Angew Chem Int Ed Engl 23, 167 (1984). |
| C-20 | Nelson, U.S. Pat. No. 5,387,680 |
| C-24 | U.S. Pat. No. 5,373,014; 5,378,836 Lane, et al. Synthesis 1975, p136. |
| C-30 | Luengo et al. Tet. Lett. 35, 6469 (1994) |
| various positions | Or et al, U.S. Pat. Nos. 5,527,907 and 5,583,139 Luengo, WO 94/02136; Cottens et al, WO 95/16691 WO 98/02441 (Holt et al) |

Additionally, it is contemplated that rapalogs for use in this invention as well as intermediates for the production of such rapalogs may be prepared by directed biosynthesis, e.g. as described by Katz et al, WO 93/13663 and by Cane et al, WO 9702358.

Novel rapalogs of this invention may be prepared by one of ordinary skill in this art relying upon methods and materials known in the art as guided by the disclosure presented herein. For instance, methods and materials may be adapted from known methods set forth or referenced in the documents cited above, the full contents of which are incorporated herein by reference. Additional guidance and examples are provided herein by way of illustration and further guidance to the practitioner. It should be understood that the chemist of ordinary skill in this art would be readily able to make modifications to the foregoing, e.g. to add appropriate protecting groups to sensitive moieties during synthesis, followed by removal of the protecting groups when no longer needed or desired, and would be readily capable of determining other synthetic approaches.

Purification of mixtures of rapalogs isolated from the above described conditions can be accomplished using a technique which allows for the isolation or recovery of the desired C3 rapalog, e.g., a desired purity or in a desired form, e.g., substantially free of C7 rapalog. An example of such a technique is the recycling HPLC technique described in the examples below. Use of recycling HPLC lead to the discovery, under the conditions described above, that nucleophiles add to the C3 position with concomitant displacement of a C7 group to yield C3 rapalogs. Structural confirmation that the rapalogs were functionalized at the C3 position was determined by mass spectral analysis and/or NMR spectroscopy.

As a non-limiting example, an unpurified reaction mixture of rapalog products can be eluted through an HPLC column and recycled back through the column to increase separation of components and thus, purity of the final isolates. HPLC systems are known to those skilled in the art can be adapted to include such recycling features. Generally, the eluant and the component(s) are recycled until a desired separation of components and purity is achieved, e.g., 15 to 20 cycles. One skilled in the art can determine how many cycles are required, the solvent(s) required, the type of column, etc. to achieve the purity desired.

For example, a polystyrene size exclusion column can be used. The polystyrene column can be functionalized, e.g., contains hydroxyl functionality, to facilitate separation of component. In one particularly preferred embodiment, a JAIGEL GS-310 column can be used to effect separation of components.

One aspect of the invention pertains to the purity of the isolated rapalogs. Purity of the isolate rapalogs can be determined by techniques known to those skilled in the art and include mass spectrometry, $^1$H NMR and $^{13}$C NMR. In one embodiment, the isolated C3 rapalogs or the invention are substantially free contaminants, e.g., substantially free of C7 rapalogs. One example of determining the purity of the isolated C3 rapalog is by $^1$H NMR. The purity of the compound can be determined by analyzing the peak height ratio of the desired product to that of contaminants. In one embodiment, the ratio is at least about 5:1 (product/contaminant). In another embodiment, the ratio is at least about 10:1, more preferably 50:1, most preferably 100:1 with the most preferred being that no contaminants are detected by NMR.

In another aspect, purity of the isolated rapalog can be determined by $^1$H NMR by analyzing the ratio between the peak heights associated with those groups attached at the C7 position of the starting material to that of the peak heights associated with the groups attached at the C3 position in the resultant product. The purity of the C3 rapalog can be determined by analyzing the peak height ratio of the desired product to that of peaks associated with the starting material containing a C7 group. In one embodiment, the ratio is at least about 5:1 (isolated C3 rapalog product/C7 starting material). In another embodiment, the ratio is at least about 10:1, more preferably 50:1, most preferably 100:1 with the most preferred being that no contaminants are detected by NMR.

In another embodiment, the isolated C3 rapalog is at least about 90% pure, as determined by analytical techniques known in the art, e.g. capillary gas chromatography, analytical HPLC, etc. In a more preferred embodiment, the isolated C3 rapalog is at least about 95% pure. In another embodiment, the isolated C3 rapalog is at least about 98% pure. In a most preferred embodiment, the isolated C3 rapalog is about 100% pure.

FKBP Domains and Fusion Proteins

The FKBP fusion protein comprises at least one FKBP domain containing all or part of the peptide sequence of an FKBP domain and at least one heterologous action domain. This chimeric protein must be capable of binding to a C3 rapalog of this invention, preferably with a Kd value below about 100 nM, more preferably below about 10 nM and even more preferably below about 1 nM, as measured by direct binding measurement (e.g. fluorescence quenching), competition binding measurement (e.g. versus FK506), inhibition of FKBP enzyme activity (rotamase), or other assay methodology. Typically the chimeric protein will contain one or more protein domains comprising peptide sequence selected from that of a naturally occurring FKBP protein such as human FKBP12, e.g. as described in International Patent Application PCT/US94/01617. That peptide sequence may be modified to adjust the binding specificity, usually with replacement, insertion or deletion of 10 or fewer, preferably 5 or fewer, amino acid residues. Such modifications are elected in certain embodiments to yield one or both of the following binding profiles: (a) binding of a C3 rapalog to the modified FKBP domain, or chimera containing it, preferably at least one, and more preferably at least two, and even more preferably three or four or more, orders of magnitude better (by any measure) than to FKBP12 or the FKBP endogenous to the host cells to be engineered; and (b) binding of the FKBP:rapalog complex to the FRB fusion protein, preferably at least one, and more preferably at least two, and even more preferably at least three, orders of magnitude better (by any measure) than to the FRAP or other FRB-containing protein endogenous to the host cell to be engineered.

The FKBP chimera also contains at least one heterologous action domain, i.e., a protein domain containing non-FKBP peptide sequence. The action domain may be a DNA-binding domain, transcription activation domain, cellular localization domain, intracellular signal transduction domain, etc., e.g. as described elsewhere herein or in PCT/US94/01617 or the other cited references. Generally speaking, the action domain is capable of directing the chimeric protein to a selected cellular location or of initiating a biological effect upon association or aggregation with another action domain, for instance, upon multimerization of proteins containing the same or different action domains.

A recombinant nucleic acid encoding such a fusion protein will be capable of selectively hybridizing to a DNA encoding the parent FKBP protein, e.g. human FKBP 12, or would be capable of such hybridization but for the degeneracy of the genetic code. Since these chimeric proteins contain an action domain derived from another protein, e.g. Gal4, VP16, FAS, CD3 zeta chain, etc., the recombinant DNA encoding the chimeric protein will also be capable of selectively hybridizing to a DNA encoding that other protein, or would be capable of such hybridization but for the degeneracy of the genetic code.

FKBP fusion proteins of this invention, as well as FRB fusion proteins discussed in further detail below, may contain one or more copies of one or more different ligand binding domains and one or more copies of one or more action domains. The ligand binding domain(s) (i.e., FKBP and FRB domains) may be N-terminal, C-terminal, or interspersed with respect to the action domain(s). Embodiments involving multiple copies of a ligand binding domain usually have 2, 3 or 4 such copies. For example, an FKBP fusion protein may contain 2, 3 or 4 FKBP domains. The various domains of the FKBP fusion proteins (and of the FRB fusion proteins discussed below) are optionally separated by linking peptide regions which may be derived from one of the adjacent domains or may be heterologous.

Illustrative examples of FKBP fusion proteins useful in the practice of this invention include the FKBP fusion proteins disclosed in PCT/US94/01617 (Stanford & Harvard), PCT/US94/08008 (Stanford & Harvard), Spencer et al (supra), PCT/US95/10591 (ARIAD), PCT/US95/06722 (Mitotix, Inc.) and other references cited herein; the FKBP fusion proteins disclosed in the examples which follow; variants of any of the foregoing FKBP fusion proteins which contain up to 10 (preferably 1–5) amino acid insertions, deletions or substitutions in one or more of the FKBP domains and which are still capable of binding to rapamycin or to a rapalog; variants of any of the foregoing FKBP fusion proteins which contain one or more copies of an FKBP domain which is encoded by a DNA sequence capable of selectively hybridizing to a DNA sequence encoding a naturally occurring FKBP domain and which are still capable of binding to rapamycin or to a rapalog; variants of any of the foregoing in which one or more heterologous action domains are deleted, replaced or supplemented with a different heterologous action domain; variants of any of the foregoing FKBP fusion proteins which are capable of binding to rapamycin or a rapalog and which contain an FKBP domain derived from a non-human source; and variants of any of the foregoing FKBP fusion proteins which contain one or more amino acid residues corresponding to Tyr26, Phe36, Asp37, Arg42, Phe46, Phe48, Glu54, Val55, or Phe99 of human FKBP12 in which one or more of those amino acid residues is replaced by a different amino acid, the variant being capable of binding to rapamycin or a rapalog.

For instance, in a number of cases the FKBP fusion proteins comprise multiple copies of an FKBP domain containing amino acids 1–107 of human FKBP12, separated by the 2-amino acid linker Thr-Arg encoded by ACTAGA, the ligation product of DNAs digested respectively with the restriction endonucleases SpeI and XbaI. The following table provides illustrative subsets of mutant FKBP domains based on the foregoing FKBP12 sequence:

| Illustrative Mutant FKBPs | | | |
|---|---|---|---|
| F36A | Y26V | F46A | W59A |
| F36V | Y26S | F48H | H87W |
| F36M | D37A | F48L | H87R |
| F36S | I90A | F48A | F36V/F99A |
| F99A | I91A | E54A | F36V/F99G |
| F99G | F46H | E54K | F36M/F99A |
| Y26A | F46L | V55A | F36M/F99G | note:
Entries identify the native amino acid by single letter code and sequence position, followed by the replacement amino acid in the mutant. Thus, F36V designates a human FKBP12 sequence in which phenylalanine at position 36 is replaced by valine. F36V/F99A indicates a double mutation in which phenylalanine at positions 36 and 99 are replaced by valine and alanine, respectively.

FRB Domains and Fusion Proteins

The FRB fusion protein comprises at least one FRB domain (which may comprise all or part of the peptide sequence of a FRAP protein or a variant thereof, as described elsewhere) and at least one heterologous effector domain.

Generally speaking, the FRB domain, or a chimeric protein encompassing it, is encoded by a DNA molecule capable of hybridizing selectively to a DNA molecule encoding a protein comprising a naturally occurring FRB domain, e.g. a DNA molecule encoding a human or other mammalian FRAP protein or one of yeast proteins, Tor-1 or Tor-2 or the previously mentioned *Candida* FRB-containing protein. FRB domains of this invention include those which are capable of binding to a complex of an FKBP protein and a C3 rapalog of this invention.

The FRB fusion protein must be capable of binding to the complex formed by the FKBP fusion protein with a C3 rapalog of this invention. Preferably, the FRB fusion protein binds to that complex with a Kd value below 200 μM, more preferably below 10 μM, as measured by conventional methods. The FRB domain will be of sufficient length and composition to maintain high affinity for a complex of the rapalog with the FKBP fusion protein. In some embodiments the FRB domain spans fewer than about 150 amino acids in length, and in some cases fewer than about 100 amino acids. One such region comprises a 133 amino acid region of human FRAP extending from Val2012 through Tyr2144. See Chiu et al, 1994, Proc. Natl. Acad. Sci. USA 91:12574–12578. An FRB region of particular interest spans Glu2025 through Gln2114 of human FRAP and retains affinity for a FKBP12-rapamycin complex or for FKBP-rapalog complex. In some embodiments Q2214 is removed from the 90-amino acid sequence rendering this an 89-amino acid FRB domain. The FRB peptide sequence may be modified to adjust the binding specificity, usually with replacement, insertion or deletion, of 10 or fewer, preferably 5 or fewer, amino acids. Such modifications are elected in certain embodiments to achieve a preference towards formation of the complex comprising one or more molecules of the FKBP fusion protein, FRB fusion protein and a C3 rapalog over formation of complexes of endogenous FKBP and FRAP proteins with the rapalog. Preferably that preference is at least one, and more preferably at least two, and even more preferably three, orders of magnitude (by any measure).

A recombinant DNA encoding such a protein will be capable of selectively hybridizing to a DNA encoding a FRAP species, or would be capable of such hybridization but for the degeneracy of the genetic code. Again, since these chimeric proteins contain an effector domain derived from another protein, e.g. Gal4, VP 16, Fas, CD3 zeta chain, etc., the recombinant DNA encoding the chimeric protein will be capable of selectively hybridizing to a DNA encoding that other protein, or would be capable of such hybridization but for the degeneracy of the genetic code.

Illustrative examples of FRB chimeras useful in the practice of this invention include those disclosed in the examples which follow, variants thereof in which one or more of the heterologous domains are replaced with alternative heterologous domains or supplemented with one or more additional heterologous domains, variants in which one or more of the FRB domains is a domain of non-human peptide sequence origin (such as Tor 2 or *Candida* for example), and variants in which the FRB domain is modified by amino acid substitution, replacement or insertion as described herein, so long as the chimera is capable of binding to a complex formed by an FKBP protein and a C3 rapalog of this invention. An illustrative FRB fusion protein contains one or more FRBs of at least 89-amino acids, containing a sequence spanning at least residues 2025–2113 of human FRAP, separated by the linker Thr-Arg formed by ligation of SpeI-XbaI sites as mentioned previously. It should be appreciated that such restriction sites or linkers in any of the fusion proteins of this invention may be deleted, replaced or extended using conventional techniques such as site-directed mutagenesis.

Mixed Chimeric Proteins

A third type of chimeric protein comprises one or more FKBP domains, one or more heterologous effector domains, and one or more FRB domains as described for the FRB fusion proteins.

Mixed chimeric protein molecules are capable of forming homodimeric or homomultimeric protein complexes in the presence of a C3 rapalog to which they bind. Embodiments involving mixed chimeras have the advantage of requiring the introduction into cells of a single recombinant nucleic acid construct in place of two recombinant nucleic acid constructs otherwise required to direct the expression of both an FKBP fusion protein and a FRB fusion protein.

A recombinant DNA encoding a mixed chimeric protein will be capable of selectively hybridizing to a DNA encoding an FKBP protein, a DNA encoding FRAP, and a heterologous DNA sequence encoding the protein from which one or more effector domains is derived (e.g. Gal4, VP16, Fas, CD3 zeta chain, etc.), or would be capable of such hybridization but for the degeneracy of the genetic code.

Heterologous Domains

As mentioned above, the heterologous effector domains of the FKBP and FRB fusion proteins are protein domains which, upon mutual association of the chimeric proteins bearing them, are capable of triggering (or inhibiting) DNA-binding and/or transcription of a target gene; actuating cell growth, differentiation, proliferation or apoptosis; directing proteins to a particular cellular location; or actuating other biological events.

Embodiments involving regulatable gene transcription involve the use of target gene constructs which comprise a target gene (which encodes a polypeptide, antisense RNA, ribozyme, etc. of interest) under the transcriptional control of a DNA element responsive to the association or multimerization of the heterologous domains of the 1st and 2d chimeric proteins.

In embodiments of the invention involving direct activation of transcription, the heterologous domains of the 1 st and 2d chimeric proteins comprise a DNA binding domain such as Gal4 or a chimeric DNA binding domain such as ZFHD1, discussed below, and a transcriptional activating domain such as those derived from VP16 or p65, respectively. The multimerization of a chimeric protein containing such a transcriptional activating domain to a chimeric protein containing a DNA binding domain targets the transcriptional activator to the promoter element to which the DNA binding domain binds, and thus activates the transcription of a target gene linked to that promoter element. Foregoing the transcription activation domain or substituting a repressor domain (see PCT/US94/01617) in place of a transcription activation domain provides an analogous chimera useful for inhibiting transcription of a target gene. Composite DNA binding domains and DNA sequences to which they bind are disclosed in Pomerantz et al, 1995, supra, the contents of which are incorporated herein by reference. Such composite DNA binding domains may be used as DNA binding domains in the practice of this invention, together with a target gene construct containing the cognate DNA sequences to which the composite DBD binds.

In embodiments involving indirect activation of transcription, the heterologous domains of the chimeras are effector domains of signaling proteins which upon aggregation or multimerization trigger the activation of transcription under the control of a responsive promoter. For example, the signaling domain may be the intracellular domain of the zeta subunit of the T cell receptor, which upon aggregation, triggers transcription of a gene linked to the IL-2 promoter or a derivative thereof (e.g. iterated NF-AT binding sites).

In another aspect of the invention, the heterologous domains are protein domains which upon mutual association are capable of triggering cell death. Examples of such domains are the intracellular domains of the Fas antigen or of the TNF R1. Chimeric proteins containing a Fas domain can be designed and prepared by analogy to the disclosure of PCT/US94/01617.

Engineered Receptor Domains

As noted previously, the FKBP and FRB domains may contain peptide sequence selected from the peptide sequences of naturally occurring FKBP and FRB domains. Naturally occurring sequences include those of human FKBP12 and the FRB domain of human FRAP. Alternatively, the peptide sequences may be derived from such naturally occurring peptide sequences but contain generally up to 10, and preferably 1–5, mutations in one or both such peptide sequences. As disclosed in greater detail elsewhere herein, such mutations can confer a number of important features. For instance, an FKBP domain may be modified such that it is capable of binding a C3 rapalog preferentially, i.e. at least one, preferably two, and even more preferably three or four or more orders of magnitude more effectively, with respect to rapalog binding by the unmodified FKBP domain. An FRB domain may be modified such that it is capable of binding a (modified or unmodified) FKBP:rapalog complex preferentially, i.e. at least one, preferably two, and even more preferably three orders of magnitude more effectively, with respect to the unmodified FRB domain. FKBP and FRB domains may be modified such that they are capable of forming a tripartite complex with a C3 rapalog, preferentially, i.e. at least one, preferably two, and even more preferably three orders of magnitude more effectively, with respect to unmodified FKBP and FRB domains.

(a) FKBP

Methods for identifying FKBP mutations that confer enhanced ability to bind derivatives of FK506 containing various substituents ("bumps") were disclosed in PCT/US94/01617. Similar strategies can be used to obtain modified FKBPs that preferentially bind bumped rapamycin derivatives, i.e., rapalogs. The structure of the complex between rapamycin and FKBP12 is known (see for example Van Duyne et al., J. Am. Chem. Soc. (1991) 113, 7433–7434). Such data can be used to reveal amino acid residues that would clash with various rapalog substituents. In this approach, molecular modeling is used to identify candidate amino acid substitutions in the FKBP domain that would accommodate the rapalog substituent(s), and site-directed mutagenesis may then be used to engineer the protein mutations so identified. The mutants are expressed by standard methods and their binding affinity for the rapalogs measured, for example by inhibition of rotamase activity, or by competition for binding with a molecule such as FK506, if the mutant retains appropriate activity/affinity.

More particularly, not to be bound by theory, we contemplate that certain C3 rapalogs of this invention, e.g. rapalogs with modifications relative to rapamycin at C-13 or C-14 bind preferentially to FKBPs in which one or more of the residues, Tyr26, Phe36, Asp37, Tyr82 and Phe99, are substituted with amino acids that have smaller side chains (such as Gly, Ala, Val, Met and Ser). Examples of mutant FKBPs with modifications at positions 26 or 36 are noted in the "Illustrative Mutant FKBPs" table above. Similarly, we contemplate that rapalogs with modifications at C20 (i.e., rapalogs in which R4 is other than —H) bind preferentially to FKBPs in which Tyr82 and/or Ile56 are replaced by other amino acids, especially those with smaller side chains. In a further example, we contemplate that rapalogs bearing modifications at C24 (i.e., in which W is other than =O) bind preferentially to FKBPs in which one or more of Phe46, Phe48 and Val55 are replaced by other amino acids, again especially those with smaller side chains. Moreover, we envisage that rapalogs with modifications at C28 and/or C30 (i.e., in which R3 is other than H and/or V is other than =O) bind preferentially to FKBPs in which Glu54 is replaced by another amino acid, especially one with a smaller side chain. In all of the above examples, single or multiple amino acid substitutions may be made. Again, specific examples are noted in the previous table.

An alternative to iterative engineering and testing of single or multiple mutants is to co-randomize structurally-identified residues that are or would be in contact with or near one or more rapalog or rapamycin substituents. A collection of polypeptides containing FKBP domains randomized at the identified positions (such as are noted in the foregoing paragraph) is prepared e.g. using conventional synthetic or genetic methods. Such a collection represents a set of FKBP domains containing replacement amino acids at one or more of such positions. The collection is screened and FKBP variants are selected which possess the desired rapalog binding properties. In general, randomizing several residues simultaneously is expected to yield compensating mutants of higher affinity and specificity for a given bumped rapalog as it maximizes the likelihood of beneficial cooperative interactions between sidechains. Techniques for preparing libraries randomized at discrete positions are known and include primer-directed mutagenesis using degenerate oligonucleotides, PCR with degenerate oligonucleotides, and cassette mutagenesis with degenerate oligonucleotides (see for example Lowman, H. B, and Wells, J. A. Methods: Comp. Methods Enzymol. 1991. 3, 205–216; Dennis, M. S. and Lazarus, R. A. 1994. J. Biol. Chem. 269, 22129–22136; and references therein).

We further contemplate that in many cases, randomization of only the few residues in or near direct contact with a given position in rapamycin may not completely explore all the possible variations in FKBP conformation that could optimally accommodate a rapalog substituent (bump). Thus the construction is also envisaged of unbiased libraries containing random substitutions that are not based on structural considerations, to identify subtle mutations or combinations thereof that confer preferential binding to bumped rapalogs. Several suitable mutagenesis schemes have been described, including alanine-scanning mutagenesis (Cunningham and Wells (1989) Science 244, 1081–1085), PCR misincorporation mutagenesis (see e.g. Cadwell and Joyce, 1992 PCR Meth. Applic. 2, 28–33), and 'DNA shuffling' (Stemmer, 1994, Nature 370, 389–391 and Crameri et al, 1996, Nature Medicine 2, 100–103). These techniques produce libraries of random mutants, or sets of single mutants, that are then searched by screening or selection approaches.

In many cases, an effective strategy to identify the best mutants for preferential binding of a given bump is a combination of structure-based and unbiased approaches. See Clackson and Wells, 1994, Trends Biotechnology 12, 173–184 (review). For example we contemplate the construction of libraries in which key contact residues are randomized by PCR with degenerate oligonucleotides, but with amplification performed using error-promoting conditions to introduce further mutations at random sites. A further example is the combination of component DNA fragments from structure-based and unbiased random libraries using DNA shuffling.

Screening of libraries for desirable mutations may be performed by use of a yeast 2-hybrid system (Fields and Song (1989) Nature 340, 245–246). For example, an FRB-VP16 fusion may be introduced into one vector, and a library of randomized FKBP sequences cloned into a separate GAL4 fusion vector. Yeast co-transformants are treated with rapalog, and those harboring complementary FKBP mutants are identified by for example beta-galactosidase or luciferase production (a screen), or survival on plates lacking an essential nutrient (a selection), as appropriate for the vectors used. The requirement for bumped rapamycin to bridge the FKBP-FRAP interaction is a useful screen to eliminate false positives.

A further strategy for isolating modified ligand-binding domains from libraries of FKBP (or FRB) mutants utilizes a genetic selection for functional dimer formation described by Hu et. al. (Hu, J. C., et al. 1990. Science. 250:1400–1403; for review see Hu, J. C. 1995. Structure. 3:431–433). This strategy utilizes the fact that the bacteriophage lambda repressor cI binds to DNA as a homodimer and that binding of such homodimers to operator DNA prevents transcription of phage genes involved in the lytic pathway of the phage life cycle. Thus, bacterial cells expressing functional lambda repressor are immune to lysis by superinfecting phage lambda. Repressor protein comprises an amino terminal DNA binding domain (amino acids 1–92), joined by a 40 amino acid flexible linker to a carboxy terminal dimerization domain. The isolated N-terminal domain binds to DNA with low affinity due to inefficient dimer formation. High affinity DNA binding can be restored with heterologous dimerization domains such as the GCN4 "leucine zipper". Hu et al have described a system in which phage immunity is used as a genetic selection to isolate GCN4 leucine zipper mutants capable of mediating lambda repressor dimer formation from a large population of sequences (Hu et. al., 1990).

For example, to use the lambda repressor system to identify FRAP mutants complementary to bumped rapalogs, lambda repressor-FRAP libraries bearing mutant FRAP sequences are transformed into E. coli cells expressing wild-type lambda repressor-FKBP protein. Plasmids expressing FRAP mutants are isolated from those colonies that survive lysis on bacterial plates containing high titres of lambda phage and "bumped" rapamycin compounds. Alternatively, to isolate FKBP mutants, the above strategy is repeated with lambda repressor-FKBP libraries bearing mutant FKBP sequences transformed into E. coli cells expressing wildtype lambda repressor-FRAP protein.

A further alternative is to clone the randomized FKBP sequences into a vector for phage display, allowing in vitro selection of the variants that bind best to the rapalog. Affinity selection in vitro may be performed in a number of ways. For example, rapalog is mixed with the library phage pool in solution in the presence of recombinant FRAP tagged with an affinity handle (for example a hexa-histidine tag, or GST), and the resultant complexes are captured on the appropriate affinity matrix to enrich for phage displaying FKBP harboring complementary mutations. Techniques for phage display have been described, and other in vitro selection systems can also be contemplated (for example display on lambda phage, display on plasmids, display on baculovirus). Furthermore, selection and screening strategies can also be used to improve other properties of benefit in the application of this invention, such as enhanced stability in vivo. For a review see Clackson, T. & Wells, J. A. 1994. Trends Biotechnol. 12, 173–184.

(b) FRAP

Similar considerations apply to the generation of mutant FRB domains which bind preferentially to C3 rapalogs containing modifications (i.e., are 'bumped') relative to rapamycin in the FRAP-binding portion of the macrocycle. For example, one may obtain preferential binding using rapalogs bearing substituents other than —OMe at the C7 position with FRBs based on the human FRAP FRB peptide sequence but bearing amino acid substitutions for one of more of the residues Tyr2038, Phe2039, Thr2098, Gln2099, Trp2101, Ser2035, Tyr2105, Pro2095, and any other residue in the vicinity of the rapamycin, triene or residues near the rapamycin triene and Asp2102. Exemplary mutations include Y2038H, Y2038L, Y2038V, Y2038A, F2039H, F2039L, F2039A, F2039V, D2102A, T2098A, T2098N, and T2098S. Rapalogs bearing substituents other than —OH at C28 and/or substituents other than =O at C30 may be used to obtain preferential binding to FRAP proteins bearing an amino acid substitution for Glu2032. Exemplary mutations include E2032A and E2032S. Proteins comprising an FRB containing one or more amino acid replacements at the foregoing positions, libraries of proteins or peptides randomized at those positions (i.e., containing various substituted amino acids at those residues), libraries randomizing the entire protein domain, or combinations of these sets of mutants are made using the procedures described above to identify mutant FRAPs that bind preferentially to bumped rapalogs.

The affinity of candidate mutant FRBs for the complex of an FKBP protein complexed with a rapalog may be assayed by a number of techniques; for example binding of in vitro translated FRB mutants to GST-FKBP in the presence of drug (Chen et al. 1995. Proc. Natl. Acad. Sci. USA 92, 4947–4951); or ability to participate in a rapalog-dependent transcriptionally active complex with an appropriate FKBP fusion protein in a yeast or mammalian two- three-hybrid assay.

FRB mutants with desired binding properties may be isolated from libraries displayed on phage using a variety of sorting strategies. For example, a rapalog is mixed with the library phage pool in solution in the presence of recombinant FKBP tagged with an affinity handle (for example a hexa-histidine tag, or GST), and the resultant complexes are captured on the appropriate affinity matrix to enrich for phage displaying FRAP harboring complementary mutations.

An additional feature of the FRB fusion protein that may vary in the various embodiments of this invention is the exact sequence of the FRB domain used. In some applications it may be preferred to use portions of an FRB which are larger than the minimal (89 amino acid) FRB domain. These include extensions N-terminal to residue Glu2025 (preferably extending to at least Arg2018 or Ile2021), as well as C-terminal extensions beyond position 2113, e.g. to position 2113, 2141 or 2174 or beyond), which may in some cases improve the stability of the folded FRB domain and/or the efficiency of expression. Other applications in which different FRB sequence termini may be used include those in which a long linker is desired for steric reasons on one or both sides of the FRB domain, for example to accommodate the distortions of the polypeptide chain required for FRB-mediated protein—protein association at the cell membrane or on DNA. Conversely, in other applications short linkers on one or both sides of the FRB domain may be preferred or required to present the heterologous effector domain(s) appropriately for biological function. In human gene therapy applications the use of naturally occurring human FRAP sequence for such linkers will generally be preferred to the introduction of heterologous sequences, or reduce the risk of provoking an immune response in the host organism.

Some rapalogs, especially rapalogs with modifications or substituents (relative to rapamycin) at positions believed to lie near the boundary between the FKBP binding domain and the FRAP binding domain, such as those on C28, C30, C7 and C24, possess reduced ability, relative to rapamycin, to form complexes with both mammalian FKBP and FRB domains, in particular, with those domains containing naturally occurring human peptide sequence. That reduced ability may be manifested as a reduced binding affinity as determined by any of the direct or indirect assay means mentioned herein or as reduced immunosuppressive activity as determined in an appropriate assay such as a T cell proliferation assay. In such cases, iterative procedures may be used to identify pairs of mutant FKBPs and mutant FRBs that are capable of complexing with the rapalog more effectively than the corresponding domains containing naturally occurring human peptide sequence. For example, one may first identify a complementary modified FKBP domain capable of binding to the rapalog, as discussed previously, and then using this mutant FKBP domain as an affinity matrix in complex with the rapalog, one may select a complementary modified FRB domain capable of associating with that complex. Several cycles of such mutagenesis and screening may be performed to optimize the protein pair.

For some embodiments, it will be desirable to use FRB and/or FKBP domains containing mutations that can affect the protein—protein interaction. For instance, mutant FKBP domains which when bound to a given rapalog are capable of complexing with an endogenous FRB measurably less effectively than to a mutant FRB are of particular interest. Also of interest are mutant FRB domains which are capable of associating with a complex of a mutant FKBP with a given rapalog measurable more effectively than with a complex of an endogenous FKBP with the rapalog. Similar selection and screening approaches to those delineated previously can be used (i) to identify amino acid substitutions, deletions or insertions to an FKBP domain which measurably diminish the domain's ability to form the tripartite complex with a given rapalog and the endogenous FRB; (ii) to identify amino acid substitutions, deletions or insertions to an FRB domain which measurably diminish the domain's ability to form the tripartite complex with a given rapalog and the endogenous FKBP; and (iii) to select and/or otherwise identify compensating mutation(s) in the partner protein. As examples of suitable mutant FKBPs with diminished effectiveness in tripartite complex formation, we include mammalian, preferably human FKBP in which one or both of His87 and Ile90 are replaced with amino acids such as Arg, Trp, Phe, Tyr or Lys which contain bulky side chain groups; FRB domains, preferably containing mammalian, and more preferably of human, peptide sequence may then be mutated as described above to generate complementary variants which are capable of forming a tripartite complex with the mutant FKBP and a given rapalog. Illustrative FRB mutations which may be useful with H87W or H87R hFKBP12s include human FRBs in which Y2038 is replaced by V, S, A or L; F2039 is replaced by A; and/or R2042 is replaced by L, A or S. Illustrative FRB mutations which may be useful with I90W or I90R hFKBP12s include human FRBs in which K2095 is replaced with L, S, A or T.

Additionally, in optimizing the receptor domains of this invention, it should be appreciated that immunogenicity of a polypeptide sequence is thought to require the binding of peptides by MHC proteins and the recognition of the presented peptides as foreign by endogenous T-cell receptors. It may be preferable, at least in human gene therapy applications, to tailor a given foreign peptide sequence, including junction peptide sequences, to minimize the probability of its being immunologically presented in humans. For example, peptide binding to human MHC class I molecules has strict requirements for certain residues at key 'anchor'positions in the bound peptide: e.g. HLA-A2 requires leucine, methionine or isoleucine at position 2 and leucine or valine at the C-terminus (for review see Stern and Wiley (1994) Structure 2, 145–251). Thus in engineering proteins in the practice of this invention, this periodicity of these residues is preferably avoided, especially in human gene therapy applications. The foregoing applies to all protein engineering aspects of the invention, including without limitation the engineering of point mutations into receptor domains, and to the choice or design of boundaries between the various protein domains.

Other Components, Design Features and Applications

The chimeric proteins may contain as a heterologous domain a cellular localization domain such as a membrane retention domain. See e.g. PCT/US94/01617, especially pages 26–27. Briefly, a membrane retention domain can be isolated from any convenient membrane-bound protein, whether endogenous to the host cell or not. The membrane retention domain may be a transmembrane retention domain, i.e., an amino acid sequence which extends across the membrane as in the case of cell surface proteins, including many receptors. The transmembrane peptide sequence may be extended to span part or all of an extracellular and/or intracellular domain as well. Alternatively, the membrane retention domain may be a lipid membrane retention domain such as a myristoylation or palmitoylation site which permits association with the lipids of the cell surface membrane. Lipid membrane retention domains will usually be added at the 5' end of the coding sequence for N-terminal binding to the membrane and, proximal to the 3' end for C-terminal binding. Peptide sequences involving post-translational processing to provide for lipid membrane binding are described by Carr, et al., PNAS USA (1988) 79, 6128; Aitken, et al., FEBS Lett. (1982) 150, 314; Henderson, et al., PNAS USA (1983) 80, 319; Schulz, et al., Virology (1984), 123, 2131; Dellman, et al., Nature (1985) 314, 374; and reviewed in Ann. Rev. of Biochem. (1988) 57, 69. An amino acid sequence of interest includes the sequence M-G-S-S-K-S-K-P-K-D-P-S-Q-R. Various DNA sequences can be used to encode such sequences in the various chimeric proteins of this invention. Other localization domains include organelle-targeting domains and sequences such as -K-D-E-L and -H-D-E-L which target proteins bearing them to the endoplasmic reticulum, as well as nuclear localization sequences which are particularly useful for chimeric proteins designed for (direct) transcriptional regulation. Various cellular localization sequences and signals are well known in the art.

Further details which may be used in the practice of the subject invention relating to the design, assembly and use of constructs encoding chimeric proteins containing various effector domains including cytoplasmic signal initiation domains such as the CD3 zeta chain, nuclear transcription factor domains including among others VP16 and GAL4, domains capable of triggering apoptosis including the Fas cytoplasmic domain and others are disclosed in PCT/US94/01617 and PCT/US95/10591. The latter international application further discloses additional features particularly applicable to the creation of genetically engineered animals which may be used as disease models in biopharmaceutical research. Those features include the use of tissue specific regulatory elements in the constructs for expression of the chimeric proteins and the application of regulated transcription to the expression of Cre recombinase as the target gene leading to the elimination of a gene of interest flanked by loxP sequences. Alternatively, flp and its cognate recognition sequences may be used instead of Cre and lox. Those features may be adapted to the subject invention.

In various cases, especially in embodiments involving whole animals containing cells engineered in accordance with this invention, it will often be preferred, and in some cases required, that the various domains of the chimeric proteins be derived from proteins of the same species as the host cell. Thus, for genetic engineering of human cells, it is often preferred that the heterologous domains (as well as the FKBP and FRB domains) be of human origin, rather than of bacterial, yeast or other non-human source.

Epitope tags may also be incorporated into chimeric proteins of this invention to permit convenient detection.

Tissue-Specific or Cell-Type Specific Expression

It will be preferred in certain embodiments, that the chimeric proteins be expressed in a cell-specific or tissue-specific manner. Such specificity of expression may be achieved by operably linking one ore more of the DNA sequences encoding the chimeric protein(s) to a cell-type specific transcriptional regulatory sequence (e.g. promoter/enhancer). Numerous cell-type specific transcriptional regulatory sequences are known. Others may be obtained from genes which are expressed in a cell-specific manner. See e.g. PCT/US95/10591, especially pp. 36–37.

For example, constructs for expressing the chimeric proteins may contain regulatory sequences derived from known genes for specific expression in selected tissues.

Representative examples are tabulated below:

| Tissue | Gene | Reference |
|---|---|---|
| lens | g2-crystallin | Breitman, M. L., Clapoff, S., Rossant, J., Tsui, L. C., Golde, L. M., Maxwell, I. H., Bernstin, A. (1987) Genetic Ablation: targeted expression of a toxin gene causes microphthalmia in transgenic mice. Science 238: 1563–1565 |
| | aA-crystallin | Landel, C. P., Zhao, J., Bok, D., Evans, G. A. (1988) Lens-specific expression of a recombinant ricin induces developmental defects in the eyes of transgenic mice. Genes Dev. 2: 1168–1178 Kaur, S., key, B., Stock, J., McNeish, J. D., Akeson, R., Potter, S. S. (1989) Targeted ablation of alpha-crystallin-synthesizing cells produces lens-deficient eyes in transgenic mice. Development 105: 613–619 |
| pituitary - somatotrophic cells | Growth hormone | Behringer, R. R., Mathews, L. S., Palmiter, R. D., Brinster, R. L. (1988) Dwarf mice produced by genetic ablation of growth hormone-expressing cells. Genes Dev. 2: 453–461 |
| pancreas | Insulin- Elastase - acinar cell specific | Ornitz, D. M., Palmiter, R. D., Hammer, R. E., Brinster, R. L., Swift, G. H., MacDonald, R. J. (1985) Specific expression of an elastase-human growth fusion in pancreatic acinar cells of transgeneic mice. Nature 131: 600–603 Palmiter, R. D., Behringer, R. R., Quaife, C. J., Maxwell, F., Maxwell, I. H., Brinster, R. L. (1987) Cell lineage ablation in transgeneic mice by cell-specific expression of a toxin gene. Cell 50: 435–443 |
| T cells | 1ck promoter | Chaffin, K. E., Beals, C. R., Wilkie, T. M., Forbush, K. A., Simon, M. I., Perlmutter, R. M. (1990) EMBO Journal 9: 3821–3829 |
| B cells | Immunoglobulin kappa light chain | Borelli, E., Heyman, R., Hsi, M., Evans, R. M. (1988) Targeting of an inducible toxic phenotype in animal cells. Proc. Natl. Acad. Sci. USA 85: 7572–7576 Heyman, R. A., Borrelli, E., Lesley, J., Anderson, D., Richmond, D. D., Baird, S. M., Hyman, R., Evans, R. M. (1989) Thymidine kinase obliteration: creation of transgenic mice with controlled immunodeficiencies. Proc. Natl. Acad. Sci. USA 86: 2698–2702 |
| Schwann cells | P$_0$ promoter | Messing, A., Behringer, R. R., Hammang, J. P. Palmiter, R D, Brinster, R L, Lemke, G., P0 promoter directs espression of reporter and toxin genes to Schwann cells of transgenic mice. Neuron 8: 507–520 1992 |
| | Myelin basic protein | Miskimins, R. Knapp, L., Dewey, M J, Zhang, X. Cell and tissue-specific expression of a heterologous gene under control of the myelin basic protein gene promoter in trangenic mice. Brain Res Dev Brain Res 1992 Vol 65: 217–21 |
| spermatids | protamine | Breitman, M. L., Rombola, H., Maxwell, I. H., Klintworth, G. K., Bernstein, A. (1990) Genetic ablation in transgenic mice with attenuated diphtheria toxin A gene. Mol. Cell. Biol. 10: 474–479 |

-continued

| Tissue | Gene | Reference |
|---|---|---|
| lung | Lung surfactant gene | Ornitz, D. M., Palmiter, R. D., Hammer, R. E., Brinster, R. L., Swift, G. H., MacDonald, R. J. (1985) Specific expression of an elastase-human growth fusion in pancreatic acinar cells of transgeneic mice. Nature 131: 600–603 |
| adipocyte P2 | | Ross, S. R, Braves, R A, Spiegelman, B M Targeted expression of a toxin gene to adipose tissue: transgenic mice resistant to obesity Genes and Dev 7: 1318–24 1993 |
| muscle | myosin light chain | Lee, K J, Ross, R S, Rockman, H A, Harris, A N, O'Brien, T X, van-Bilsen, M., Shubeita, H E, Kandolf, R., Brem, G., Prices et al J. BIol. Chem. 1992 Aug. 5, 267: 15875–85 |
| | Alpha actin | Muscat, G E., Perry, S., Prentice, H. Kedes, L. The human skeletal alpha-actin gene is regulated by a muscle-specific enhancer that binds three nuclear factors. Gene Expression 2, 111–26, 1992 . . . / . . . |
| neurons | neuro-filament proteins | Reeben, M. Halmekyto, M. Alhonen, L. Sinervirta, R. Saarma, M. Janne, J. Tissue-specific expression of rat light neurofilament promoter-driven reporter gene in transgenic mice. BBRC 1993: 192: 465–70 |
| liver | tyrosine amino-transferase, albumin, apolipo-proteins | |

Target Gene Constructs

In embodiments of the invention in which the chimeric proteins are designed such that their multimerization activates transcription of a target gene, an appropriate target gene construct is also used in the engineered cells. Appropriate target gene constructs are those containing a target gene and a cognate transcriptional control element such as a promoter and/or enhancer which is responsive to the multimerization of the chimeric proteins. In embodiments involving direct activation of transcription, that responsiveness may be achieved by the presence in the target gene construct of one or more DNA sequences recognized by the DNA-binding domain of a chimeric protein of this invention (i.e., a DNA sequence to which the chimeric protein binds). In embodiments involving indirect activation of transcription, responsiveness may be achieved by the presence in the target gene construct of a promoter and/or enhancer sequence which is activated by an intracellular signal generated by multimerization of the chimeric proteins. For example, where the chimeric proteins contain the TCR zeta chain intracellular domain, the target gene is linked to and under the expression control of the IL-2 promoter region.

This invention also provides target DNA constructs containing (a) a cognate DNA sequence, e.g. to which a DNA-binding chimeric protein of this invention is capable of binding (or which is susceptible to indirect activation as discussed above), and (b) flanking DNA sequence from the locus of a desired target gene endogenous to the host cells. These constructs permit homologous recombination of the cognate DNA sequence into a host cell in association with an endogenous target gene. In other embodiments the construct contains a desired gene and flanking DNA sequence from a target locus permitting the homologous recombination of the target gene into the desired locus. Such a target construct may also contain the cognate DNA sequence, or the cognate DNA sequence may be provided by the locus.

The target gene in any of the foregoing embodiments may encode for example a surface membrane protein (such as a receptor protein), a secreted protein, a cytoplasmic protein, a nuclear protein, a recombinase such as Cre, a ribozyme or an antisense RNA. See PCT/US94/01617 for general design and construction details and for various applications including gene therapy and see PCT/US95/10591 regarding applications to animal models of disease.

This invention encompasses a variety of configurations for the chimeric proteins. In all cases involving the activation of target gene transcription, however, the chimeric proteins share an important characteristic: cells containing constructs encoding the chimeras and a target gene construct express the target gene at least one, preferably at least two, and more preferably at least three or four or more orders of magnitude more in the presence of the multimerizing ligand than in its absence. Optimally, expression of the selected gene is not observed unless the cells are or have been exposed to a multimerizing ligand.

To recap, the chimeric proteins are capable of initiating a detectable level of transcription of target genes within the engineered cells upon exposure of the cells to the a C3 rapalog, i.e., following multimerization of the chimeras. Thus, transcription of target genes is activated in genetically engineered cells of this invention following exposure of the cells to a C3 rapalog capable of multimerizing the chimeric protein molecules. Said differently, genetically engineered cells of this invention contain chimeric proteins as described above and are responsive to the presence and/or concentration of a C3 rapalog which is capable of multimerizing those chimeric protein molecules. That responsiveness is manifested by the activation of transcription of a target gene. Such transcriptional activity can be readily detected by any conventional assays for transcription of the target gene. In other embodiments, the biological response to ligand-mediated multimerization of the chimeras is cell death or other biological events rather than direct activation of transcription of a target gene.

Design and Assembly of the DNA Constructs

Constructs may be designed in accordance with the principles, illustrative examples and materials and methods disclosed in the patent documents and scientific literature cited herein, each of which is incorporated herein by reference, with modifications and further exemplification as described herein. Components of the constructs can be prepared in conventional ways, where the coding sequences and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc. as appropriate. In the case of DNA constructs encoding fusion proteins, DNA sequences encoding individual domains and sub-domains are joined such that they constitute a single open reading frame encoding a fusion protein capable of being translated in cells or cell lysates into a single polypeptide harboring all component domains. The DNA construct encoding the fusion protein may then be placed into a vector that directs the expression of the protein in the appropriate cell type(s). For biochemical analysis of the encoded chimera, it may be desirable to construct plasmids that direct the expression of the protein in bacteria or in reticulocyte-lysate systems. For use in the production of proteins in mammalian cells, the protein-encoding sequence is introduced into an expression vector that directs expression in these cells. Expression vectors suitable for such uses are well known in the art. Various sorts of such vectors are commercially available.

Constructs encoding the chimeric proteins and target genes of this invention can be introduced into the cells as one or more DNA molecules or constructs, in many cases in association with one or more markers to allow for selection of host cells which contain the construct(s). The construct(s) once completed and demonstrated to have the appropriate sequences may then be introduced into a host cell by any convenient means. The constructs may be incorporated into vectors capable of episomal replication (e.g. BPV or EBV vectors) or into vectors designed for integration into the host cells' chromosomes. The constructs may be integrated and packaged into non-replicating, defective viral genomes like Adenovirus, Adeno-associated virus (AAV), or Herpes simplex virus (HSV) or others, including retroviral vectors, for infection or transduction into cells. Viral delivery systems are discussed in greater detail below. Alternatively, the construct may be introduced by protoplast fusion, electroporation, biolistics, calcium phosphate transfection, lipofection, microinjection of DNA or the like. The host cells will in some cases be grown and expanded in culture before introduction of the construct(s), followed by the appropriate treatment for introduction of the construct(s) and integration of the construct(s). The cells will then be expanded and screened by virtue of a marker present in the constructs. Various markers which may be used successfully include hprt, neomycin resistance, thymidine kinase, hygromycin resistance, etc., and various cell-surface markers such as Tac, CD8, CD3, Thy1 and the NGF receptor.

In some instances, one may have a target site for homologous recombination, where it is desired that a construct be integrated at a particular locus. For example, one can delete and/or replace an endogenous gene (at the same locus or elsewhere) with a recombinant target construct of this invention. For homologous recombination, one may generally use either ½ or O-vectors. See, for example, Thomas and Capecchi, Cell (1987) 51, 503–512; Mansour, et al., Nature (1988) 336, 348–352; and Joyner, et al., Nature (1989) 338, 153–156.

The constructs may be introduced as a single DNA molecule encoding all of the genes, or different DNA molecules having one or more genes. The constructs may be introduced simultaneously or consecutively, each with the same or different markers.

Vectors containing useful elements such as bacterial or yeast origins of replication, selectable and/or amplifiable markers, promoter/enhancer elements for expression in procaryotes or eucaryotes, and mammalian expression control elements, etc. which may be used to prepare stocks of construct DNAs and for carrying out transfections are well known in the art, and many are commercially available.

Delivery of Nucleic Acid: Ex Vivo and In Vivo

Any means for the introduction of heterologous nucleic acids into host cells, especially eucaryotic cells, an in particular animal cells, preferably human or non-human mammalian cells, may be adapted to the practice of this invention. For the purpose of this discussion, the various nucleic acid constructs described herein may together be referred to as the transgene. Ex vivo approaches for delivery of DNA include calcium phosphate precipitation, electroporation, lipofection and infection via viral vectors. Two general in vivo gene therapy approaches include (a) the delivery of "naked", lipid-complexed or liposome-formulated or otherwise formulated DNA and (b) the delivery of the heterologous nucleic acids via viral vectors. In the former approach, prior to formulation of DNA, e.g. with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126–139, 1995). Formulation of DNA, e.g. with various lipid or liposome materials, may then be effected using known methods and materials and delivered to the recipient mammal.

While various viral vectors may be used in the practice of this invention, retroviral-, AAV- and adenovirus-based approaches are of particular interest. See, for example, Dubensky et al. (1984) Proc. Natl. Acad. Sci. USA 81, 7529–7533; Kaneda et al., (1989) Science 243,375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The following additional guidance on the choice and use of viral vectors may be helpful to the practitioner.

Retroviral Vectors

Retroviruses are a class of RNA viruses in which the RNA genome is reversely transcribed to DNA in the infected cell. The retroviral genome can integrate into the host cell genome and requires three viral genes, gag, pol and env, as well as the viral long terminal repeats (LTRs). The LTRs also act as enhancers and promoters for the viral genes. The packaging sequence of the virus, (Y), allows the viral RNA to be distinguished from other RNAs in the cell (Verma et al., Nature 389:239–242, 1997). For expression of a foreign gene, the viral proteins are replaced with the gene of interest in the viral vector, which is then transfected into a packaging line containing the viral packaging components. Packaged virus is secreted from the packaging line into the culture medium, which can then be used to infect cells in culture. Since retroviruses are unable to infect non-dividing cells, they have been used primarily for ex vivo gene therapy.

AAV Vectors

Adeno-associated virus (AAV)-based vectors are of general interest as a delivery vehicle to various tissues, including muscle and lung. AAV vectors infect cells and stably integrate into the cellular genome with high frequency. AAV can infect and integrate into growth-arrested cells (such as the pulmonary epithelium), and is non-pathogenic.

The AAV-based expression vector to be used typically includes the 145 nucleotide AAV inverted terminal repeats (ITRs) flanking a restriction site that can be used for subcloning of the transgene, either directly using the restriction site available, or by excision of the transgene with restriction enzymes followed by blunting of the ends, ligation of appropriate DNA linkers, restriction digestion, and ligation into the site between the ITRs. The capacity of AAV vectors is about 4.4 kb. The following proteins have been expressed using various AAV-based vectors, and a variety of promoter/enhancers: neomycin phosphotransferase, chloramphenicol acetyl transferase, Fanconi's anemia gene, cystic fibrosis transmembrane conductance regulator, and granulocyte macrophage colony-stimulating factor (Kotin, R. M., Human Gene Therapy 5:793–801, 1994, Table I). A transgene incorporating the various DNA constructs of this invention can similarly be included in an AAV-based vector. As an alternative to inclusion of a constitutive promoter such as CMV to drive expression of the recombinant DNA encoding the fusion protein(s), an AAV promoter can be used (ITR itself or AAV p5 (Flotte, et al. J. Biol. Chem. 268:3781–3790, 1993)).

Such a vector can be packaged into AAV virions by reported methods. For example, a human cell line such as 293 can be co-transfected with the AAV-based expression vector and another plasmid containing open reading frames encoding AAV rep and cap under the control of endogenous AAV promoters or a heterologous promoter. In the absence of helper virus, the rep proteins Rep68 and Rep78 prevent accumulation of the replicative form, but upon superinfection with adenovirus or herpes virus, these proteins permit replication from the ITRs (present only in the construct containing the transgene) and expression of the viral capsid proteins. This system results in packaging of the transgene DNA into AAV virions (Carter, B. J., Current Opinion in Biotechnology 3:533–539, 1992; Kotin, R. M, Human Gene Therapy 5:793–801, 1994)). Methods to improve the titer of AAV can also be used to express the transgene in an AAV virion. Such strategies include, but are not limited to: stable expression of the ITR-flanked transgene in a cell line followed by transfection with a second plasmid to direct viral packaging; use of a cell line that expresses AAV proteins inducibly, such as temperature-sensitive inducible expression or pharmacologically inducible expression. Additionally, one may increase the efficiency of AAV transduction by treating the cells with an agent that facilitates the conversion of the single stranded form to the double stranded form, as described in Wilson et al., WO96/39530.

Concentration and purification of the virus can be achieved by reported methods such as banding in cesium chloride gradients, as was used for the initial report of AAV vector expression in vivo (Flotte, et al. J. Biol. Chem. 268:3781–3790, 1993) or chromatographic purification, as described in O'Riordan et al., WO97/08298.

For additional detailed guidance on AAV technology which may be useful in the practice of the subject invention, including methods and materials for the incorporation of a transgene, the propagation and purification of the recombinant AAV vector containing the transgene, and its use in transfecting cells and mammals, see e.g. Carter et al, U.S. Pat. No. 4,797,368 (10 Jan. 1989); Muzyczka et al, U.S. Pat. No. 5,139,941 (18 Aug. 1992); Lebkowski et al, U.S. Pat. No. 5,173,414 (22 Dec. 1992); Srivastava, U.S. Pat. No. 5,252,479 (12 Oct. 1993); Lebkowski et al, U.S. Pat. No. 5,354,678 (11 Oct. 1994); Shenk et al, U.S. Pat. No. 5,436,146 (25 Jul. 1995); Chatterjee et al, U.S. Pat. No. 5,454,935 (12 Dec. 1995), Carter et al WO 93/24641 (published 9 Dec. 1993), and Flotte et al., U.S. Pat. No. 5,658,776 (19 Aug. 1997).

Adenovirus Vectors

Various adenovirus vectors have been shown to be of use in the transfer of genes to mammals, including humans. Replication-deficient adenovirus vectors have been used to express marker proteins and CFTR in the pulmonary epithelium. The first generation E1a deleted adenovirus vectors have been improved upon with a second generation that includes a temperature-sensitive E2a viral protein, designed to express less viral protein and thereby make the virally infected cell less of a target for the immune system (Goldman et al., Human Gene Therapy 6:839–851, 1995). More recently, a viral vector deleted of all viral open reading frames has been reported (Fisher et al., Virology 217:11–22, 1996). Moreover, it has been shown that expression of viral IL-10 inhibits the immune response to adenoviral antigen (Qin et al., Human Gene Therapy 8:1365–1374, 1997).

DNA sequences of a number of adenovirus types are available from Genbank. The adenovirus DNA sequences may be obtained from any of the 41 human adenovirus types currently identified. Various adenovirus strains are available from the American Type Culture Collection, Rockville, Md., or by request from a number of commercial and academic sources. A transgene as described herein may be incorporated into any adenoviral vector and delivery protocol, by the same methods (restriction digest, linker ligation or filling in of ends, and ligation) used to insert the CFTR or other genes into the vectors. Hybrid Adenovirus-AAV vectors represented by an adenovirus capsid containing selected portions of the adenovirus sequence, 5' and 3' AAV ITR sequences flanking the transgene and other conventional vector regulatory elements may also be used. See e.g. Wilson et al, International Patent Application Publication No. WO 96/13598. For additional detailed guidance on adenovirus and hybrid adenovirus-AAV technology which may be useful in the practice of the subject invention, including methods and materials for the incorporation of a transgene, the propagation and purification of recombinant virus containing the transgene, and its use in transfecting cells and mammals, see also Wilson et al, WO 94/28938, WO 96/13597 and WO 96/26285, and references cited therein.

Generally the DNA or viral particles are transferred to a biologically compatible solution or pharmaceutically acceptable delivery vehicle, such as sterile saline, or other aqueous or non-aqueous isotonic sterile injection solutions or suspensions, numerous examples of which are well known in the art, including Ringer's, phosphate buffered saline, or other similar vehicles.

Preferably, in gene therapy applications, the DNA or recombinant virus is administered in sufficient amounts to transfect cells at a level providing therapeutic benefit without undue adverse effects. Optimal dosages of DNA or virus depends on a variety of factors, as discussed elsewhere, and may thus vary somewhat from patient to patient. Again, therapeutically effective doses of viruses are considered to be in the range of about 20 to about 50 ml of saline solution containing concentrations of from about $1 \times 10^7$ to about $1 \times 10^{10}$ pfu of virus/ml, e.g. from $1 \times 10^8$ to $1 \times 10^9$ pfu of virus/ml.

Host Cells

This invention is particularly useful for the engineering of animal cells and in applications involving the use of such engineered animal cells. The animal cells may be insect, worm or mammalian cells. While various mammalian cells may be used, including, by way of example, equine, bovine, ovine, canine, feline, murine, and non-human primate cells, human cells are of particular interest. Among the various species, various types of cells may be used, such as hematopoietic, neural, glial, mesenchymal, cutaneous, mucosal, stromal, muscle (including smooth muscle cells), spleen, reticulo-endothelial, epithelial, endothelial, hepatic, kidney, gastrointestinal, pulmonary, fibroblast, and other cell types. Of particular interest are hematopoietic cells, which may include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells.

The cells may be autologous cells, syngeneic cells, allogeneic cells and even in some cases, xenogeneic cells with respect to an intended host organism. The cells may be modified by changing the major histocompatibility complex ("MHC") profile, by inactivating β2-microglobulin to prevent the formation of functional Class I MHC molecules, inactivation of Class II molecules, providing for expression of one or more MHC molecules, enhancing or inactivating cytotoxic capabilities by enhancing or inhibiting the expression of genes associated with the cytotoxic activity, or the like.

In some instances specific clones or oligoclonal cells may be of interest, where the cells have a particular specificity, such as T cells and B cells having a specific antigen specificity or homing target site specificity.

Introduction of Constructs into Animals

Cells which have been modified ex vivo with the DNA constructs may be grown in culture under selective conditions and cells which are selected as having the desired construct(s) may then be expanded and further analyzed, using, for example, the polymerase chain reaction for determining the presence of the construct in the host cells and/or assays for the production of the desired gene product(s). Once modified host cells have been identified, they may then be used as planned, e.g. grown in culture or introduced into a host organism.

Depending upon the nature of the cells, the cells may be introduced into a host organism, e.g. a mammal, in a wide variety of ways. Hematopoietic cells may be administered by injection into the vascular system, there being usually at least about $10^4$ cells and generally not more than about $10^{10}$ cells. The number of cells which are employed will depend upon a number of circumstances, the purpose for the introduction, the lifetime of the cells, the protocol to be used, for example, the number of administrations, the ability of the cells to multiply, the stability of the therapeutic agent, the physiologic need for the therapeutic agent, and the like. Generally, for myoblasts or fibroblasts for example, the number of cells will be at least about 104 and not more than about 109 and may be applied as a dispersion, generally being injected at or near the site of interest. The cells will usually be in a physiologically-acceptable medium.

Cells engineered in accordance with this invention may also be encapsulated, e.g. using conventional biocompatible materials and methods, prior to implantation into the host organism or patient for the production of a therapeutic protein. See e.g. Hguyen et al, Tissue Implant Systems and Methods for Sustaining viable High Cell Densities within a Host, U.S. Pat. No. 5,314,471 (Baxter International, Inc.); Uludag and Sefton, 1993, J. Biomed. Mater. Res. 27 (10): 1213–24 (HepG2 cells/hydroxyethyl methacrylate-methyl methacrylate membranes); Chang et al, 1993, Hum Gene Ther 4 (4):433–40 (mouse Ltk-cells expressing hGH/immunoprotective perm-selective alginate microcapsules; Reddy et al, 1993, J Infect Dis 168 (4):1082–3 (alginate); Tai and Sun, 1993, FASEB J 7 (11):1061–9 (mouse fibroblasts expressing hGH/alginate-poly-L-lysine-alginate membrane); Ao et al, 1995, Transplantation Proc. 27 (6):3349, 3350 (alginate); Rajotte et al, 1995, Transplantation Proc. 27 (6):3389 (alginate); Lakey et al, 1995, Transplantation Proc. 27 (6):3266 (alginate); Korbutt et al, 1995, Transplantation Proc. 27 (6):3212 (alginate); Dorian et al, U.S. Pat. No. 5,429,821 (alginate); Emerich et al, 1993, Exp Neurol 122 (1):37–47 (polymer-encapsulated PC12 cells); Sagen et al, 1993, J Neurosci 13 (6):2415–23 (bovine chromaffin cells encapsulated in semipermeable polymer membrane and implanted into rat spinal subarachnoid space); Aebischer et al, 1994, Exp Neurol 126 (2):151–8 (polymer-encapsulated rat PC12 cells implanted into monkeys; see also Aebischer, WO 92/19595); Savelkoul et al, 1994, J Immunol Methods 170 (2):185–96 (encapsulated hybridomas producing antibodies; encapsulated transfected cell lines expressing various cytokines); Winn et al, 1994, PNAS USA 91 (6):2324–8 (engineered BHK cells expressing human nerve growth factor encapsulated in an immunoisolation polymeric device and transplanted into rats); Emerich et al, 1994, Prog Neuropsychopharmacol Biol Psychiatry 18 (5):935–46 (polymer-encapsulated PC12 cells implanted into rats); Kordower et al, 1994, PNAS USA 91 (23):10898–902 (polymer-encapsulated engineered BHK cells expressing hNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments the cells to be encapsulated may express one or more chimeric proteins containing component domains derived from proteins of the host species and/or from viral proteins or proteins from species other than the host species. For example in such cases the chimeras may contain elements derived from GAL4 and VP16. The cells may be derived from one or more individuals other than the recipient and may be derived from a species other than that of the recipient organism or patient.

Instead of ex vivo modification of the cells, in many situations one may wish to modify cells in vivo. For this purpose, various techniques have been developed for modification of target tissue and cells in vivo. A number of viral vectors have been developed, such as adenovirus, adeno-associated virus, and retroviruses, as discussed above, which allow for transfection and, in some cases, integration of the virus into the host. See, for example, Dubensky et al. (1984) Proc. Natl. Acad. Sci. USA 81, 7529–7533; Kaneda et al., (1989) Science 243,375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The vector may be administered by injection, e.g. intravascularly or intramuscularly, inhalation, or other parenteral mode. Non-viral delivery methods such as administration of the DNA via complexes with liposomes or by injection, catheter or biolistics may also be used.

In accordance with in vivo genetic modification, the manner of the modification will depend on the nature of the tissue, the efficiency of cellular modification required, the number of opportunities to modify the particular cells, the accessibility of the tissue to the DNA composition to be introduced, and the like. By employing an attenuated or modified retrovirus carrying a target transcriptional initiation region, if desired, one can activate the virus using one of the subject transcription factor constructs, so that the virus may be produced and transfect adjacent cells.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

Binding properties, Assays

Rapamycin is known to bind to the human protein, FKBP12 and to form a tripartite complex with hFKBP12 and FRAP, a human counterpart to the yeast proteins TOR1 and TOR2. Rapalogs may be characterized and compared to rapamycin with respect to their ability to bind to human FKBP12 and/or to form tripartite complexes with human FKBP12 and human FRAP (or fusion proteins or fragments containing its FRB domain). See WO 96/41865 (Clackson et al). That application discloses various materials and methods which can be used to quantify the ability of a compound to bind to human FKBP12 or to form a tripartite complex with (i.e., "heterodimerize") proteins comprising human FKBP12 and the FRB domain of human FRAP, respectively. Such assays include fluorescence polarization assays to measure binding. Also included are cell based transcription assays in which the ability of a compound to form the tripartite complex is measured indirectly by correlation with the observed level of reporter gene product produced by engineered mammalian cells in the presence of the compound. Corresponding cell-based assays may also be conducted in engineered yeast cells. See e.g. WO 95/33052 (Berlin et al).

It will often be preferred that the rapalogs of this invention be physiologically acceptable (i.e., lack undue toxicity toward the cell or organism with which it is to be used), can be taken orally by animals (i.e., is orally active in applications in whole animals, including gene therapy), and/or can cross cellular and other membranes, as necessary for a particular application.

In addition, preferred rapalogs are those which bind preferentially to mutant immunophilins (by way of non-limiting example, a human FKBP in which Phe36 is replaced with a different amino acid, preferably an amino acid with a less bulky R group such as valine or alanine) over native or naturally-occurring immunophilins. For example, such compounds may bind preferentially to mutant FKBPs at least an order of magnitude better than they bind to human FKBP12, and in some cases may bind to mutant FKBPs greater than 2 or even 3 or more orders of magnitude better than they do to human FKBP12, as determined by any scientifically valid or art-accepted assay methodology.

Binding affinities of various rapalogs of this invention with respect to human FKBP12, variants thereof or other immunophilin proteins may be determined by adaptation of known methods used in the case of FKBP. For instance, the practitioner may measure the ability of a compound of this invention to compete with the binding of a known ligand to the protein of interest. See e.g. Sierkierka et al, 1989, Nature 341, 755–757 (test compound competes with binding of labeled FK506 derivative to FKBP).

One set of preferred rapalogs of this invention which binds, to human FKBP12, to a mutant thereof as discussed above, or to a fusion protein containing such FKBP domains, with a Kd value below about 200 nM, more preferably below about 50 nM, even more preferably below about 10 nM, and even more preferably below about 1 nM, as measured by direct binding measurement (e.g. fluorescence quenching), competition binding measurement (e.g. versus FK506), inhibition of FKBP enzyme activity (rotamase), or other assay methodology. In one subset of such compounds, the FKBP domain is one in which phenylalanine at position 36 has been replaced with an amino acid having a less bulky side chain, e.g. alanine, valine, methionine or serine.

A Competitive Binding FP Assay is described in detail in WO96/41865. That assay permits the in vitro measurement of an IC50 value for a given compound which reflects its ability to bind to an FKBP protein in competition with a labeled FKBP ligand, such as, for example, FK506.

One preferred class of compounds of this invention are those rapalogs which have an IC50 value in the Competitive Binding FP Assay better than 1000 nM, preferably better than 300 nM, more preferably better than 100 nM, and even more preferably better than 10 nM with respect to a given FKBP domain and ligand pair, e.g. human FKBP12 or a variant thereof with up to 10, preferably up to 5 amino acid replacements, with a flouresceinated FK506 standard. In one subset of that class, the FKBP domain has one of the abovementioned modifications at position 36.

The ability of the rapalogs to multimerize chimeric proteins may be measured in cell-based assays by measuring the occurrence of an event triggered by such multimerization. For instance, one may use cells containing and capable of expressing DNA encoding a first chimeric protein comprising one or more FKBP-domains and one or more effector domains as well as DNA encoding a second chimeric protein containing an FRB domain and one or more effector domains capable, upon multimerization, of actuating a biological response. We prefer to use cells which further contain a reporter gene under the transcriptional control of a regulatory element (i.e., promoter) which is responsive to the multimerization of the chimeric proteins. The design and preparation of illustrative components and their use in so engineered cells is described in WO96/41865 and the other international patent applications referred to in this and the foregoing section. The cells are grown or maintained in culture. A rapalog is added to the culture medium and after a suitable incubation period (to permit gene expression and secretion, e.g. several hours or overnight) the presence of the reporter gene product is measured. Positive results, i.e., multimerization, correlates with transcription of the reporter gene as observed by the appearance of the reporter gene product. The reporter gene product may be a conveniently detectable protein (e.g. by ELISA) or may catalyze the production of a conveniently detectable product (e.g. colored). Materials and methods for producing appropriate cell lines for conducting such assays are disclosed in the international patent applications cited above in this section. Typically used target genes include by way of example SEAP, hGH, beta-galactosidase, Green Fluorescent Protein and luciferase, for which convenient assays are commercially available.

Another preferred class of compounds of this invention are those which are capable of inducing a detectable signal in a 2-hybrid transcription assay based on fusion proteins containing an FKBP domain. Preferably, the FKBP domain is an FKBP domain other than wild-type human FKBP12.

Another assay for measuring the ability of the rapalogs to multimerize chimeric proteins, like the FKBP-based transcription assay, is a cell-based assay which measures the occurrence of an event triggered by such multimerization. In this case, one uses cells which constitutively express a detectable product. The cells also contain and are capable of expressing DNAs encoding chimeric proteins comprising one or more immunophilin-derived ligand binding domains and one or more effector domains, such as the intracellular domain of FAS, capable, upon multimerization, of triggering cell death. The design and preparation of illustrative components and their use in so engineering cells is described in WO95/02684. See also WO96/41865. The cells are maintained or cultured in a culture medium permitting cell growth or continued viability. The cells or medium are assayed for the presence of the constitutive cellular product, and a base-line level of reporter is thus established. One may use cells engineered for constitutive production of hGH or any other conveniently detectable product to serve as the reporter. The compound to be tested is added to the medium, the cells are incubated, and the cell lysate or medium is tested for the presence of reporter at one or more time points. Decrease in reporter production indicates cell death, an indirect measure of multimerization of the fusion proteins.

Another preferred class of compounds of this invention are those which are capable of inducing a detectable signal in such an FKBP/FRB-based apoptosis assay. Preferably, the FKBP domain is an FKBP domain other than wild-type human FKBP12. In some cases, the FKBP domain is modified, as discussed above. Also preferably, the FRB domain is an FRB domain other than wild-type FRB from human FRAP. In some cases, the FRB domain is modified at position 2098, as described above.

Conducting such assays permits the practitioner to select rapalogs possessing the desired IC50 values and/or binding preference for a mutant FKBP over wild-type human FKBP12. The Competitive Binding FP Assay permits one to select monomers or rapalogs which possess the desired IC50 values and/or binding preference for a mutant FKBP or wild-type FKBP relative to a control, such as FK506.

Applications

The rapalogs can be used as described in WO94/18317, WO95/02684, WO96/20951, WO95/41865, e.g. to regulatably activate the transcription of a desired gene, delete a target gene, actuate apoptosis, or trigger other biological events in engineered cells growing in culture or in whole organisms, including in gene therapy applications. The following are non-limiting examples of applications of the subject invention.

1. Regulated gene therapy. In many instances, the ability to switch a therapeutic gene on and off at will or the ability to titrate expression with precision are important for therapeutic efficacy. This invention is particularly well suited for achieving regulated expression of a therapeutic target gene in the context of human gene therapy. One example uses a pair of chimeric proteins (one containing at least one FRB domain, the other containing at least one FKBP domain), a C3 rapalog of this invention capable of dimerizing the chimeras, and a target gene construct to be expressed. One of the chimeric proteins comprises a DNA-binding domain, preferably a composite DNA-binding domain as described in Pomerantz et al, supra, as the heterologous effector domain. The second chimeric protein comprises a transcriptional activating domain as the heterologous effector domain. The C3 rapalog is capable of binding to both chimeras and thus of effectively cross-linking the chimeras. DNA molecules encoding and capable of directing the expression of these chimeric proteins are introduced into the cells to be engineered. Also introduced into the cells is a target gene linked to a DNA sequence to which the DNA-binding domain is capable of binding. Contacting the engineered cells or their progeny with the C3 rapalog (by administering it to the animal or patient) leads to assembly of the transcription factor complex and hence to expression of the target gene. The design and use of similar components is disclosed in PCT/US93/01617 and in WO 96/41865 (Clackson et al). In practice, the level of target gene expression should be a function of the number or concentration of chimeric transcription factor complexes, which should in turn be a function of the concentration of the C3 rapalog. Dose (of C3 rapalog)-responsive gene expression is typically observed.

The C3 rapalog may be administered to the patient as desired to activate transcription of the target gene. Depending upon the binding affinity of the C3 rapalog, the response desired, the manner of administration, the biological half-life of the rapalog and/or target gene mRNA, the number of engineered cells present, various protocols may be employed. The C3 rapalog may be administered by various routes, including parenterally or orally. The number of administrations will depend upon the factors described above. The C3 rapalog may be taken orally as a pill, powder, or dispersion; bucally; sublingually; injected intravascularly, intraperitoneally, intramuscularly, subcutaneously; by inhalation, or the like. The C3 rapalog (and monomeric antagonist compound) may be formulated using conventional methods and materials well known in the art for the various routes of administration. The precise dose and particular method of administration will depend upon the above factors and be determined by the attending physician or human or animal healthcare provider. For the most part, the manner of administration will be determined empirically.

In the event that transcriptional activation by the C3 rapalog is to be reversed or terminated, a monomeric compound which can compete with the C3 rapalog may be administered. Thus, in the case of an adverse reaction or the desire to terminate the therapeutic effect, an antagonist to the dimerizing agent can be administered in any convenient way, particularly intravascularly, if a rapid reversal is desired. Alternatively, one may provide for the presence of an inactivation domain (or transcriptional silencer) with a ligand binding domain. In another approach, cells may be eliminated through apoptosis via signalling through Fas or TNF receptor as described elsewhere. See International Patent Applications PCT/US94/01617 and PCT/US94/08008.

The particular dosage of the C3 rapalog for any application may be determined in accordance with the procedures used for therapeutic dosage monitoring, where maintenance of a particular level of expression is desired over an extended period of times, for example, greater than about two weeks, or where there is repetitive therapy, with individual or repeated doses of C3 rapalog over short periods of time, with extended intervals, for example, two weeks or more. A dose of the C3 rapalog within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the C3 rapalog is chronically administered, once the maintenance dosage of the C3 rapalog is determined, one could then do assays at extended intervals to be assured that the cellular system is providing the appropriate response and level of the expression product.

It should be appreciated that the system is subject to many variables, such as the cellular response to the C3 rapalog, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like.

2. Production of recombinant proteins and viruses. Production of recombinant therapeutic proteins for commercial and investigational purposes is often achieved through the use of mammalian cell lines engineered to express the protein at high level. The use of mammalian cells, rather than bacteria or yeast, is indicated where the proper function of the protein requires post-translational modifications not generally performed by heterologous cells. Examples of proteins produced commercially this way include erythropoietin, tissue plasminogen activator, clotting factors such as Factor VIII:c, antibodies, etc. The cost of producing proteins in this fashion is directly related to the level of expression achieved in the engineered cells. A second limitation on the production of such proteins is toxicity to the host cell: Protein expression may prevent cells from growing to high density, sharply reducing production levels. Therefore, the ability to tightly control protein expression, as described for regulated gene therapy, permits cells to be grown to high density in the absence of protein production. Only after an optimum cell density is reached, is expression of the gene activated and the protein product subsequently harvested.

A similar problem is encountered in the construction and use of "packaging lines" for the production of recombinant viruses for commercial (e.g., gene therapy) and experimental use. These cell lines are engineered to produce viral proteins required for the assembly of infectious viral particles harboring defective recombinant genomes. Viral vectors that are dependent on such packaging lines include retrovirus, adenovirus, and adeno-associated virus. In the latter case, the titer of the virus stock obtained from a packaging line is directly related to the level of production of the viral rep and core proteins. But these proteins are highly toxic to the host cells. Therefore, it has proven difficult to generate high-titer recombinant AAV viruses. This invention provides a solution to this problem, by allowing the construction of packaging lines in which the rep and core genes are placed under the control of regulatable transcription factors of the design described here. The packaging cell line can be grown to high density, infected with helper virus, and transfected with the recombinant viral genome. Then, expression of the viral proteins encoded by the packaging cells is induced by the addition of dimerizing agent to allow the production of virus at high titer.

3. Biological research. This invention is applicable to a wide range of biological experiments in which precise control over a target gene is desired. These include: (1) expression of a protein or RNA of interest for biochemical purification; (2) regulated expression of a protein or RNA of interest in tissue culture cells (or in vivo, via engineered cells) for the purposes of evaluating its biological function; (3) regulated expression of a protein or RNA of interest in transgenic animals for the purposes of evaluating its biological function; (4) regulating the expression of a gene encoding another regulatory protein, ribozyme or antisense molecule that acts on an endogenous gene for the purposes of evaluating the biological function of that gene. Transgenic animal models and other applications in which the components of this invention may be adapted include those disclosed in PCT/US95/10591.

This invention further provides kits useful for the foregoing applications. Such kits contain DNA constructs encoding and capable of directing the expression of chimeric proteins of this invention (and may contain additional domains as discussed above) and, in embodiments involving regulated gene transcription, a target gene construct containing a target gene linked to one or more transcriptional control elements which are activated by the multimerization of the chimeric proteins. Alternatively, the target gene construct may contain a cloning site for insertion of a desired target gene by the practitioner. Such kits may also contain a sample of a dimerizing agent capable of dimerizing the two recombinant proteins and activating transcription of the target gene.

Formulations, Dosage and Administration

By virtue of its capacity to promote protein—protein interactions, a rapalog of this invention may be used in pharmaceutical compositions and methods for promoting formation of complexes of chimeric proteins of this invention in a human or non-human mammal containing genetically engineered cells of this invention.

The preferred method of such treatment or prevention is by administering to the mammal an effective amount of the compound to promote measurable formation of such complexes in the engineered cells, or preferably, to promote measurable actuation of the desired biological event triggered by such complexation, e.g. transcription of a target gene, apoptosis of engineered cells, etc.

Therapeutic/Prophylactic Administration & Pharmaceutical Compositions

The rapalogs can exist in free form or, where appropriate, in salt form. Pharmaceutically acceptable salts of many types of compounds and their preparation are well-known to those of skill in the art. The pharmaceutically acceptable salts of compounds of this invention include the conventional non-toxic salts or the quaternary ammonium salts of such compounds which are formed, for example, from inorganic or organic acids of bases.

The compounds of the invention may form hydrates or solvates. It is known to those of skill in the art that charged compounds form hydrated species when lyophilized with water, or form solvated species when concentrated in a solution with an appropriate organic solvent.

This invention also relates to pharmaceutical compositions comprising a therapeutically (or prophylactically) effective amount of the compound, and one or more pharmaceutically acceptable carriers and/or other excipients. Carriers include e.g. saline, buffered saline, dextrose, water, glycerol, ethanol, and combinations thereof, and are discussed in greater detail below. The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation.

The pharmaceutical carrier employed may be, for example, either a solid or liquid.

Illustrative solid carrier include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions, and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The carrier or excipient may include time delay material well known to the art, such as glyceryl monostearate or glyceryl distearate along or with a wax, ethylcellulose, hydroxypropylmethylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) has been recognized as providing an acceptable oral formulation for other compounds, and may be adapted to formulations for various compounds of this invention.

A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of the multimerizer may be dissolved in an aqueous solution of an organic or inorganic acid, such as a 0.3M solution of succinic acid or citric acid. Alternatively, acidic derivatives can be dissolved in suitable basic solutions. If a soluble salt form is not available, the compound is dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0–60% of the total volume.

Various delivery systems are known and can be used to administer the multimerizer, or the various formulations thereof, including tablets, capsules, injectable solutions, encapsulation in liposomes, microparticles, microcapsules, etc. Methods of introduction include but are not limited to dermal, intradermal, intramuscular, intraperitoneal, intravenous, subcutaneous, intranasal, pulmonary, epidural, ocular and (as is usually preferred) oral routes. The compound may be administered by any convenient or otherwise appropriate route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In certain embodiments, it may be desirable to administer the compound locally to an area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the compound can also be accomplished topically by administering the compound(s) directly to the affected area of the skin of the individual. For this purpose, the compound is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

In addition, in certain instances, it is expected that the compound may be disposed within devices placed upon, in, or under the skin. Such devices include patches, implants, and injections which release the compound into the skin, by either passive or active release mechanisms.

Materials and methods for producing the various formulations are well known in the art and may be adapted for practicing the subject invention. See e.g. U.S. Pat. Nos. 5,182,293 and 4,837,311 (tablets, capsules and other oral formulations as well as intravenous formulations) and European Patent Application Publication Nos. 0 649 659 (published Apr. 26, 1995; illustrative formulation for IV administration) and 0 648 494 (published Apr. 19, 1995; illustrative formulation for oral administration).

The effective dose of the compound will typically be in the range of about 0.01 to about 50 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient.

The amount of compound which will be effective in the treatment or prevention of a particular disorder or condition will depend in part on the characteristics of the fusion proteins to be multimerized, the characteristics and location of the genetically engineered cells, and on the nature of the disorder or condition, which can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

The invention also provides a pharmaceutical pack or kit comprising one or more containers containing one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration. The notice or package insert may contain instructions for use of a C3 rapalog of this invention, consistent with the disclosure herein.

The invention is further illustrated by the following examples, which should not be construed as further limiting.

The contents of all references, pending patent applications and published patents, cited throughout this application are hereby expressly incorporated by reference.

EXPERIMENTAL EXAMPLES

Synthesis of C3-methallyl-rapamycin and C3-allyl-rapamycin

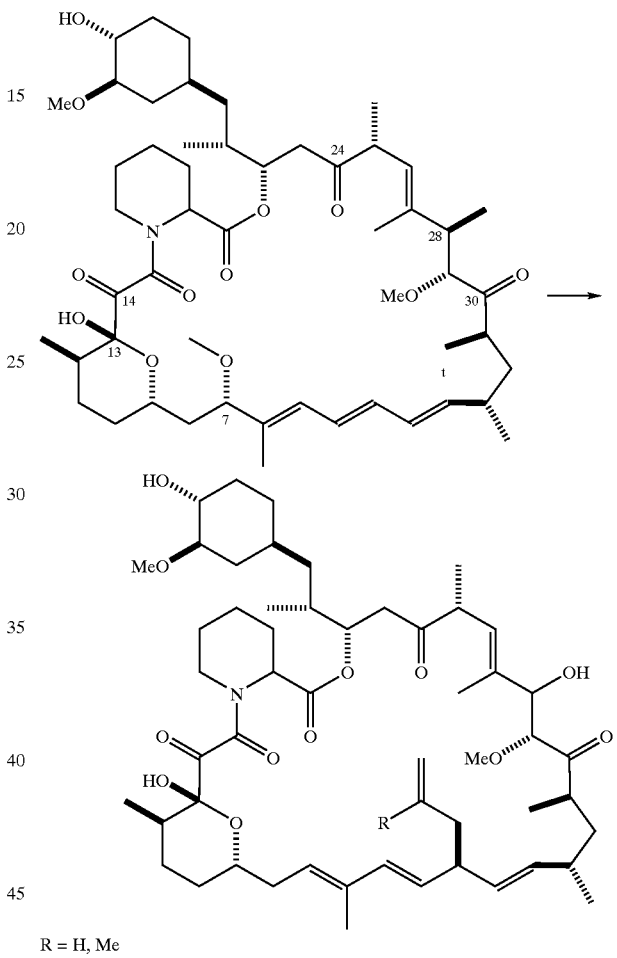

R = H, Me

The synthetic procedure we currently use is a modified version of the procedure described in Liberles et al., July 1997, Proc. Natl. Acad. Sci. USA 94:7825–7830 for the preparation of C7 rapalogs. (Note that C7 and C3 as referred to herein refer to the ring positions C16 and C20, respectively, in the nomenclature of Liberles et al). Twenty two mgs of rapamycin are placed in a 3 ml flame-dried Wheaton vial equipped with a stir bar. The rapamycin is dissolved in 200 μl of methylene chloride and cooled to −40 degrees. Lower temperatures have been found to not work as efficiently. 50 μl of methallyl (or allyl) trimethyl silane (12 equiv.) is added, followed by 40 μl of neat BF3 etherate (13 equivalents). After 2 hours the reaction is over, as determined by TLC, and is quenched by addition of saturated NaHCO$_3$. The reaction mixture is then washed with brine and dried with sodium sulfate. (The aqueous washes can be back-extracted with methylene chloride and combined with the reaction mixture.) The samples are filtered with a 0.45 micron Nylon filter and the solvent is evaporated under vacuum.

The crude product is dissolved in 100 µl of chloroform for injection on the JAI recycling HPLC described below. Three predominant peaks are obtained that can be separated with baseline resolution after approximately 15–20 cycles. (Under certain reaction conditions, a fourth peak appears which elutes before the other three.) Of the three predominant peaks, the first is C7-S methallyl rapamycin, as determined by 1H-NMR. The middle peak is the compound of interest, C3-methallyl rapamycin, and the fourth peak is composed of side products resulting from oversilylation of rapamycin. Following this procedure, we obtained 4.2 mgs of pure C3-methallyl rapamycin. Since unmodified rapamycin coincidentally comigrates precisely with C3-methallyl rapamycin, and cannot be removed efficiently with the JAI, it is critical that rapamycin be completely consumed during the reaction. Overaddition products are far more easily removed than the unreacted starting material.

The JAI-purified methallyl rapamycin can be verified by UV, NMR, and mass spectroscopy and biological activity. The presence of contaminants, such as rapamycin, can be easily determined by UV, as described below.

This same procedure has been used to synthesize C3 allyl-rapamycin, and should be easily extended to synthesize a variety of other C3 derivatives.

Analytical Considerations

One particularly convenient diagnostic is UV spectroscopy. Consistent with disappearance of the triene, the UV spectra of the C3 compounds have a maximum absorbance at lambda 238 rather than 274–282, typically seen for the C7 (R) or (S) compounds. Since the C3 compounds have baseline absorbance in the region where rapamycin absorbs best, UV analysis is a good indicator of sample purity and the presence of any toxic contaminants.

The loss of the triene in C3-methallyl rapamycin is also reflected in the 1H NMR. A 1H-NMR of methallyl rapamycin, taken in CDCL3, reveals a diagnostic peak from C5 at 6.0 ppm. The remainder of the olefinic protons all lie upfield between 5 and 5.6 ppm.

Chromatographic Recovery of the C3 Rapalogs

An instrument made by the Japan Analytical Industry Co., LTD. (JAI) efficiently purifies the C3 rapalogs. The instrument we used was a "LC-908 Recycling Preparative HPLC" and the column we used was "JAIGEL GS-310" with dimensions of "20×500 mm".

Functional Characteristics of C3 Rapalogs

The toxicity of the lead compounds was tested by their ability to inhibit the proliferation of CTLL-2 cells, which are IL-2 dependent and highly sensitive to rapamycin (IC50<1 nM). Incubation of CTLL-2 cells with 1 µM C3-methallyl rapamycin had no detectable effect on proliferation.

Likewise, C3-allyl rapamycin and C3-methallyl rapamycin were impaired in their ability to activate transcription in Jurkat cells transfected with Gal4-FKBP3, wild type FRB-VP16, and UAS-SEAP. (These constructs are described in Liberles et al, above, the full contents of which are incorporated herein by reference.) In experiments in which FRB*-VP16 (FRB harboring T2098L, W2101F, and K2095P) replaces wild type FRB-VP16, reporter gene activity can be detected at an EC50 near 10 nM C3-methallyl rapamycin or C3-allyl rapamycin; as well, the amplitude of reporter gene activity is higher than that elicited by the rapamycin/wild type FRB-VP16 system. C3 derivatives of rapamycin have impaired toxicity (immunosuppressive activity) and can be used efficiently as dimerizers in conjunction with engineered FRB domains.

Preparation of 24(S),30(S)-tetrahydro-C3-rapalogs

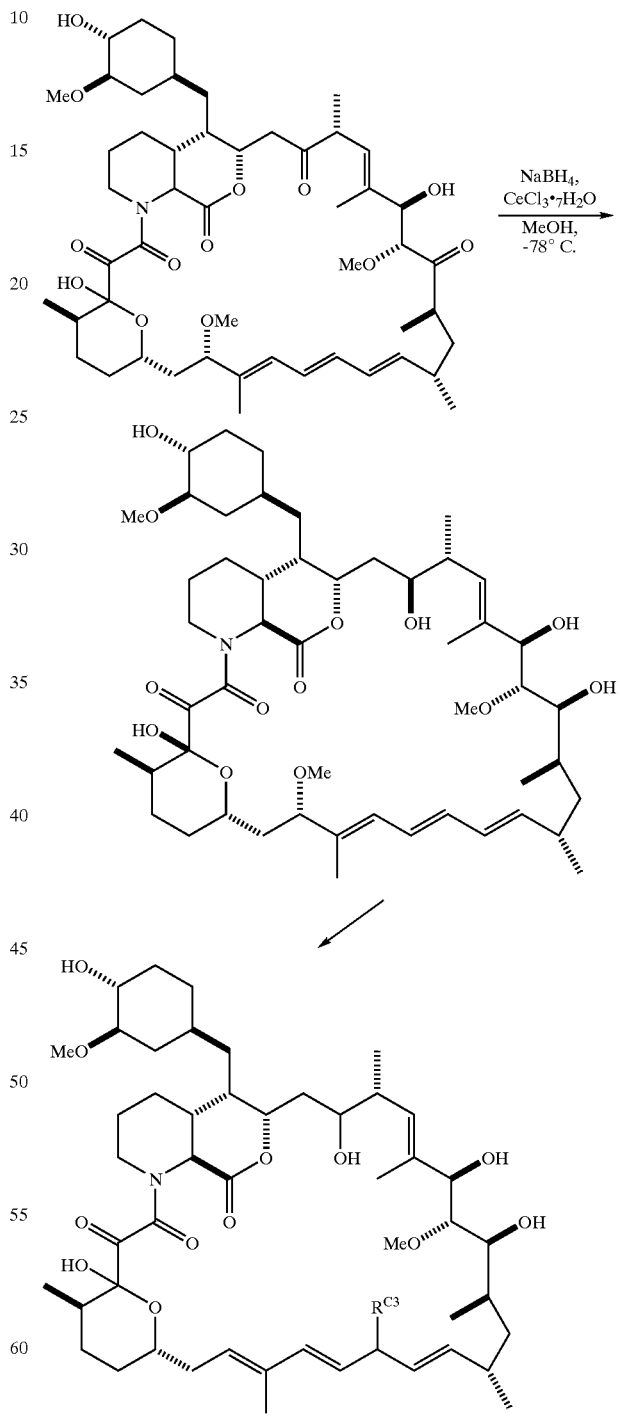

24,30-tetrahydro rapamycin is prepared as described elsewhere and is converted into the desired C3-substituted rapalog by the method described above.

Preparation of 13-fluoro-C3-rapalogs
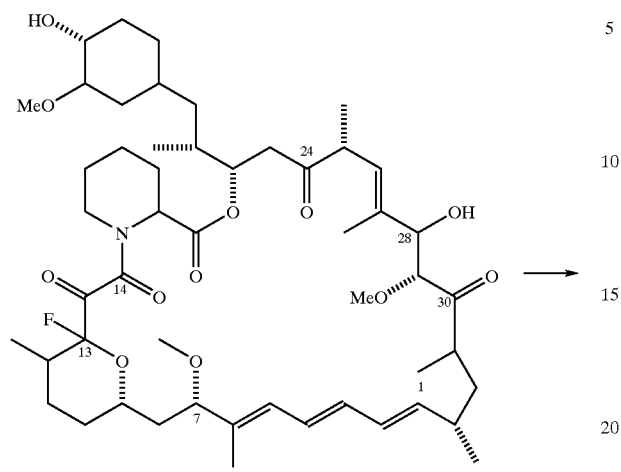
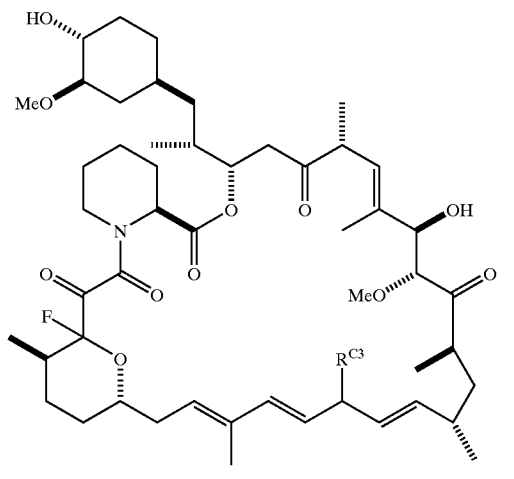
The title compounds are prepared as described above, substituting 13-Fluoro rapamycin for rapamycin.
Preparation of 28-fluoro-C3-rapalogs
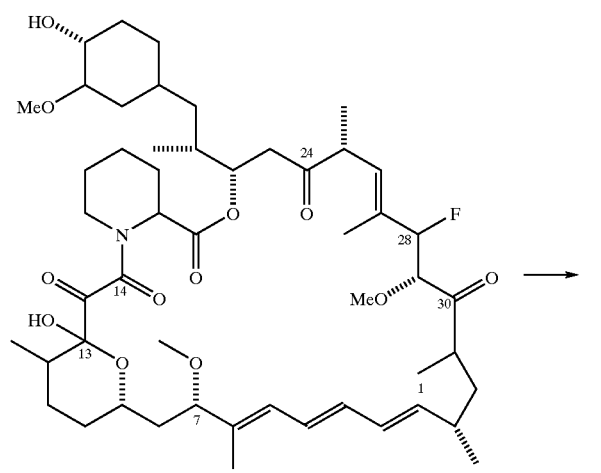
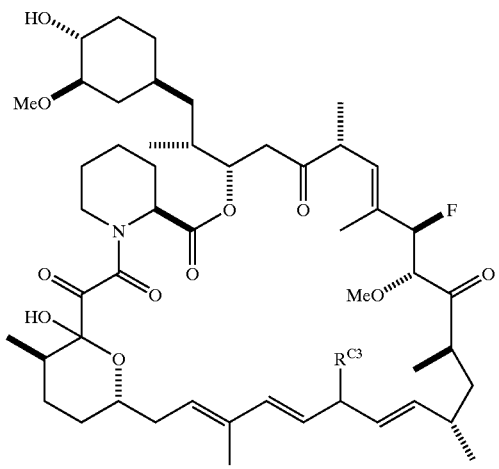
The title compounds are prepared as described above, substituting 28-Fluoro rapamycin for rapamycin.
Preparation of 43-epi-C3-rapalogs
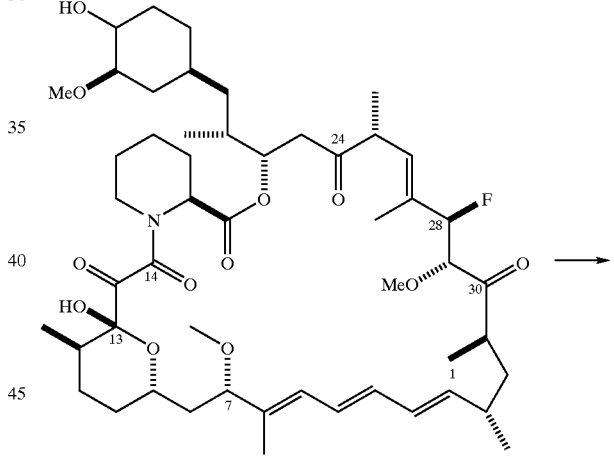
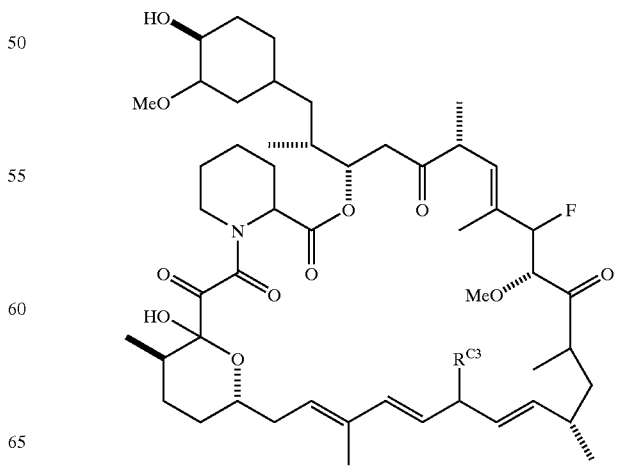

The title compounds are prepared as described above, substituting 43-epi rapamycin for rapamycin.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A compound selected from the group consisting of one of the following structures:

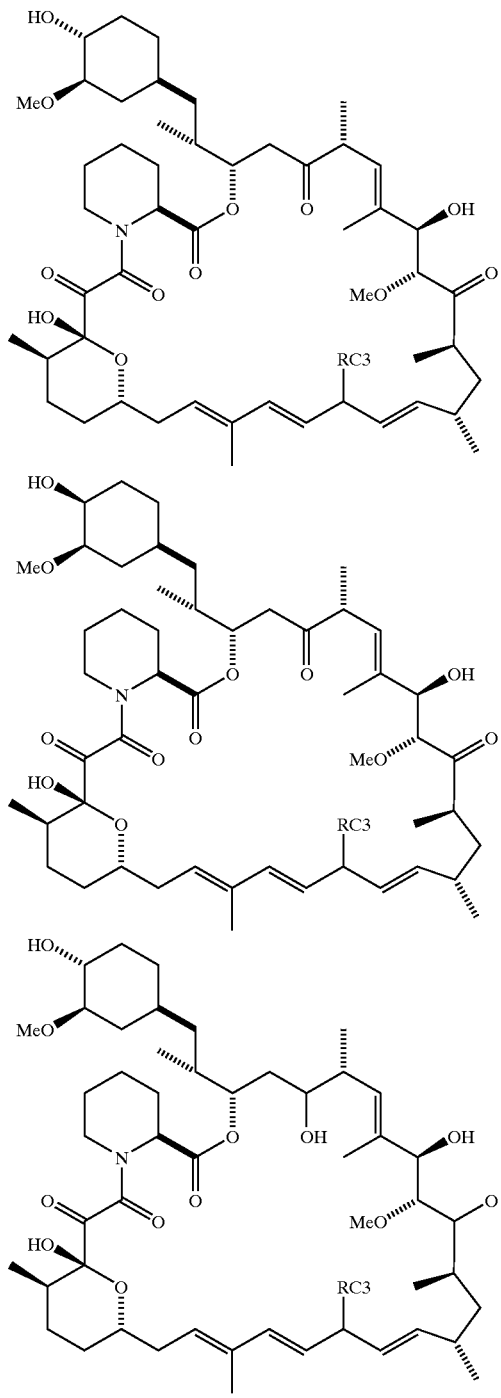

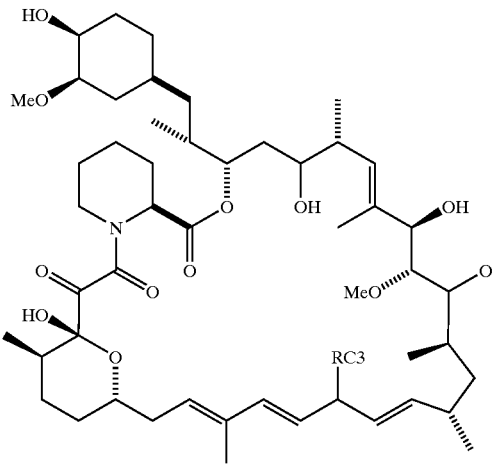

wherein RC3 is an allyl or methallyl moiety, optionally substituted with one or more groups selected from —OH, —SH, —CHO, =O, —COOH, oxime, —NH$_2$, halo, trihaloalkyl, cyano, —SO$_2$CF$_3$, —OSO$_2$F, —OS(O)$_2$R$^{11}$, —SO$_2$—NHR$^{11}$, —NHSO$_2$R$^{11}$, aryl or heteroaryl;

R$^{11}$ is H or an aliphatic, heteroaliphatic, aryl or heteroaryl moiety;

wherein each aryl moiety is a substituted or unsubstituted phenyl ring, and each heteroaryl moiety is selected from a five- or six-membered heteroaryl ring, and each aryl or heteroaryl moiety is optionally substituted with one to five substituents selected from the group consisting of —OH, —SH, —CHO, =O, —COOH, oxime, —NH$_2$, halo, trihaloalkyl, cyano, —SO$_2$—CF$_3$, —OSO$_2$F, —OS(O)$_2$R$^{11}$, —SO$_2$—NHR$^{11}$, —NHSO$_2$R$^{11}$, aryl, heteroaryl, C1–C8 alkoxy, C1 –C8 branched or straight-chain alkyl, acyl, acyloxy, nitro, dialkoxyphenyl, trisubstituted phenyl, —O-aliphatic-COOH, and —O-aliphatic-NH$_2$, each aliphatic moiety is selected from the group consisting of alkyl, alkenyl, alkynyl, cycloalkyl, cycloalkenyl, and cycloalkynyl moieties, optionally substituted with one or more substituents selected from the group consisting of —OH, —SH, —CHO, =O, —COOH, oxime, —NH$_2$, halo, trihaloalkyl, cyano, —SO$_2$—CF$_3$, —OSO$_2$F, OS(O)$_2$R$^{11}$, —SO$_2$—NHR$^{11}$, —NHSO$_2$R$^{11}$, aryl and heteroaryl moieties, and each heteroaliphatic moiety is an aliphatic moiety that contains one or more oxygen, sulfur, nitrogen, phosphorous or silicon atoms.

2. The compound of claim 1, wherein each optionally substituted aryl moiety is selected from the group consisting of phenyl, halophenyl, alkoxyphenyl, dialkoxyphenyl, trialkoxyphenyl, and alkylenedioxyphenyl,; and each optionally substituted heteroaryl moiety is selected from the group consisting of thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, and triazinyll moieties.

3. A composition comprising a compound of claim 1 or 2 and one or more pharmaceutically acceptable excipients.

4. A compound of claim 1 or 2, wherein the compound is at least 95% free from other materials.

5. A compound of claim 1 or 2, wherein the compound is at least 98% free from other materials.

* * * * *

UNITED STATES PATENT AND TRADEMARK OFFICE
CERTIFICATE OF CORRECTION

PATENT NO. : 6,984,635 B1 Page 1 of 1
DATED : January 10, 2006
INVENTOR(S) : Schreiber et al.

It is certified that error appears in the above-identified patent and that said Letters Patent is hereby corrected as shown below:

<u>Column 1,</u>
Line 6, insert -- This invention was supported by NIH Grant No. GM52067 and CA39612 and the government has certain rights to the invention. --.

Signed and Sealed this

Fourth Day of April, 2006

JON W. DUDAS
*Director of the United States Patent and Trademark Office*

UNITED STATES PATENT AND TRADEMARK OFFICE
CERTIFICATE OF CORRECTION

PATENT NO. : 6,984,635 B1  Page 1 of 2
APPLICATION NO. : 09/248755
DATED : January 10, 2006
INVENTOR(S) : Schreiber et al.

It is certified that error appears in the above-identified patent and that said Letters Patent is hereby corrected as shown below:

In Claim 1, column 1, line 50, please replace compound " 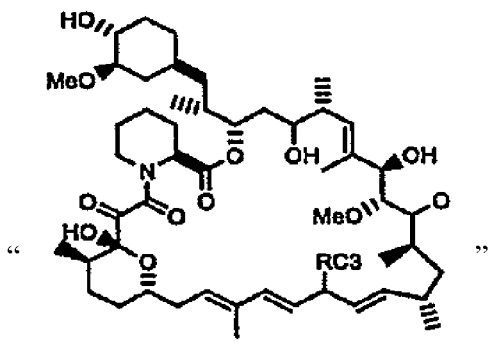 "

with compound -- 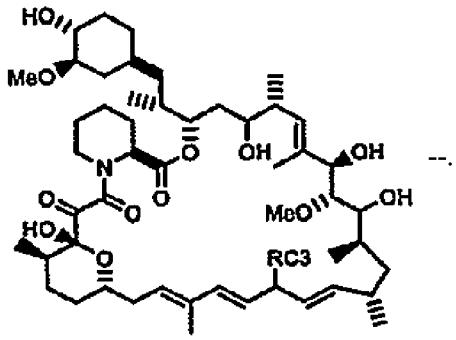 --.

UNITED STATES PATENT AND TRADEMARK OFFICE
CERTIFICATE OF CORRECTION

PATENT NO. : 6,984,635 B1                                          Page 2 of 2
APPLICATION NO. : 09/248755
DATED : January 10, 2006
INVENTOR(S) : Schreiber et al.

It is certified that error appears in the above-identified patent and that said Letters Patent is hereby corrected as shown below:

In Claim 1, column 2, line 1, please replace compound " 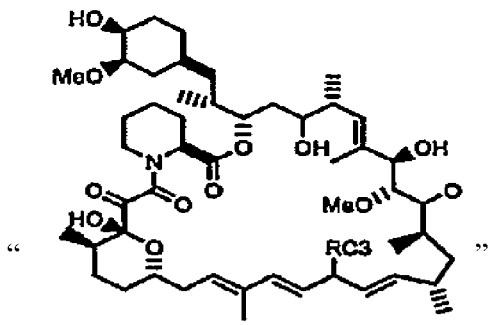 "

with compound -- 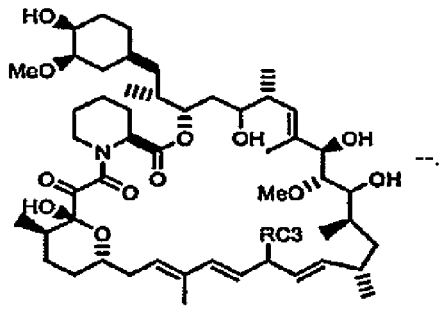 --.

Signed and Sealed this

Twentieth Day of February, 2007

JON W. DUDAS
*Director of the United States Patent and Trademark Office*